US010953013B2

(12) United States Patent
Benes et al.

(10) Patent No.: US 10,953,013 B2
(45) Date of Patent: Mar. 23, 2021

(54) BIOMARKERS OF RESPONSE TO NAE INHIBITORS

(71) Applicants: Millennium Pharmaceuticals, Inc., Cambridge, MA (US); The General Hospital Corporation, Boston, MA (US)

(72) Inventors: Cyril H. Benes, Brookline, MA (US); Stephen J. Blakemore, Littleton, MA (US); Jonathan L. Blank, Westborough, MA (US); Eric S. Lightcap, Natick, MA (US); George J. Mulligan, Lexington, MA (US); Matthew C. Schu, Somerville, MA (US); Peter G. Smith, Arlington, MA (US); Jeffrey E. Settleman, Mill Valley, CA (US)

(73) Assignees: Millennium Pharmaceuticals, Inc., Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/173,393

(22) Filed: Jun. 3, 2016

(65) Prior Publication Data

US 2017/0105995 A1 Apr. 20, 2017

Related U.S. Application Data

(63) Continuation of application No. 14/354,155, filed as application No. PCT/US2012/062263 on Oct. 26, 2012.

(60) Provisional application No. 61/552,686, filed on Oct. 28, 2011.

(51) Int. Cl.

| | |
|---|---|
| ***C12Q 1/6886*** | (2018.01) |
| ***A61K 31/519*** | (2006.01) |
| ***G01N 33/574*** | (2006.01) |
| ***G16H 20/40*** | (2018.01) |
| *A61P 35/02* | (2006.01) |
| *A61P 43/00* | (2006.01) |

(52) U.S. Cl.

CPC .......... *A61K 31/519* (2013.01); *C12Q 1/6886* (2013.01); *G01N 33/57484* (2013.01); *G16H 20/40* (2018.01); *A61P 35/02* (2018.01); *A61P 43/00* (2018.01); *C12Q 2600/106* (2013.01); *C12Q 2600/156* (2013.01); *G01N 2800/52* (2013.01); *G01N 2800/60* (2013.01); *Y02A 90/10* (2018.01)

(58) Field of Classification Search

None

See application file for complete search history.

(56) References Cited

U.S. PATENT DOCUMENTS

| | | | | |
|---|---|---|---|---|
| 5,382,510 | A * | 1/1995 | Levine | C07K 14/4746 435/6.12 |
| 5,707,863 | A | 1/1998 | Trofatter et al. | |
| 8,207,177 | B2 | 6/2012 | Langston et al. | |
| 9,827,246 | B2 | 11/2017 | Blakemore et al. | |
| 2003/0092019 | A1 | 5/2003 | Meyer et al. | |
| 2006/0281122 | A1 | 12/2006 | Bryant et al. | |
| 2007/0191293 | A1* | 8/2007 | Langston | A61P 37/02 514/43 |
| 2010/0227838 | A1 | 9/2010 | Shah et al. | |
| 2011/0097389 | A1 | 4/2011 | Sobol et al. | |
| 2012/0077814 | A1* | 3/2012 | Wang | C07D 487/04 514/243 |
| 2012/0156197 | A1* | 6/2012 | Errico | C07K 16/44 424/133.1 |
| 2012/0258927 | A1 | 10/2012 | Langston et al. | |
| 2012/0258977 | A1 | 10/2012 | Langston et al. | |
| 2013/0165457 | A9 | 6/2013 | Langston et al. | |
| 2013/0289037 | A1 | 10/2013 | Langston et al. | |
| 2015/0105411 | A1 | 4/2015 | Blakemore et al. | |
| 2015/0119410 | A1 | 4/2015 | Benes et al. | |
| 2015/0240315 | A1 | 8/2015 | Blakemore et al. | |
| 2017/0105995 | A1 | 4/2017 | Benes et al. | |
| 2017/0136024 | A1 | 5/2017 | Langston et al. | |

FOREIGN PATENT DOCUMENTS

| | | | |
|---|---|---|---|
| CN | 101379061 | A | 3/2009 |
| JP | 7-143884 | A | 6/1995 |
| WO | WO 2006/084281 | A1 | 8/2006 |
| WO | WO 2007/092213 | A2 | 8/2007 |
| WO | WO 2008/019124 | A1 | 2/2008 |
| WO | WO 2011/068863 | A1 | 6/2011 |

(Continued)

OTHER PUBLICATIONS

"Affymetric GeneChip Human Fenome U133 Array Set HG-U133A," Mar. 11, 2002 (Accession Display) GEO Database [online] Bethesda, MD, USA: National Center for Biotechnology Information. GEO, Platform GPL96.

(Continued)

*Primary Examiner* — Katherine D Salmon

(74) *Attorney, Agent, or Firm* — Sterne, Kessler, Goldstein & Fox P.L.L.C.

(57) ABSTRACT

Disclosed herein are markers whose mutational status is associated with sensitivity to treatment with NAE inhibitors. Mutational status is determined by measurement of characteristics of markers associated with the marker genes. Compositions and methods are provided to assess markers of marker genes to predict response to NAE inhibition treatment.

12 Claims, 7 Drawing Sheets

Figure 1:
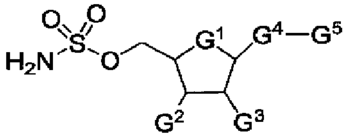

Specification includes a Sequence Listing.

(56) References Cited

FOREIGN PATENT DOCUMENTS

WO WO 2013/063481 A1 5/2013
WO WO 2013/063496 A1 5/2013

OTHER PUBLICATIONS

Abbas, T., et al., "PCNA-dependent regulation of p21 ubiquitylation and degradation via the CRL4Cdt2 ubiquitin ligase complex," *Genes & Development*, 22: 2496-2506 (2008).
Bignell, G., et al., "Signatures of mutation and selection in the cancer genome," *Nature*, 463:893-890 (2010).
Brognard, J., et al., "Cancer-Associated Loss-of-Function Mutations Implicate DAPK3 as a Tumor-Suppressing Kinase," *Cancer Res*, 71(8): 3152-3161 (2011).
Chai, V., et al., "Optimization of the PAXgene™ blood RNA extraction system for gene expression analysis of clinical samples," *J Clin Lab Anal*, 19(5): 182-188 (2005).
Evans, E., et al., "Pharmacogenomics: Translating Functional Genomics into Rational Therapeutics," *Science*, 286: 487-491 (1999).
Futreal, P. A., et al., "A census of human cancer genes," *Europe PMC Funder Group*, Author Manuscript, Final Publication: *Nat Rev Cancer*, 4(3): 177-183 (2004).
Gurrieri, C., et al., "Mutations of the PML tumor suppressor gene in acute promyeloctic leukemia," *Blood*, 103: 2358-2362 (2004).
Hong, S., et al., "Identification of JmjC domain-containing UTX and JMJD3 as histone H3 lysine 27 demethylases," *PNAS*, 104(47): 18439-18444.
Jia, L., et al., "Induction of p21-Dependednt Senescence by an NAE Inhibitor, MLN4924, as a Mechanism of Growth suppression," *Neoplasia*, 13(6): 561-569 (2011).
Juppner, H., et al., "Functional Properties of the PTH/PTHrP Receptor,"*Bone*, 17(2 Supplement): 39S-42S (1995).
Kim, Y., et al., "The CRL4$^{Cdt2}$ ubiquitin ligase targets the degradation of p21$^{Cip1}$to control replication licensing," *Genes & Development*, 22: 2507-2519 (2008).
Kuang, C., et al., "Tumor-derived C-terminal mutations of Smad4 with decreased DNA binding activity and enhanced intramolecular interaction," *Oncogene*, 23: 1021-1029 (2004).
Li, W., et al., "Merlin's Tumor Suppression Linked to Inhibition of the E3 Ubiquitin Ligase CRL4(DCAF1)," *Cell Cycle*, 9(22): 4433-4436 (2010).
Li, B. et al., "Investigation of efficacy of the NAE inhibitor MLN4924 across large-scale cell line panels, reveals potentially sensitive cancer indications and candidate predictive biomarkers," *Mol. Cancer Ther.*, vol. 10(11): *Abstract A45*, 2011.
Liao, H., et al., "Quantitative Proteomic Analysis of Cellular Protein Modulation upon Inhibition of the NEDD8-Activating Enzyme of MLN4924," *Molecular & cellular Proteomics*, 10(11): 1-11 (2011).
Lin, J. J., et al., "NEDD8 Targeting Drug MLN4924 Elicits DNA Rereplication by Stabilizing Cdt1 in S Phase, Triggering Checkpoint Activation Apoptosis and Senescence in Cancer Cells," *Cancer Res*, 70(24): 10310-10320 (2010).
Lin, H. K., et al., "Skp2 targeting suppresses tumorigenesis by Arf-p53-Independent cellular senescence," *Nature*, 464:374-379 (2010).
Lipkowitz, S., et al., "RINGs of good and evil: RING finger ubiquitin ligases at the crossroads of tumour suppression and oncogenesis," *Nat Rev Cancer*, 11(9): 629-643 (2013).
McDermott, U., et al., "Identification of genotype-correlated sensitivity to selective kinase inhibitors by using high-throughput tumor cell line profiling," *PNAS*, 104(50): 19936-19941 (2007).
Milhollen, M. A., et al., "Inhibition of NEDD8-Activating Enzyme Induces Rereplication and Apoptosis in Human Tumor cells Consistent with Deregulating CDT1 Turnover," *Cancer Res*, 71(8): 3042-3051 (2011).
Milhollen, M. A., et al., "Treatment-Emergent Mutations in NAEβ Confer Resistance to the NEDD8-Acticating Enzyme Inhibitor MLN4924," *Cancer Cell*, 21: 388-401 (2012).
Miyaki, T., et al., "Role of Smad4 (DPC4) Inactivation in human cancer," *Biochem Biophys Res Commun*, 306: 799-804 (2003).
Mummidi, S., et al., "Evolution of Human and Non-human Primate CC Chemokine Receptor 5 Gene and mRNA," *J. Biol. Chem.*, 275(25): 18946-18961 (2000).
Nishitani, H., et al., "CDK Inhibitor p21 is Degraded by a Proliferating cell Nuclear Antigen-coupled Cul4-DDB1$^{Cdt2}$ Pathway during S Phase and after UV Irraditation," *J. Biol. Chem.*, 283(43): 29045-29052 (2008).
Norquist, B., et al., Secondary Somatic Mutations Restoring BRCA1/2 Predict Chemotherapy Resistance in Hereditary Ovarian Carcinomas, *J. Clin. Oncol.*, 29(22): 3008-3015 (2011).
O'Day, C., et al., "240 human tumor cell line profiling to evaluate relationships between tumor genotypes and cancer cell sensitivity," *Abstract*; AACR International Conference: Molecular Diagnostics in Cancer Therapeutic Development—Sep. 27-30, 2010; Denver, CO. Publishes in *Clin Cancer Res*, 16(19 Supplemental).
Pan, Z. Q., et al., "Nedd8 on cullin: building an expressway to protein destruction," *Oncogene*, 23: 1985-1997 (2004).
Saddler, C., et al., "Comprehensive biomarker and genomic analysis identifies p53 status as the major determinant of response to MDM2 inhibitors in chronic lymphocytic leukemia," *Blood*, 111(3): 1584-1593 (2008).
Sao, P. S., et al., "Identification of Erythrocyte p55/MPP1 as a Binding Partner of NF2 Tumor Suppressor Protein/Merlin," *Exp Biol Med (Maywood)*, 234(3): 255-262 (2009).
Soucy, T., et al., "An inhibitor of NEDD8-activating enzyme as a new approach to treat cancer," *Nature*, 458:732-736 (2009).
Soucy, T., et al., "The NEDD8 Conjugation Pathway and its Relevance in Cancer Biology and Therapy," *Genes & Cancer*, 1(7): 708-716 (2010).
Stankovic, T., et al., "ATM Mutations in Sporadic Lymphoid Tumours," *Leukemia and Lymphoma*, 43(3): 1563-1571 (2002).
Swords, R. T., et al., "Inhibition of NEDD8-activating enzyme: a novel approach for the treatment of acute myeloid leukemia," *Blood*, 115: 33796-3800 (2010).
Takahash S., "Current finding for recurring mutations in acute myeloid leukemia," *Journal of Hematology & Oncology*, 4(36) (2011).
Van Haaften, G., et al., "Somatic mutations of the historic H3K27 demethylase, UTX, in human cancer," *Nat. Genet.*, 41(5): 521-523 (2009).
Virappane, P., et al., "Mutation of the Wilms' Tumor 1 Gene is a Poor Prognostic Factor Associated With Chemotherapy Resistance in Normal Karyotype Acute Myeloid Leukemia: The United Kingdom Medical Research Council Adult Leukemia Working Party," *J. Clin. Oncol.*, 26(33): 5429-5425 (2008).
Watson, I. R., et al., "NEDD8 Pathways in Cancer, Sine Quibus Non," *Cancer Cell*, 19: 168-176 (2011).
Xirodimas, D. P., et al., "Mdm2-Mediated NEDD8 Conjugation of p53 Inhibits its Transcriptional Activity," *Cell*, 118: 83-97 (2004).
International Search Report of the International Searching authority dated Mar. 8, 2013 issued in International Application No. PCT/US2012/62263 and Written Opinion, which corresponds to U.S. Appl. No. 14/354,155.
International Search Report of the International Searching authority dated Jan. 22, 2013 issued in International Application No. PCT/US2012/62240 and Written Opinion, which corresponds to U.S. Appl. No. 14/354,149.
European Extended Search Report of the European Searching Authority dated May 15, 2015, issued in European Application No. 12843416.4 and Written Opinion, which corresponds to U.S. Appl. No. 14/354,149.
European Extended Search Report of the European Searching Authority dated Oct. 29, 2015, issued in European Application No. 12844605.1 and Written Opinion, which corresponds to U.S. Appl. No. 14/354,149.
Office Action dated Dec. 4, 2015 in abandoned U.S. Appl. No. 14/354,155.
U.S. Appl. No. 14/432,587, filed Mar. 31, 2015; Blackemore et al.
Kauh, J.S., et al., "MLN4924, an investigational NEDD8-activating enzyme (NAE) inhibitor, in patients (pts) with advanced solid tumors: Phase I study of multiple treatment schedules," J. of Clin. Oncol. 29(15 suppl.):3013-3013, ASCO. Unites States (2011).

(56) References Cited

OTHER PUBLICATIONS

International Preliminary Report on Patentability for PCT/US2012/062263, ISA, Geneva, Switzerland, dated Apr. 29, 2014, 8 pages.

Gu, Y., et al., "MLN4924, an NAE inhibitor, suppresses AKT and mTOR signaling via upregulation of REDD1 in human myeloma cells," Blood 123(21):3269-76, The American Society of Hematology, United States (2014).

* cited by examiner

FIG4A.
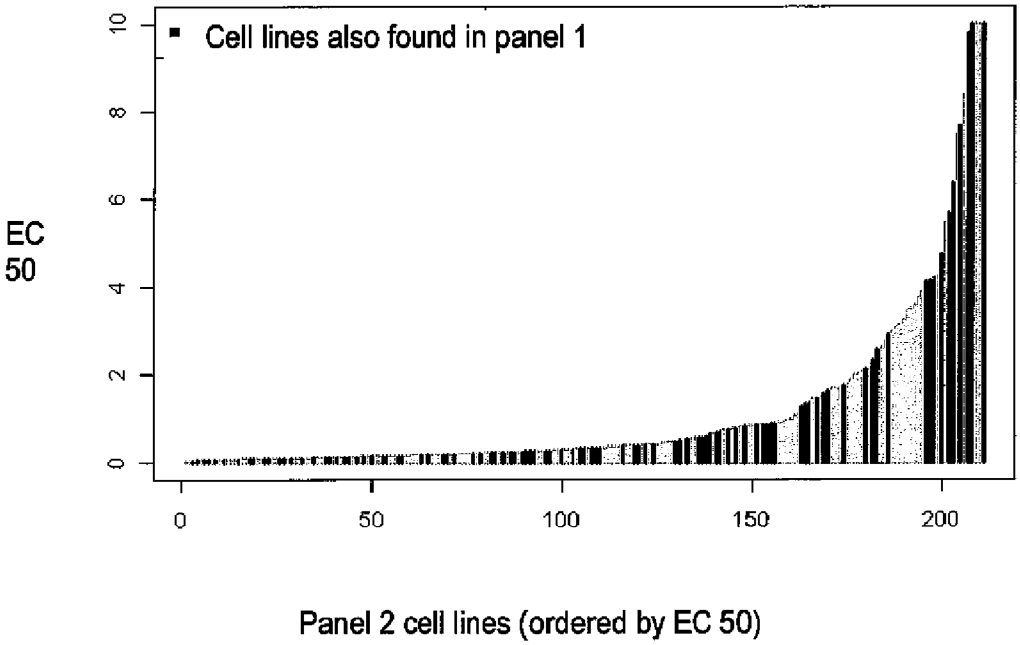
FIG4B.
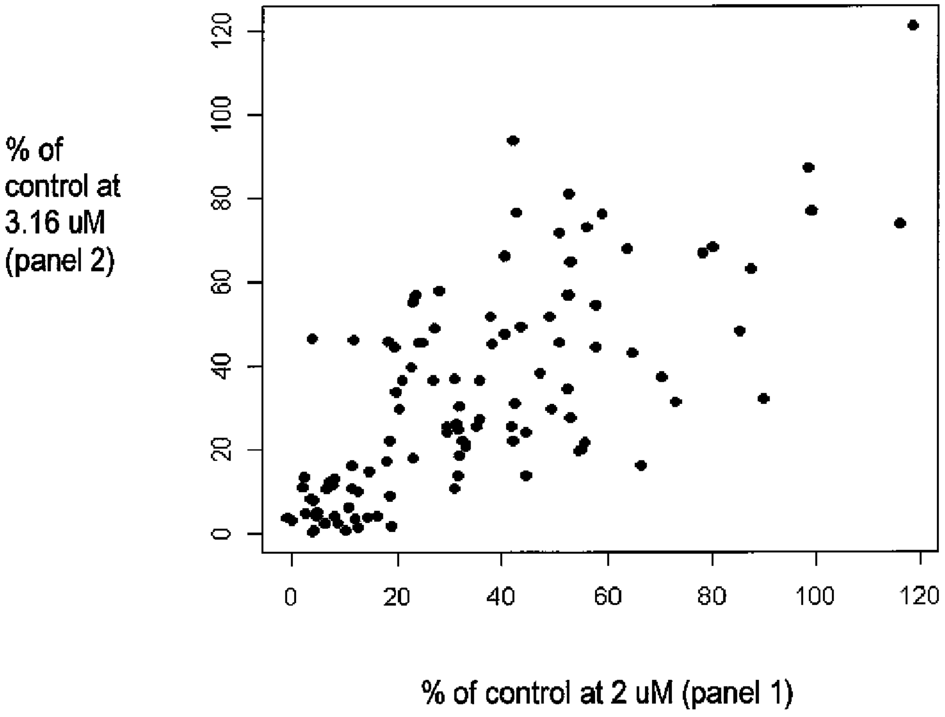
FIG. 4

SEQUENCE LISTING

<160> NUMBER OF SEQ ID NOS: 26

<210> SEQ ID NO 1
<211> LENGTH: 6046
<212> TYPE: DNA
<213> ORGANISM: Homo Sapiens

<400> SEQUENCE: 1

```
tgcgcttccc gcgggcgcgc ggagtgagga cggtgacagc cacgcgcgcg cgtacgcgcc     60
cgatgcagcg cggccccgtg accctagtcg gccgctgaga ggcgcgcgga gtctgggccg    120
ctgccgtcta ggggtcccgt cccgaggcgt ccccggcatc tccggcccga atcccggagt    180
gccgggtcgc gcctgcaccg aaggtcccgg ctcctgtgcc ctccctgcag ccgtcagggc    240
ccgtccccca actccccttt ccgctcaggc agggtcctcg cggcccatgc tggccgctgg    300
ggacccgcgc agcccagacc gttcccgggc cgggcagccg gccaccatgg tggccctgag    360
gcctgtgcag caactccagg ggggctaaag ggctcagagt gcaggccgtg gggcgcgagg    420
gtcccgggcc tgagccccgc gccatggccg gggccatcgc ttcccgcatg agcttcagct    480
ctctcaagag gaagcaaccc aagacgttca ccgtgaggat cgtcaccatg gacgccgaga    540
tggagttcaa ttgcgagatg aagtggaaag ggaaggacct ctttgatttg gtgtgccgga    600
ctctggggct ccgagaaacc tggttctttg gactgcagta cacaatcaag gacacagtgg    660
cctggctcaa aatggacaag aaggtactgg atcatgatgt ttcaaaggaa gaaccagtca    720
cctttcactt cttggccaaa ttttatcctg agaatgctga agaggagctg gttcaggaga    780
tcacacaaca tttattcttc ttacaggtaa agaagcagat tttagatgaa aagatctact    840
gccctcctga ggcttctgtg ctcctggctt cttacgccgt ccaggccaag tatggtgact    900
acgaccccag tgttcacaag cggggatttt tggcccaaga ggaattgctt ccaaaaaggg    960
taataaatct gtatcagatg actccggaaa tgtgggagga gagaattact gcttggtacg   1020
cagagcaccg aggccgagcc agggatgaag ctgaaatgga atatctgaag atagctcagg   1080
acctggagat gtacggtgtg aactactttg caatccggaa taaaaagggc acagagctgc   1140
tgcttggagt ggatgccctg gggcttcaca tttatgaccc tgagaacaga ctgaccccca   1200
agatctcctt cccgtggaat gaaatccgaa acatctcgta cagtgacaag gagtttacta   1260
ttaaaccact ggataagaaa attgatgtct tcaagtttaa ctcctcaaag cttcgtgtta   1320
ataagctgat tctccagcta tgtatcggga accatgatct atttatgagg agaaggaaag   1380
ccgattcttt ggaagttcag cagatgaaag cccaggccag ggaggagaag gctagaaagc   1440
agatggagcg gcagcgcctc gctcgagaga agcagatgag ggaggaggct gaacgcacga   1500
```

-continued

```
gggatgagtt ggagaggagg ctgctgcaga tgaaagaaga agcaacaatg gccaacgaag   1560
cactgatgcg gtctgaggag acagctgacc tgttggctga aaaggcccag atcaccgagg   1620
aggaggcaaa acttctggcc cagaaggccg cagaggctga gcaggaaatg cagcgcatca   1680
aggccacagc gattcgcacg gaggaggaga agcgcctgat ggagcagaag gtgctggaag   1740
ccgaggtgct ggcactgaag atggctgagg agtcagagag gagggccaaa gaggcagatc   1800
agctgaagca ggacctgcag gaagcacgcg aggcggagcg aagagccaag cagaagctcc   1860
tggagattgc caccaagccc acgtacccgc ccatgaaccc aattccagca ccgttgcctc   1920
ctgacatacc aagcttcaac ctcattggtg acagcctgtc tttcgacttc aaagatactg   1980
acatgaagcg gctttccatg gagatagaga aagaaaaagt ggaatacatg gaaaagagca   2040
agcatctgca ggagcagctc aatgaactca agacagaaat cgaggccttg aaactgaaag   2100
agagggagac agctctggat attctgcaca atgagaactc cgacaggggt ggcagcagca   2160
agcacaatac cattaaaaag ctcaccttgc agagcgccaa gtcccgagtg gccttctttg   2220
aagagctcta gcaggtgacc cagccacccc aggacctgcc acttctcctg ctaccgggac   2280
cgcgggatgg accagatatc aagagagcca tccataggga gctggctggg ggtttccgtg   2340
ggagctccag aactttcccc agctgagtga agagcccagc ccctcttatg tgcaattgcc   2400
ttgaactacg accctgtaga gatttctctc atggcgttct agttctctga cctgagtctt   2460
tgttttaaga agtatttgtc ttcctttgtc taatgtggga ttcctgactc ccttcgtcca   2520
aggcaccggt gtgtgtgtgt cttgcactcc agagctgacc tccaccgccc agcctgggaa   2580
gtcattgtag ggagtgagac actgaagccc tgagaagcca gtgccatcat ccccaccccg   2640
cccagggttc cggaacattc attcccccac cggtgaggac ctggcatgca gcgaagcagc   2700
ccagcccggc ggatcccagg ccagcacgcc tgccggcttc tcatcgtcag ggagcccgcc   2760
cagagctcgt gacgagcaag tgctgggtcc ccgccaggca ccccgaggcg gcgctctggc   2820
tggcagctgg tggggaatag gcagggcagc tgtggctggg gagagacttt aggcagaagc   2880
tgtgatgcag gctgactgcc agccgagggg ctgggtagtg ccgtgcggga gctgatggta   2940
cagggcactc gctgtccccc tccggccacc ctagaccagg gtccgagagg caggcaggag   3000
ccactcatgt cttccccatt gcccgacgcc catagacgct ccttcctgtg tggggctggg   3060
gtactccctg gtcgtactgc agtcagcacc cgtaacccgg ctatgaccag ggatctgtaa   3120
gccctgtggc tccacaggtg ctgcttctca ctggcccaga ctctgagctc caccggccca   3180
gtctgcacgg cccatctgct tcaccttccc tcccagccac gtgccagtgg ccacagccca   3240
cttcccaacc cactgttgta cccaggcctc actttgctgt tgcccttgtc cctcttcggg   3300
ccctgaattt tctgttccct gggggccagc cagggccctt tgtgcccctc ccagcacagg   3360
cctgatgcag gtgtccactc acaggtggcg ctcacctagg ctgtcacagg acccacctcc   3420
atgccaggca acagagggcc acagaaccac ccccacggct cactccttgg tctggggcca   3480
ccttcttgcc ctttcttttt tttttttttt tttttttccc gagatggagt ctctctctgt   3540
cacccaggtg ggagtgtggt ggcacaatct cggctcactg caacctccac ctcctgagtt   3600
caagcaattc tcctgcctca gcctcccaag tagctgggac tacaggcatg caccaccaca   3660
cttggccaat gttctgtatt tttaataggg acggggtttt gccatgttag ctaggctggt   3720
ctcaaactca cacctgggat tacaggcatg agccactgca cccagcccct tcttgccctt   3780
tcttttctcc atggctgatg ctgctgtggc cagccagggc ccttgagatc cttccagttt   3840
ggctgttatg caaagcaggt gatttgtctt aatcagataa aagatagagg ctatgggggc   3900
```

```
ctcaagattt ttggagagca gaggtggtct ctggcaattc catctggttt tgagaaactt   3960

agcagctcac agagcacaga gatcctgcct tcttcctact atcaggctga cctaatgggg   4020

ttgggctgct cggcaactgc ttgggtcacc ttgccccaag gaaaccagcc ctgggtgcca   4080

cccagccact tagggtctac agggtgggac tccagaccta gagcgtaagt atggatgttg   4140

tggccctgtg tcttcctagt gtgacccagc caggagcgga agcttcaggc gtttgtaaag   4200

tgaggtctgg ctctgcctcc tccgtttttt tttttttct gtttctgttt ctgtttttt   4260

tttgagatgg agtctcgctc tgtcgcccag gctggagtgc agtgtcacga tctcagctca   4320

ctgcaacctc cgcctcccag gtacaagaga ttctcctgcc tcagcctccc gagtagctgg   4380

gactacaggc gtgtgccacc atgcctggct aatttttgta tttttagtag agatggggtt   4440

tcgccatgtt agccagactg gtctcgaact cctgacctca ggtgatcctc ccaccccggc   4500

ttcccaaagt tctgggatta taggcgtgag ccaccatgcc cggtctcttc tcagtcttga   4560

agcccatccc tggatttcca ccaggagtta ctttcctcct gacctgtaaa tttgttcttt   4620

aacaatggct gcaggtggga gcatatggtg gtttataaaa acgctgtcgg gctttgtttc   4680

cttctttagc tgccgtgtct acttctgaag tctgggaagt gccaagccac gcggcctcaa   4740

gggagctggc tggtgtttga gctgtggcag aagcacctgg ggctccaggg agcaggctgg   4800

gaactgcagg accttgctca gccaggagca cttccccctc cttgaggcag gaatactgag   4860

gtgcctcccc acagatggag aaggtggaga ggaggatggg cctcaggagc atctcaagcc   4920

ccagtagcag gagaaagaaa gaaagagatg cctggttttc acagactggt tcctgtggct   4980

gggatgactg catccttttt tttttttttt tgagacggag tttttgcctt tgtcgcccag   5040

gctggagtgc aatggcgtga tctcggctca ccgcaacctc cgcctcccgg attcaagcaa   5100

ttctcctgcc tcagcctccc gagtagctgg gattacaggc acgcacctcc acgtccggct   5160

aattttgtat ttttagtgga gacggggttt ctccatgtcg gtcaggctgg tctcgaactc   5220

ccgacctcag gtgatctgcc cacctcggcc tcccaaagtg ctgggattac aggcatgagc   5280

caccgcgctt ggccagactg cgtccttttt aagcgaacat tttagggcct gggagtttgt   5340

caagtaagga agtctcaagc ccaaagagca gcgtcctgac catggtggtt tcattacgag   5400

cccttctgct ggctctcagg cagaagcccc acagcaccgg gaccattcat gaggtcactg   5460

cccagctcat gatgtccgtg aggctgtcct tttggccagt agccgtgtgc agctgtgtgg   5520

cacagatggc ttcgttcatc ctgatcaagg ccccacctca gccacagcag tccccccaac   5580

ctgtgttgtc caccctatta ttcatgtacc tgccaggccc tgctagatag caccccgtgg   5640

cattacataa cacttcatga gtggctgtgt cttgtaattt tggggacagg tttctctctt   5700

tccctctctt ttttttgtca aaagcccaga gactgacaac cagctgcagt gtctaagtgt   5760

tcctcactga cagggtgggg cctcaccacc cctggaggga gcagcgttgg cagggagaca   5820

gcctggccca gtgaccctgg gcccaagcca gcccctccag ggctttcagg gaagcgccat   5880

ccattttcaa agatgtcaaa cgtcacttct tcctgtaggg cccgagtcct gcctcctatc   5940

agggccagat catagaaggc tattttctat tctggggaac gattataact taaatgattg   6000

ttttaataaa aattctaagc tggaaaataa aaaaaaaaaa aaaaaa                 6046
```

<210> SEQ ID NO 2
<211> LENGTH: 1788
<212> TYPE: DNA
<213> ORGANISM: homo sapiens

<400> SEQUENCE: 2
atggccgggg ccatcgcttc ccgcatgagc ttcagctctc tcaagaggaa gcaacccaag 60
acgttcaccg tgaggatcgt caccatggac gccgagatgg agttcaattg cgagatgaag 120
tggaaaggga aggacctctt tgatttggtg tgccggactc tggggctccg agaaacctgg 180
ttctttggac tgcagtacac aatcaaggac acagtggcct ggctcaaaat ggacaagaag 240
gtactggatc atgatgtttc aaaggaagaa ccagtcacct ttcacttctt ggccaaattt 300
tatcctgaga atgctgaaga ggagctggtt caggagatca cacaacattt attcttctta 360
caggtaaaga agcagatttt agatgaaaag atctactgcc ctcctgaggc ttctgtgctc 420
ctggcttctt acgccgtcca ggccaagtat ggtgactacg accccagtgt tcacaagcgg 480
ggatttttgg cccaagagga attgcttcca aaaagggtaa taaatctgta tcagatgact 540
ccggaaatgt gggaggagag aattactgct tggtacgcag agcaccgagg ccgagccagg 600
gatgaagctg aaatggaata tctgaagata gctcaggacc tggagatgta cggtgtgaac 660
tactttgcaa tccggaataa aaagggcaca gagctgctgc ttggagtgga tgccctgggg 720
cttcacattt atgaccctga gaacagactg acccccaaga tctccttccc gtggaatgaa 780
atccgaaaca tctcgtacag tgacaaggag tttactatta aaccactgga taagaaaatt 840
gatgtcttca agtttaactc ctcaaagctt cgtgttaata agctgattct ccagctatgt 900
atcgggaacc atgatctatt tatgaggaga aggaaagccg attctttgga agttcagcag 960
atgaaagccc aggccaggga ggagaaggct agaaagcaga tggagcggca gcgcctcgct 1020
cgagagaagc agatgaggga ggaggctgaa cgcacgaggg atgagttgga gaggaggctg 1080
ctgcagatga aagaagaagc aacaatggcc aacgaagcac tgatgcggtc tgaggagaca 1140
gctgacctgt tggctgaaaa ggcccagatc accgaggagg aggcaaaact tctggcccag 1200
aaggccgcag aggctgagca ggaaatgcag cgcatcaagg ccacagcgat tcgcacggag 1260
gaggagaagc gcctgatgga gcagaaggtg ctggaagccg aggtgctggc actgaagatg 1320
gctgaggagt cagagaggag ggccaaagag gcagatcagc tgaagcagga cctgcaggaa 1380
gcacgcgagg cggagcgaag agccaagcag aagctcctgg agattgccac caagcccacg 1440
tacccgccca tgaacccaat tccagcaccg ttgcctcctg acataccaag cttcaacctc 1500
attggtgaca gcctgtcttt cgacttcaaa gatactgaca tgaagcggct ttccatggag 1560
atagagaaag aaaaagtgga atacatggaa aagagcaagc atctgcagga gcagctcaat 1620
gaactcaaga cagaaatcga ggccttgaaa ctgaaagaga gggagacagc tctggatatt 1680
ctgcacaatg agaactccga caggggtggc agcagcaagc acaataccat taaaaagctc 1740
accttgcaga gcgccaagtc ccgagtggcc ttctttgaag agctctag 1788

<210> SEQ ID NO 3
<211> LENGTH: 595
<212> TYPE: PRT
<213> ORGANISM: Homo sapiens

<400> SEQUENCE: 3

Met Ala Gly Ala Ile Ala Ser Arg Met Ser Phe Ser Ser Leu Lys Arg
1 5 10 15

Lys Gln Pro Lys Thr Phe Thr Val Arg Ile Val Thr Met Asp Ala Glu
20 25 30

Met Glu Phe Asn Cys Glu Met Lys Trp Lys Gly Lys Asp Leu Phe Asp
35 40 45

-continued

```
Leu Val Cys Arg Thr Leu Gly Leu Arg Glu Thr Trp Phe Phe Gly Leu
    50                  55                  60

Gln Tyr Thr Ile Lys Asp Thr Val Ala Trp Leu Lys Met Asp Lys Lys
65                  70                  75                  80

Val Leu Asp His Asp Val Ser Lys Glu Glu Pro Val Thr Phe His Phe
                85                  90                  95

Leu Ala Lys Phe Tyr Pro Glu Asn Ala Glu Glu Glu Leu Val Gln Glu
            100                 105                 110

Ile Thr Gln His Leu Phe Phe Leu Gln Val Lys Lys Gln Ile Leu Asp
        115                 120                 125

Glu Lys Ile Tyr Cys Pro Pro Glu Ala Ser Val Leu Leu Ala Ser Tyr
    130                 135                 140

Ala Val Gln Ala Lys Tyr Gly Asp Tyr Asp Pro Ser Val His Lys Arg
145                 150                 155                 160

Gly Phe Leu Ala Gln Glu Glu Leu Leu Pro Lys Arg Val Ile Asn Leu
                165                 170                 175

Tyr Gln Met Thr Pro Glu Met Trp Glu Glu Arg Ile Thr Ala Trp Tyr
            180                 185                 190

Ala Glu His Arg Gly Arg Ala Arg Asp Glu Ala Glu Met Glu Tyr Leu
        195                 200                 205

Lys Ile Ala Gln Asp Leu Glu Met Tyr Gly Val Asn Tyr Phe Ala Ile
    210                 215                 220

Arg Asn Lys Lys Gly Thr Glu Leu Leu Leu Gly Val Asp Ala Leu Gly
225                 230                 235                 240

Leu His Ile Tyr Asp Pro Glu Asn Arg Leu Thr Pro Lys Ile Ser Phe
                245                 250                 255

Pro Trp Asn Glu Ile Arg Asn Ile Ser Tyr Ser Asp Lys Glu Phe Thr
            260                 265                 270

Ile Lys Pro Leu Asp Lys Lys Ile Asp Val Phe Lys Phe Asn Ser Ser
        275                 280                 285

Lys Leu Arg Val Asn Lys Leu Ile Leu Gln Leu Cys Ile Gly Asn His
    290                 295                 300

Asp Leu Phe Met Arg Arg Arg Lys Ala Asp Ser Leu Glu Val Gln Gln
305                 310                 315                 320

Met Lys Ala Gln Ala Arg Glu Glu Lys Ala Arg Lys Gln Met Glu Arg
                325                 330                 335

Gln Arg Leu Ala Arg Glu Lys Gln Met Arg Glu Glu Ala Glu Arg Thr
            340                 345                 350

Arg Asp Glu Leu Glu Arg Arg Leu Leu Gln Met Lys Glu Glu Ala Thr
        355                 360                 365

Met Ala Asn Glu Ala Leu Met Arg Ser Glu Glu Thr Ala Asp Leu Leu
    370                 375                 380

Ala Glu Lys Ala Gln Ile Thr Glu Glu Glu Ala Lys Leu Leu Ala Gln
385                 390                 395                 400

Lys Ala Ala Glu Ala Glu Gln Glu Met Gln Arg Ile Lys Ala Thr Ala
                405                 410                 415

Ile Arg Thr Glu Glu Glu Lys Arg Leu Met Glu Gln Lys Val Leu Glu
            420                 425                 430

Ala Glu Val Leu Ala Leu Lys Met Ala Glu Glu Ser Glu Arg Arg Ala
        435                 440                 445

Lys Glu Ala Asp Gln Leu Lys Gln Asp Leu Gln Glu Ala Arg Glu Ala
    450                 455                 460

Glu Arg Arg Ala Lys Gln Lys Leu Leu Glu Ile Ala Thr Lys Pro Thr
```

```
465                 470                 475                 480

Tyr Pro Pro Met Asn Pro Ile Pro Ala Pro Leu Pro Pro Asp Ile Pro
                485                 490                 495

Ser Phe Asn Leu Ile Gly Asp Ser Leu Ser Phe Asp Phe Lys Asp Thr
            500                 505                 510

Asp Met Lys Arg Leu Ser Met Glu Ile Glu Lys Glu Lys Val Glu Tyr
        515                 520                 525

Met Glu Lys Ser Lys His Leu Gln Glu Gln Leu Asn Glu Leu Lys Thr
    530                 535                 540

Glu Ile Glu Ala Leu Lys Leu Lys Glu Arg Glu Thr Ala Leu Asp Ile
545                 550                 555                 560

Leu His Asn Glu Asn Ser Asp Arg Gly Gly Ser Ser Lys His Asn Thr
                565                 570                 575

Ile Lys Lys Leu Thr Leu Gln Ser Ala Lys Ser Arg Val Ala Phe Phe
            580                 585                 590

Glu Glu Leu
        595


<210> SEQ ID NO 4
<211> LENGTH: 8789
<212> TYPE: DNA
<213> ORGANISM: Homo sapiens

<400> SEQUENCE: 4

atgctcagtg gcttctcgac aagttggcag caacaacacg gccctggtcg tcgtcgccgc      60

tgcggtaacg gagcggtttg ggtggcggag cctgcgttcg cgccttcccg ctctcctcgg     120

gaggcccttc ctgctctccc ctaggctccg cggccgccca gggggtggga gcgggtgagg     180

ggagccaggc gcccagcgag agaggccccc cgccgcaggg cggcccggga gctcgaggcg     240

gtccggcccg cgcgggcagc ggcgcggcgc tgaggagggg cggcctggcc gggacgcctc     300

ggggcggggg ccgaggagct ctccgggccg ccggggaaag ctacgggccc ggtgcgtccg     360

cggaccagca gcgcgggaga gcggactccc ctcgccaccg cccgagccca ggttatcctg     420

aatacatgtc taacaatttt ccttgcaacg ttagctgttg tttttcactg tttccaaagg     480

atcaaaattg cttcagaaat tggagacata tttgatttaa aaggaaaaac ttgaacaaat     540

ggacaatatg tctattacga atacaccaac aagtaatgat gcctgtctga gcattgtgca     600

tagtttgatg tgccatagac aaggtggaga gagtgaaaca tttgcaaaaa gagcaattga     660

aagtttggta aagaagctga aggagaaaaa agatgaattg gattctttaa taacagctat     720

aactacaaat ggagctcatc ctagtaaatg tgttaccata cagagaacat tggatgggag     780

gcttcaggtg gctggtcgga aaggatttcc tcatgtgatc tatgcccgtc tctggaggtg     840

gcctgatctt cacaaaaatg aactaaaaca tgttaaatat tgtcagtatg cgtttgactt     900

aaaatgtgat agtgtctgtg tgaatccata tcactacgaa cgagttgtat cacctggaat     960

tgatctctca ggattaacac tgcagagtaa tgctccatca agtatgatgg tgaaggatga    1020

atatgtgcat gactttgagg gacagccatc gttgtccact gaaggacatt caattcaaac    1080

catccagcat ccaccaagta atcgtgcatc gacagagaca tacagcaccc cagctctgtt    1140

agccccatct gagtctaatg ctaccagcac tgccaacttt cccaacattc ctgtggcttc    1200

cacaagtcag cctgccagta tactgggggg cagccatagt gaaggactgt tgcagatagc    1260

atcagggcct cagccaggac agcagcagaa tggatttact ggtcagccag ctacttacca    1320

tcataacagc actaccacct ggactggaag taggactgca ccatacacac ctaatttgcc    1380
```

```
tcaccaccaa aacggccatc ttcagcacca cccgcctatg ccgccccatc ccggacatta   1440
ctggcctgtt cacaatgagc ttgcattcca gcctcccatt tccaatcatc ctgctcctga   1500
gtattggtgt tccattgctt actttgaaat ggatgttcag gtaggagaga catttaaggt   1560
tccttcaagc tgccctattg ttactgttga tggatacgtg gacccttctg gaggagatcg   1620
cttttgtttg ggtcaactct ccaatgtcca caggacagaa gccattgaga gagcaaggtt   1680
gcacataggc aaaggtgtgc agttggaatg taaaggtgaa ggtgatgttt gggtcaggtg   1740
ccttagtgac cacgcggtct ttgtacagag ttactactta gacagagaag ctgggcgtgc   1800
acctggagat gctgttcata agatctaccc aagtgcatat ataaaggtct ttgatttgcg   1860
tcagtgtcat cgacagatgc agcagcaggc ggctactgca caagctgcag cagctgccca   1920
ggcagcagcc gtggcaggaa acatccctgg cccaggatca gtaggtggaa tagctccagc   1980
tatcagtctg tcagctgctg ctggaattgg tgttgatgac cttcgtcgct tatgcatact   2040
caggatgagt tttgtgaaag gctggggacc ggattaccca agacagagca tcaaagaaac   2100
accttgctgg attgaaattc acttacaccg ggccctccag ctcctagacg aagtacttca   2160
taccatgccg attgcagacc cacaaccttt agactgaggt cttttaccgt tggggccctt   2220
aaccttatca ggatggtgga ctacaaaata caatcctgtt tataatctga agatatattt   2280
cacttttgtt ctgctttatc ttttcataaa gggttgaaaa tgtgtttgct gccttgctcc   2340
tagcagacag aaactggatt aaaacaattt tttttttcct cttcagaact tgtcaggcat   2400
ggctcagagc ttgaagatta ggagaaacac attcttatta attcttcacc tgttatgtat   2460
gaaggaatca ttccagtgct agaaaattta gccctttaaa acgtcttaga gccttttatc   2520
tgcagaacat cgatatgtat atcattctac agaataatcc agtattgctg attttaaagg   2580
cagagaagtt ctcaaagtta attcacctat gttattttgt gtacaagttg ttattgttga   2640
acatacttca aaaataatgt gccatgtggg tgagttaatt ttaccaagag taactttact   2700
ctgtgtttaa aaagtaagtt aataatgtat tgtaatcttt catccaaaat atttttttgca   2760
agttatatta gtgaagatgg tttcaattca gattgtcttg caacttcagt tttatttttg   2820
ccaaggcaaa aaactcttaa tctgtgtgta tattgagaat cccttaaaat taccagacaa   2880
aaaaatttaa aattacgttt gttattccta gtggatgact gttgatgaag tatacttttc   2940
ccctgttaaa cagtagttgt attcttctgt atttctaggc acaaggttgg ttgctaagaa   3000
gcctataaga ggaatttctt ttccttcatt catagggaaa ggttttgtat tttttaaaac   3060
actaaaagca gcgtcactct acctaatgtc tcactgttct gcaaaggtgg caatgcttaa   3120
actaaataat gaataaactg aatattttgg aaactgctaa attctatgtt aaatactgtg   3180
cagaataatg gaaacattac agttcataat aggtagtttg gatatttttg tacttgattt   3240
gatgtgactt tttttggtat aatgtttaaa tcatgtatgt tatgatattg tttaaaattc   3300
agtttttgta tcttggggca agactgcaaa ctttttttata tcttttggtt attctaagcc   3360
ctttgccatc aatgatcata tcaattggca gtgactttgt atagagaatt taagtagaaa   3420
agttgcagat gtattgactg taccacagac acaatatgta tgctttttac ctagctggta   3480
gcataaataa aactgaatct caacatacaa agttgaattc taggtttgat ttttaagatt   3540
tttttttttct tttgcacttt tgagtccaat ctcagtgatg aggtaccttc tactaaatga   3600
caggcaacag ccagttctat tgggcagctt tgttttttttc cctcacactc taccgggact   3660
tccccatgga cattgtgtat catgtgtaga gttggttttt tttttttta attttttattt   3720
```

-continued

```
tactatagca gaaatagacc tgattatcta caagatgata aatagattgt ctacaggata   3780
aatagtatga aataaaatca aggattatct ttcagatgtg tttacttttg cctggagaac   3840
ttttagctat agaaacactt gtgtgatgat agtcctcctt atatcacctg gaatgaacac   3900
agcttctact gccttgctca gaaggtcttt taaatagacc atcctagaaa ccactgagtt   3960
tgcttatttc tgtgatttaa acatagatct tgatccaagc tacatgactt ttgtctttaa   4020
ataacttatc taccacctca tttgtactct tgattactta caaattcttt cagtaaacac   4080
ctaattttct tctgtaaaag tttggtgatt taagttttat tggcagtttt ataaaaagac   4140
atcttctcta gaaattgcta actttaggtc cattttactg tgaatgagga ataggagtga   4200
gttttagaat aacagatttt taaaaatcca gatgatttga ttaaaacctt aatcatacat   4260
tgacataatt cattgcttct ttttttgag atatggagtc ttgctgtgtt gcccaggcag   4320
gagtgcagtg gtatgatctc agctcactgc aacctctgcc tcccgggttc aactgattct   4380
cctgcctcag cctccctggt agctaggatt acaggtgccc gccaccatgc ctggctaact   4440
tttgtagttt tagtagagac ggggttttgc ctgttggcca ggctggtctt gaactcctga   4500
cctcaagtga tccatccacc ttggcctccc aaagtgctgg gattacgggc gtgagccact   4560
gtccctggcc tcattgttcc cttttctact ttaaggaaag ttttcatgtt taatcatctg   4620
gggaaagtat gtgaaaaata tttgttaaga agtatctctt tggagccaag ccacctgtct   4680
tggtttcttt ctactaagag ccataaagta tagaaatact tctagttgtt aagtgcttat   4740
atttgtacct agatttagtc acacgctttt gagaaaacat ctagtatgtt atgatcagct   4800
attcctgaga gcttggttgt taatctatat ttctatttct tagtggtagt catctttgat   4860
gaataagact aaagattctc acaggtttaa aattttatgt ctactttaag ggtaaaatta   4920
tgaggttatg gttctgggtg ggttttctct agctaattca tatctcaaag agtctcaaaa   4980
tgttgaattt cagtgcaagc tgaatgagag atgagccatg tacacccacc gtaagacctc   5040
attccatgtt tgtccagtgc ctttcagtgc attatcaaag ggaatccttc atggtgttgc   5100
ctttatttc cggggagtag atcgtgggat atagtctatc tcatttttaa tagtttaccg    5160
cccctggtat acaaagataa tgacaataaa tcactgccat ataaccttgc tttttccaga   5220
aacatggctg ttttgtattg ctgtaaccac taaataggtt gcctatacca ttcctcctgt   5280
gaacagtgca gatttacagg ttgcatggtc tggcttaagg agagccatac ttgagacatg   5340
tgagtaaact gaactcatat tagctgtgct gcatttcaga cttaaaatcc atttttgtgg   5400
ggcagggtgt ggtgtgtaaa ggggggtgtt tgtaatacaa gttgaaggca aaataaaatg   5460
tcctgtctcc cagatgatat acatcttatt atttttaaag tttattgcta attgtaggaa   5520
ggtgagttgc aggtatcttt gactatggtc atctggggaa ggaaaatttt acattttact   5580
attaatgctc cttaagtgtc tatggaggtt aaagaataaa atggtaaatg tttctgtgcc   5640
tggtttgatg gtaactggtt aatagttact caccatttta tgcagagtca cattagttca   5700
cacccttttct gagagccttt tgggagaagc agttttattc tctgagtgga acagagttct   5760
ttttgttgat aatttctagt ttgctccctt cgttattgcc aactttactg gcattttatt   5820
taatgatagc agattgggaa aatggcaaat ttaggttacg gaggtaaatg agtatatgaa   5880
agcaattacc tctaaagcca gttaacaatt attttgtagg tggggtacac tcagcttaaa   5940
gtaatgcatt tttttttccc gtaaaggcag aatccatctt gttgcagata gctatctaaa   6000
taatctcata tcctcttttg caaagactac agagaatagg ctatgacaat cttgttcaag   6060
cctttccatt tttttccctg ataactaagt aatttctttg aacataccaa gaagtatgta   6120
```

-continued

```
aaaagtccat ggccttattc atccacaaag tggcatccta ggcccagcct tatccctagc   6180
agttgtccca gtgctgctag gttgcttatc ttgtttatct ggaatcactg tggagtgaaa   6240
ttttccacat catccagaat tgccttattt aagaagtaaa acgttttaat ttttagcctt   6300
tttttggtgg agttatttaa tatgtatatc agaggatata ctagatggta acatttcttt   6360
ctgtgcttgg ctatctttgt ggacttcagg ggcttctaaa acagacagga ctgtgttgcc   6420
tttactaaat ggtctgagac agctatggtt ttgaattttt agtttttttt ttttaaccca   6480
cttcccctcc tggtctcttc cctctctgat aattaccatt catatgtgag tgttagtgtg   6540
cctcctttta gcattttctt cttctctttc tgattcttca tttctgactg cctaggcaag   6600
gaaaccagat aaccaaactt actagaacgt tctttaaaac acaagtacaa actctgggac   6660
aggacccaag acactttcct gtgaagtgct gaaaaagacc tcattgtatt ggcatttgat   6720
atcagtttga tgtagcttag agtgcttcct gattcttgct gagtttcagg tagttgagat   6780
agagagaagt gagtcatatt catattttcc cccttagaat aatattttga aaggtttcat   6840
tgcttccact tgaatgctgc tcttacaaaa actggggtta caagggttac taaattagca   6900
tcagtagcca gaggcaatac cgttgtctgg aggacaccag caaacaacac acaacaaagc   6960
aaaacaaacc ttgggaaact aaggccattt gttttgtttt ggtgtcccct ttgaagccct   7020
gccttctggc cttactcctg tacagatatt tttgacctat aggtgccttt atgagaattg   7080
agggtctgac atcctgcccc aaggagtagc taaagtaatt gctagtgttt tcagggattt   7140
taacatcaga ctggaatgaa tgaatgaaac tttttgtcct tttttttct gttttttttt   7200
ttctaatgta gtaaggacta aggaaaacct ttggtgaaga caatcatttc tctctgttga   7260
tgtggatact tttcacaccg tttatttaaa tgctttctca ataggtccag agccagtgtt   7320
cttgttcaac ctgaaagtaa tggctctggg ttgggccaga cagttgcact ctctagtttg   7380
ccctctgcca caaatttgat gtgtgacctt tgggcaagtc atttatcttc tctgggcctt   7440
agttgcctca tctgtaaaat gagggagttg gagtagatta attattccag ctctgaaatt   7500
ctaagtgacc ttggctacct tgcagcagtt ttggatttct tccttatctt tgttctgctg   7560
tttgaggggg ctttttactt atttccatgt tattcaaagg agactaggct tgatatttta   7620
ttactgttct tttatggaca aaaggttaca tagtatgccc ttaagactta attttaacca   7680
aaggcctagc accaccttag gggctgcaat aaacacttaa cgcgcgtgcg cacgcgcgcg   7740
cgcacacaca cacacacaca cacacacaca cacaggtcag agtttaaggc tttcgagtca   7800
tgacattcta gcttttgaat tgcgtgcaca cacacacgca cgcacacact ctggtcagag   7860
tttattaagg ctttcgagtc atgacattat agcttttgag ttggtgtgtg tgacaccacc   7920
ctcctaagtg gtgtgtgctt gtaatttttt ttttcagtga aaatggattg aaaacctgtt   7980
gttaatgctt agtgatatta tgctcaaaac aaggaaattc ccttgaaccg tgtcaattaa   8040
actggtttat atgactcaag aaaacaatac cagtagatga ttattaactt tattcttggc   8100
tctttttagg tccattttga ttaagtgact tttggctgga tcattcagag ctctcttcta   8160
gcctaccctt ggatgagtac aattaatgaa attcatattt tcaaggacct gggagccttc   8220
cttggggctg ggttgagggt ggggggttgg ggagtcctgg tagaggccag ctttgtggta   8280
gctggagagg aagggatgaa accagctgct gttgcaaagg ctgcttgtca ttgatagaag   8340
gactcacggg cttggattga ttaagactaa acatggagtt ggcaaacttt cttcaagtat   8400
tgagttctgt tcaatgcatt ggacatgtga tttaagggaa aagtgtgaat gcttatagat   8460
```

```
gatgaaaacc tggtgggctg cagagcccag tttagaagaa gtgagttggg ggttggggac   8520

agatttggtg gtggtatttc ccaactgttt cctcccctaa attcagagga atgcagctat   8580

gccagaagcc agagaagagc cactcgtagc ttctgctttg ggacaactg gtcagttgaa    8640

agtcccagga gttcctttgt ggctttctgt atacttttgc ctggttaaag tctgtggcta   8700

aaaaatagtc gaacctttct tgagaactct gtaacaaagt atgtttttga ttaaaagaga   8760

aagccaacta aaaaaaaaaa aaaaaaaaa                                      8789


<210> SEQ ID NO 5
<211> LENGTH: 1659
<212> TYPE: DNA
<213> ORGANISM: Homo sapiens

<400> SEQUENCE: 5

atggacaata tgtctattac gaatacacca acaagtaatg atgcctgtct gagcattgtg     60

catagtttga tgtgccatag acaaggtgga gagagtgaaa catttgcaaa aagagcaatt    120

gaaagtttgg taaagaagct gaaggagaaa aaagatgaat tggattcttt aataacagct    180

ataactacaa atggagctca tcctagtaaa tgtgttacca tacagagaac attggatggg    240

aggcttcagg tggctggtcg gaaaggattt cctcatgtga tctatgcccg tctctggagg    300

tggcctgatc ttcacaaaaa tgaactaaaa catgttaaat attgtcagta tgcgtttgac    360

ttaaaatgtg atagtgtctg tgtgaatcca tatcactacg aacgagttgt atcacctgga    420

attgatctct caggattaac actgcagagt aatgctccat caagtatgat ggtgaaggat    480

gaatatgtgc atgactttga gggacagcca tcgttgtcca ctgaaggaca ttcaattcaa    540

accatccagc atccaccaag taatcgtgca tcgacagaga catacagcac cccagctctg    600

ttagccccat ctgagtctaa tgctaccagc actgccaact ttcccaacat tcctgtggct    660

tccacaagtc agcctgccag tatactgggg ggcagcccata gtgaaggact gttgcagata   720

gcatcagggc ctcagccagg acagcagcag aatggattta ctggtcagcc agctacttac    780

catcataaca gcactaccac ctggactgga agtaggactg caccatacac acctaatttg    840

cctcaccacc aaaacggcca tcttcagcac cacccgccta tgccgcccca tcccggacat    900

tactggcctg ttcacaatga gcttgcattc cagcctccca tttccaatca tcctgctcct    960

gagtattggt gttccattgc ttactttgaa atggatgttc aggtaggaga gacatttaag   1020

gttccttcaa gctgccctat tgttactgtt gatggatacg tggacccttc tggaggagat   1080

cgcttttgtt tgggtcaact ctccaatgtc cacaggacag aagccattga gagagcaagg   1140

ttgcacatag gcaaaggtgt gcagttggaa tgtaaaggtg aaggtgatgt ttgggtcagg   1200

tgccttagtg accacgcggt ctttgtacag agttactact tagacagaga agctgggcgt   1260

gcacctggag atgctgttca taagatctac ccaagtgcat atataaaggt ctttgatttg   1320

cgtcagtgtc atcgacagat gcagcagcag gcggctactg cacaagctgc agcagctgcc   1380

caggcagcag ccgtggcagg aaacatccct ggcccaggat cagtaggtgg aatagctcca   1440

gctatcagtc tgtcagctgc tgctggaatt ggtgttgatg accttcgtcg cttatgcata   1500

ctcaggatga gttttgtgaa aggctgggga ccggattacc caagacagag catcaaagaa   1560

acaccttgct ggattgaaat tcacttacac cgggccctcc agctcctaga cgaagtactt   1620

cataccatgc cgattgcaga cccacaacct ttagactga                          1659


<210> SEQ ID NO 6
<211> LENGTH: 552
```

<212> TYPE: PRT
<213> ORGANISM: Homo sapiens

<400> SEQUENCE: 6

```
Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
                165                 170                 175

His Ser Ile Gln Thr Ile Gln His Pro Pro Ser Asn Arg Ala Ser Thr
            180                 185                 190

Glu Thr Tyr Ser Thr Pro Ala Leu Leu Ala Pro Ser Glu Ser Asn Ala
        195                 200                 205

Thr Ser Thr Ala Asn Phe Pro Asn Ile Pro Val Ala Ser Thr Ser Gln
    210                 215                 220

Pro Ala Ser Ile Leu Gly Gly Ser His Ser Glu Gly Leu Leu Gln Ile
225                 230                 235                 240

Ala Ser Gly Pro Gln Pro Gly Gln Gln Gln Asn Gly Phe Thr Gly Gln
                245                 250                 255

Pro Ala Thr Tyr His His Asn Ser Thr Thr Thr Trp Thr Gly Ser Arg
            260                 265                 270

Thr Ala Pro Tyr Thr Pro Asn Leu Pro His His Gln Asn Gly His Leu
        275                 280                 285

Gln His His Pro Pro Met Pro Pro His Pro Gly His Tyr Trp Pro Val
    290                 295                 300

His Asn Glu Leu Ala Phe Gln Pro Pro Ile Ser Asn His Pro Ala Pro
305                 310                 315                 320

Glu Tyr Trp Cys Ser Ile Ala Tyr Phe Glu Met Asp Val Gln Val Gly
                325                 330                 335

Glu Thr Phe Lys Val Pro Ser Ser Cys Pro Ile Val Thr Val Asp Gly
            340                 345                 350

Tyr Val Asp Pro Ser Gly Gly Asp Arg Phe Cys Leu Gly Gln Leu Ser
        355                 360                 365

Asn Val His Arg Thr Glu Ala Ile Glu Arg Ala Arg Leu His Ile Gly
    370                 375                 380

Lys Gly Val Gln Leu Glu Cys Lys Gly Glu Gly Asp Val Trp Val Arg
385                 390                 395                 400
```

```
Cys Leu Ser Asp His Ala Val Phe Val Gln Ser Tyr Tyr Leu Asp Arg
                405                 410                 415

Glu Ala Gly Arg Ala Pro Gly Asp Ala Val His Lys Ile Tyr Pro Ser
            420                 425                 430

Ala Tyr Ile Lys Val Phe Asp Leu Arg Gln Cys His Arg Gln Met Gln
        435                 440                 445

Gln Gln Ala Ala Thr Ala Gln Ala Ala Ala Ala Ala Gln Ala Ala Ala
    450                 455                 460

Val Ala Gly Asn Ile Pro Gly Pro Gly Ser Val Gly Gly Ile Ala Pro
465                 470                 475                 480

Ala Ile Ser Leu Ser Ala Ala Ala Gly Ile Gly Val Asp Asp Leu Arg
                485                 490                 495

Arg Leu Cys Ile Leu Arg Met Ser Phe Val Lys Gly Trp Gly Pro Asp
            500                 505                 510

Tyr Pro Arg Gln Ser Ile Lys Glu Thr Pro Cys Trp Ile Glu Ile His
        515                 520                 525

Leu His Arg Ala Leu Gln Leu Leu Asp Glu Val Leu His Thr Met Pro
    530                 535                 540

Ile Ala Asp Pro Gln Pro Leu Asp
545                 550


<210> SEQ ID NO 7
<211> LENGTH: 5778
<212> TYPE: DNA
<213> ORGANISM: Homo sapiens

<400> SEQUENCE: 7

gtgacacaat tacaacaact ttgtgctggt gccggggaag tttgtgtctc caacgaatcc     60

cctcagtgct ccccagcccc gcgcgctccg gccgttcccg ccgtccccgc ctgtggctgc    120

cccctgccca accccgcgat gtgaccctac agccgaaagc cgccgctgcc gacccggggg    180

ctccgcagcc cctgccgccg ccgccgccgc cttcaccgcc gccgcgttgg gatttttcgt    240

cgccgccgcc cgcggcggag gaggaggcgg cgataaagtt ggtgtgctgg tcccgcgcgc    300

agattggggg cgtcactgcg ggccccggtc cgaggggggg tgtcggcgtt ggagttgtga    360

attcgctgcg tttccatgaa atcctgcgga gtgtcgctcg ctaccgccgc cgctgccgcc    420

gccgctttcg gtgatgagga aaagaaaatg gcggcgggaa aagcgagcgg cgagagcgag    480

gaggcgtccc ccagcctgac agccgaggag agggaggcgc tcggcggact ggacagccgc    540

ctctttgggt tcgtgagatt tcatgaagat ggcgccagga cgaaggccct actgggcaag    600

gctgttcgct gctatgaatc tctaatctta aaagctgaag gaaaagtgga gtctgatttc    660

ttttgtcaat taggtcactt caacctctta ttggaagatt atccaaaagc attatctgca    720

taccagaggt actacagttt acagtctgac tactggaaga atgctgcctt tttatatggt    780

cttggtttgg tctacttcca ttataatgca tttcagtggg caattaaagc atttcaggag    840

gtgctttatg ttgatcccag cttttgtcga gccaaggaaa ttcatttacg acttgggctt    900

atgttcaaag tgaacacaga ctatgagtct agtttaaagc attttcagtt agctttggtt    960

gactgtaatc cctgcacttt gtccaatgct gaaattcaat ttcacattgc ccacttatat   1020

gaaacccaga ggaaatatca ttctgcaaaa gaagcttatg aacaactttt gcagacagag   1080

aatctttctg cacaagtaaa agcaactgtc ttacaacagt taggttggat gcatcacact   1140

gtagatctcc tgggagataa agccaccaag gaaagctatg ctattcagta tctccaaaag   1200
```

-continued

```
tccttggaag cagatcctaa ttctggccag tcctggtatt tcctcggaag gtgctattca   1260
agtattggga aagttcagga tgcctttata tcttacaggc agtctattga taaatcagaa   1320
gcaagtgcag atacatggtg ttcaataggt gtgctatatc agcagcaaaa tcagcccatg   1380
gatgctttac aggcctatat ttgtgctgta caattggacc atggccatgc tgcagcctgg   1440
atggacctag gcactctcta tgaatcctgc aaccagcctc aggatgccat taaatgctac   1500
ttaaatgcaa ctagaagcaa aagttgtagt aatacctctg cacttgcagc acgaattaag   1560
tatttacagg ctcagttgtg taaccttcca caaggtagtc tacagaataa aactaaatta   1620
cttcctagta ttgaggaggc gtggagccta ccaattcccg cagagcttac ctccaggcag   1680
ggtgccatga acacagcaca gcagaatact tctgacaatt ggagtggtgg acatgctgtg   1740
tcacatcctc cagtacagca acaagctcat tcatggtgtt tgacaccaca gaaattacag   1800
catttggaac agctccgcgc aaatagaaat aatttaaatc cagcacagaa actgatgctg   1860
gaacagctgg aaagtcagtt tgtcttaatg caacaacacc aaatgagacc aacaggagtt   1920
gcacaggtac gatctactgg aattcctaat gggccaacag ctgactcatc actgcctaca   1980
aactcagtct ctggccagca gccacagctt gctctgacca gagtgcctag cgtctctcag   2040
cctggagtcc gtcctgcctg ccctgggcag cctttggcca atggaccctt ttctgcaggc   2100
catgttccct gtagcacatc aagaacgctg ggaagtacag acactatttt gataggcaat   2160
aatcatataa caggaagtgg aagtaatgga aacgtgcctt acctgcagcg aaacgcactc   2220
actctacctc ataaccgcac aaacctgacc agcagcgcag aggagccgtg gaaaaaccaa   2280
ctatctaact ccactcaggg gcttcacaaa ggtcagagtt cacattcggc aggtcctaat   2340
ggtgaacgac ctctctcttc cactgggcct tcccagcatc tccaggcagc tggctctggt   2400
attcagaatc agaacggaca tcccaccctg cctagcaatt cagtaacaca gggggctgct   2460
ctcaatcacc tctcctctca cactgctacc tcaggtggac aacaaggcat taccttaacc   2520
aaagagagca agccttcagg aaacatattg acggtgcctg aaacaagcag gcacactgga   2580
gagacaccta acagcactgc cagtgtcgag ggacttccta atcatgtcca tcagatgacg   2640
gcagatgctg tttgcagtcc tagccatgga gattctaagt caccaggttt actaagttca   2700
gacaatcctc agctctctgc cttgttgatg ggaaaagcca ataacaatgt gggtactgga   2760
acctgtgaca aagtcaataa catccaccca gctgttcata caaagactga taactctgtt   2820
gcctcttcac catcttcagc catttcaaca gcaacacctt ctccaaaatc cactgagcag   2880
acaaccacaa acagtgttac cagccttaac agccctcaca gtgggctaca cacaattaat   2940
ggagaaggga tggaagaatc tcagagcccc atgaaaacag atctgcttct ggttaaccac   3000
aaacctagtc cacagatcat accatcaatg tctgtgtcca tataccccag ctcagcagaa   3060
gttctgaagg catgcaggaa tctaggtaaa aatggcttat ctaacagtag cattttgttg   3120
gataaatgtc cacctccaag accaccatct tcaccatacc ctcccttgcc aaaggacaag   3180
ttgaatccac ctacacctag tatttacttg gaaaataaac gtgatgcttt ctttcctcca   3240
ttacatcaat tttgtacaaa tccgaacaac cctgttacag taatacgtgg ccttgctgga   3300
gctcttaagt tagacctggg acttttctct actaaaactt tggtggaagc taacaatgaa   3360
catatggtag aagtgaggac acagttgttg cagccagcag atgaaaactg ggatcccact   3420
ggaacaaaga aaatctggca ttgtgaaagt aatagatctc atactacaat tgctaaatat   3480
gcacagtacc aggcctcctc attccaggaa tcattgagag aagaaaatga aaaaagaagt   3540
catcataaag accactcaga tagtgaatct acatcgtcag ataattctgg gaggaggagg   3600
```

```
aaaggaccct ttaaaaccat aaagtttggg accaatattg acctatctga tgacaaaaag   3660
tggaagttgc agctacatga gctgactaaa cttcctgctt ttgtgcgtgt cgtatcagca   3720
ggaaatcttc taagccatgt tggtcatacc atattgggca tgaacacagt tcaactatac   3780
atgaaagttc cagggagcag aacaccaggt catcaggaaa ataacaactt ctgttcagtt   3840
aacataaata ttggcccagg tgactgtgaa tggtttgttg ttcctgaagg ttactggggt   3900
gttctgaatg acttctgtga aaaaaataat ttgaatttcc taatgggttc ttggtggccc   3960
aatcttgaag atctttatga agcaaatgtt ccagtgtata ggtttattca gcgacctgga   4020
gatttggtct ggataaatgc aggcactgtt cattgggttc aggctattgg ctggtgcaac   4080
aacattgctt ggaatgttgg tccacttaca gcctgccagt ataaattggc agtggaacgg   4140
tacgaatgga acaaattgca aagtgtgaag tcaatagtac ccatggttca tctttcctgg   4200
aatatggcac gaaatatcaa ggtctcagat ccaaagcttt ttgaaatgat taagtattgt   4260
cttctaagaa ctctgaagca atgtcagaca ttgagggaag ctctcattgc tgcaggaaaa   4320
gagattatat ggcatgggcg gacaaaagaa gaaccagctc attactgtag catttgtgaa   4380
gtggaggttt ttgatctgct ttttgtcact aatgagagta attcacgaaa gacctacata   4440
gtacattgcc aagattgtgc acgaaaaaca agcggaaact tggaaaactt tgtggtgcta   4500
gaacagtaca aaatggagga cctgatgcaa gtctatgacc aatttacatt agctcctcca   4560
ttaccatccg cctcatcttg atattgttcc atggacatta aatgagacct tttctgctat   4620
tcaggaaata acccagttct gcaccactgg tttttgtagc tatctcgtaa ggctgctggc   4680
tgaaaactgt gtctatgcaa ccttccaagt gcggagtgtc aaccaactgg acgggagaga   4740
gtactgctcc tactccagga ctctcacaaa gctgatgagc tgtacttcag aaaaaaataa   4800
taatttccat gttttgtata tatctgacaa aactggcaac atcttacaga ctactgactt   4860
gaagacaacc tcttttatat ttctctattt ctgggctgat gaatttgttt tcatctgtct   4920
tttcccccctt cagaattttc cttggaaaaa aaatactagc ctagctggtc atttctttgt   4980
aaggtagtta gcaattttaa gtctttcttt ggtcaacttt tttttaatgt gaaaagttag   5040
gtaagacact tttttactgc ttttatgttt ttctgtcttg ttttgagacc atgatggtta   5100
cacttttggt tcctaaataa aatttaaaaa attaacagcc aagtcacaaa ggtaatggat   5160
tgcacataga ctaaggaata aacttcagat ttgtgatttt tgtttctaat cttgatgtaa   5220
atttacacta tttataaata catatttatt gcttgaaaat atttgtgaat ggaatgctgt   5280
tatttttttcc agatttacct gccattgaaa ttttaaggag ttctgtaatt tcaaacacta   5340
ctcctattac attttctatg tgtaaataaa actgcttagc attgtacaga aacttttatt   5400
aaaattgttt aatgtttaaa gagttttcta ttgtttgagt tttaaaaaag actttatgta   5460
cagtgcccag tttttgttca tttttgaaat ctgattatat atattttata tatacttatg   5520
tatgtatata taatatatat agaaatctgg atatatatgt ataaatcttt agaacttaaa   5580
tttttctcgt tttaagtttc acatctatgg tagatttttg aggtgtctac tgtaaagtat   5640
tgcttacaaa aagtatgatt atttttaaag aaatatatat ggtatgtatc ctcaagacct   5700
aaaatgtcag actggtttat tgttaagttg caattactgc aatgacagac caataaacaa   5760
ttgctgccaa aaaaaaaa                                                 5778
```

<210> SEQ ID NO 8
<211> LENGTH: 4206
<212> TYPE: DNA

<213> ORGANISM: Homo sapiens

<400> SEQUENCE: 8
atgaaatcct gcggagtgtc gctcgctacc gccgccgctg ccgccgccgc tttcggtgat 60
gaggaaaaga aaatggcggc gggaaaagcg agcggcgaga gcgaggaggc gtcccccagc 120
ctgacagccg aggagaggga ggcgctcggc ggactggaca gccgcctctt tgggttcgtg 180
agatttcatg aagatggcgc caggacgaag gccctactgg gcaaggctgt tcgctgctat 240
gaatctctaa tcttaaaagc tgaaggaaaa gtggagtctg atttcttttg tcaattaggt 300
cacttcaacc tcttattgga agattatcca aaagcattat ctgcatacca gaggtactac 360
agtttacagt ctgactactg gaagaatgct gccttttat atggtcttgg tttggtctac 420
ttccattata atgcatttca gtgggcaatt aaagcatttc aggaggtgct ttatgttgat 480
cccagctttt gtcgagccaa ggaaattcat ttacgacttg ggcttatgtt caaagtgaac 540
acagactatg agtctagttt aaagcatttt cagttagctt tggttgactg taatccctgc 600
actttgtcca atgctgaaat tcaatttcac attgcccact tatatgaaac ccagaggaaa 660
tatcattctg caaaagaagc ttatgaacaa cttttgcaga cagagaatct ttctgcacaa 720
gtaaaagcaa ctgtcttaca acagttaggt tggatgcatc acactgtaga tctcctggga 780
gataaagcca ccaaggaaag ctatgctatt cagtatctcc aaaagtcctt ggaagcagat 840
cctaattctg gccagtcctg gtatttcctc ggaaggtgct attcaagtat tgggaaagtt 900
caggatgcct ttatatctta caggcagtct attgataaat cagaagcaag tgcagataca 960
tggtgttcaa taggtgtgct atatcagcag caaaatcagc ccatggatgc tttacaggcc 1020
tatatttgtg ctgtacaatt ggaccatggc catgctgcag cctggatgga cctaggcact 1080
ctctatgaat cctgcaacca gcctcaggat gccattaaat gctacttaaa tgcaactaga 1140
agcaaaagtt gtagtaatac ctctgcactt gcagcacgaa ttaagtattt acaggctcag 1200
ttgtgtaacc ttccacaagg tagtctacag aataaaacta aattacttcc tagtattgag 1260
gaggcgtgga gcctaccaat tcccgcagag cttacctcca ggcagggtgc catgaacaca 1320
gcacagcaga atacttctga caattggagt ggtggacatg ctgtgtcaca tcctccagta 1380
cagcaacaag ctcattcatg gtgtttgaca cccacagaaat tacagcattt ggaacagctc 1440
cgcgcaaata gaaataattt aaatccagca cagaaactga tgctggaaca gctggaaagt 1500
cagtttgtct taatgcaaca acaccaaatg agaccaacag gagttgcaca ggtacgatct 1560
actggaattc ctaatgggcc aacagctgac tcatcactgc ctacaaactc agtctctggc 1620
cagcagccac agcttgctct gaccagagtg cctagcgtct ctcagcctgg agtccgtcct 1680
gcctgccctg ggcagccttt ggccaatgga cccttttctg caggccatgt tccctgtagc 1740
acatcaagaa cgctgggaag tacagacact attttgatag gcaataatca tataacagga 1800
agtggaagta atggaaacgt gccttacctg cagcgaaacg cactcactct acctcataac 1860
cgcacaaacc tgaccagcag cgcagaggag ccgtggaaaa accaactatc taactccact 1920
caggggcttc acaaaggtca gagttcacat tcggcaggtc ctaatggtga acgacctctc 1980
tcttccactg ggccttccca gcatctccag gcagctggct ctggtattca gaatcagaac 2040
ggacatccca ccctgcctag caattcagta acacaggggg ctgctctcaa tcacctctcc 2100
tctcacactg ctacctcagg tggacaacaa ggcattacct taaccaaaga gagcaagcct 2160
tcaggaaaca tattgacggt gcctgaaaca agcaggcaca ctggagagac acctaacagc 2220
actgccagtg tcgagggact tcctaatcat gtccatcaga tgacggcaga tgctgtttgc 2280
agtcctagcc atggagattc taagtcacca ggtttactaa gttcagacaa tcctcagctc 2340
tctgccttgt tgatgggaaa agccaataac aatgtgggta ctggaacctg tgacaaagtc 2400
aataacatcc acccagctgt tcatacaaag actgataact ctgttgcctc ttcaccatct 2460
tcagccattt caacagcaac accttctcca aaatccactg agcagacaac cacaaacagt 2520
gttaccagcc ttaacagccc tcacagtggg ctacacacaa ttaatggaga agggatggaa 2580
gaatctcaga gccccatgaa aacagatctg cttctggtta accacaaacc tagtccacag 2640
atcataccat caatgtctgt gtccatatac cccagctcag cagaagttct gaaggcatgc 2700
aggaatctag gtaaaaatgg cttatctaac agtagcattt tgttggataa atgtccacct 2760
ccaagaccac catcttcacc ataccctccc ttgccaaagg acaagttgaa tccacctaca 2820
cctagtattt acttggaaaa taaacgtgat gctttctttc ctccattaca tcaattttgt 2880
acaaatccga acaaccctgt tacagtaata cgtggccttg ctggagctct taagttagac 2940
ctgggacttt tctctactaa aactttggtg gaagctaaca atgaacatat ggtagaagtg 3000
aggacacagt tgttgcagcc agcagatgaa aactgggatc ccactggaac aaagaaaatc 3060
tggcattgtg aaagtaatag atctcatact acaattgcta aatatgcaca gtaccaggcc 3120
tcctcattcc aggaatcatt gagagaagaa aatgaaaaaa gaagtcatca taaagaccac 3180
tcagatagtg aatctacatc gtcagataat tctgggagga ggaggaaagg accctttaaa 3240
accataaagt ttgggaccaa tattgaccta tctgatgaca aaaagtggaa gttgcagcta 3300
catgagctga ctaaacttcc tgcttttgtg cgtgtcgtat cagcaggaaa tcttctaagc 3360
catgttggtc ataccatatt gggcatgaac acagttcaac tatacatgaa agttccaggg 3420
agcagaacac caggtcatca ggaaaataac aacttctgtt cagttaacat aaatattggc 3480
ccaggtgact gtgaatggtt tgttgttcct gaaggttact ggggtgttct gaatgacttc 3540
tgtgaaaaaa ataatttgaa tttcctaatg ggttcttggt ggcccaatct tgaagatctt 3600
tatgaagcaa atgttccagt gtataggttt attcagcgac ctggagattt ggtctggata 3660
aatgcaggca ctgttcattg ggttcaggct attggctggt gcaacaacat tgcttggaat 3720
gttggtccac ttacagcctg ccagtataaa ttggcagtgg aacggtacga atggaacaaa 3780
ttgcaaagtg tgaagtcaat agtacccatg gttcatcttt cctggaatat ggcacgaaat 3840
atcaaggtct cagatccaaa gctttttgaa atgattaagt attgtcttct aagaactctg 3900
aagcaatgtc agacattgag ggaagctctc attgctgcag gaaaagagat tatatggcat 3960
gggcggacaa aagaagaacc agctcattac tgtagcattt gtgaagtgga ggtttttgat 4020
ctgctttttg tcactaatga gagtaattca cgaaagacct acatagtaca ttgccaagat 4080
tgtgcacgaa aaacaagcgg aaacttggaa aactttgtgg tgctagaaca gtacaaaatg 4140
gaggacctga tgcaagtcta tgaccaattt acattagctc ctccattacc atccgcctca 4200
tcttga 4206

<210> SEQ ID NO 9
<211> LENGTH: 4206
<212> TYPE: DNA
<213> ORGANISM: Homo sapiens

<400> SEQUENCE: 9
atgaaatcct gcggagtgtc gctcgctacc gccgccgctg ccgccgccgc tttcggtgat 60
gaggaaaaga aaatggcggc gggaaaagcg agcggcgaga gcgaggaggc gtcccccagc 120

-continued

```
ctgacagccg aggagaggga ggcgctcggc ggactggaca gccgcctctt tgggttcgtg    180
agatttcatg aagatggcgc caggacgaag gccctactgg gcaaggctgt tcgctgctat    240
gaatctctaa tcttaaaagc tgaaggaaaa gtggagtctg atttcttttg tcaattaggt    300
cacttcaacc tcttattgga agattatcca aaagcattat ctgcatacca gaggtactac    360
agtttacagt ctgactactg gaagaatgct gccttttttat atggtcttgg tttggtctac    420
ttccattata atgcatttca gtgggcaatt aaagcatttc aggaggtgct ttatgttgat    480
cccagctttt gtcgagccaa ggaaattcat ttacgagttg ggcttatgtt caaagtgaac    540
acagactatg agtctagttt aaagcatttt cagttagctt tggttgactg taatccctgc    600
actttgtcca atgctgaaat tcaatttcac attgcccact tatatgaaac ccagaggaaa    660
tatcattctg caaaagaagc ttatgaacaa cttttgcaga cagagaatct ttctgcacaa    720
gtaaaagcaa ctgtcttaca acagttaggt tggatgcatc acactgtaga tctcctggga    780
gataaagcca ccaaggaaag ctatgctatt cagtatctcc aaaagtcctt ggaagcagat    840
cctaattctg gccagtcctg gtatttcctc ggaaggtgct attcaagtat tgggaaagtt    900
caggatgcct ttatatctta caggcagtct attgataaat cagaagcaag tgcagataca    960
tggtgttcaa taggtgtgct atatcagcag caaaatcagc ccatggatgc tttacaggcc   1020
tatatttgtg ctgtacaatt ggaccatggc catgctgcag cctggatgga cctaggcact   1080
ctctatgaat cctgcaacca gcctcaggat gccattaaat gctacttaaa tgcaactaga   1140
agcaaaagtt gtagtaatac ctctgcactt gcagcacgaa ttaagtattt acaggctcag   1200
ttgtgtaacc ttccacaagg tagtctacag aataaaacta aattacttcc tagtattgag   1260
gaggcgtgga gcctaccaat tcccgcagag cttacctcca ggcagggtgc catgaacaca   1320
gcacagcaga atacttctga caattggagt ggtggacatg ctgtgtcaca tcctccagta   1380
cagcaacaag ctcattcatg gtgtttgaca ccacagaaat tacagcattt ggaacagctc   1440
cgcgcaaata gaaataattt aaatccagca cagaaactga tgctggaaca gctggaaagt   1500
cagtttgtct taatgcaaca acaccaaatg agaccaacag gagttgcaca ggtacgatct   1560
actggaattc ctaatgggcc aacagctgac tcatcactgc ctacaaactc agtctctggc   1620
cagcagccac agcttgctct gaccagagtg cctagcgtct ctcagcctgg agtccgtcct   1680
gcctgccctg ggcagccttt ggccaatgga cccttttctg caggccatgt tccctgtagc   1740
acatcaagaa cgcggggaag tacagacact attttgatag gcaataatca tataacagga   1800
aatggaagta atggaaacgt gccttacctg cagcgaaacg cactcactct acctcataac   1860
cgcacaaacc tgaccagcag cgcaaaggag ccgtggaaaa accaactatc taactccact   1920
caggggcttc acaaaggtca gagttcacat tcggcaggtc ctaatggtga acgacctctc   1980
tcttccactg ggccttccca gcatctccag gcagctggct ctggtattca gaatcagaac   2040
ggacatccca ccctgcctag caattcagta acacaggggg ctgctctcaa tcacctctcc   2100
tctcacactg ctacctcagg tggacaacaa ggcattacct taaccaaaga gagcaagcct   2160
tcaggaaaca tattgacggt gcctgaaaca agcaggcaca ctggagagac acctaacagc   2220
actgccagtg tcgagggact tcctaatcat gtccatcaga tgacggcaga tgctgtttgc   2280
agtcctagcc atggagattc taagtcacca ggtttactaa gttcagacaa tcctcagctc   2340
tctgccttgt tgatgggaaa agccaataac aatgtgggta ctggaacctg tgacaaagtc   2400
aataacatcc acccagctgt tcatacaaag actgataact ctgttgcctc ttcaccatct   2460
tcagccattt caacagcaac accttctcca aaatccactg agcagacaac cacaaacagt   2520
```

-continued

```
gttaccagcc ttaacagccc tcacagtggg ctacacacaa ttaatggaga agggatggaa   2580
gaatctcaga gccccatgaa aacagatctg cttctggtta accacaaacc tagtccacag   2640
atcataccat caatgtctgt gtccatatac cccagctcag cagaagttct gaaggcatgc   2700
aggaatctag gtaaaaatgg cttatctaac agtagcattt tgttggataa atgtccacct   2760
ccaagaccac catcttcacc ataccctccc ttgccaaagg acaagttgaa tccacctaca   2820
cctagtattt acttggaaaa taaacgtgat gctttctttc ctccattaca tcaattttgt   2880
acaaatccga acaaccctgt tacagtaata cgtggccttg ctggagctct taagttagac   2940
ctgggacttt tctctactaa aactttggtg gaagctaaca atgaacatat ggtagaagtg   3000
aggacacagt tgttgcagcc agcagatgaa aactgggatc ccactggaac aaagaaaatc   3060
tggcattgtg aaagtaatag atctcatact acaattgcta aatatgcaca gtaccaggcc   3120
tcctcattcc aggaatcatt gagagaagaa aatgaaaaaa gaagtcatca taaagaccac   3180
tcagatagtg aatctacatc gtcagataat tctgggagga ggaggaaagg accctttaaa   3240
accataaagt ttgggaccaa tattgaccta tctgatgaca aaaagtggaa gttgcagcta   3300
catgagctga ctaaacttcc tgcttttgtg cgtgtcgtat cagcaggaaa tcttctaagc   3360
catgttggtc ataccatatt gggcatgaac acagttcaac tatacatgaa agttccaggg   3420
agcagaacac caggtcatca ggaaaataac aacttctgtt cagttaacat aaatattggc   3480
ccaggtgact gtgaatggtt tgttgttcct gaaggttact ggggtgtttt gaatgacttc   3540
tgtgaaaaaa ataatttgaa tttcctaatg ggttcttggt ggcccaatct tgaagatctt   3600
tatgaagcaa atgttccagt gtataggttt attcagcgac ctggagattt ggtctggata   3660
aatgcaggca ctgttcattg ggttcaggct attggctggt gcaacaacat tgcttggaat   3720
gttggtccac ttacagcctg ccagtataaa ttggcagtgg aacggtacga atggaacaaa   3780
ttgcaaagtg tgaagtcaat agtacccatg gttcatcttt cctggaatat ggcacgaaat   3840
atcaaggtct cagatccaaa gctttttgaa atgattaagt attgtcttct aagaactctg   3900
aagcaatgtc agacattgag ggaagctctc attgctgcag gaaaagagat tatatggcat   3960
gggcggacaa aagaagaacc agctcattac tgtagcattt gtgaagtgga ggtttttgat   4020
ctgcttttttg tcactaatga gagtaattca cgaaaagacct acatagtaca ttgccaagat   4080
tgtgcacgaa aaacaagcgg aaacttggaa aactttgtgg tgctagaaca gtacaaaatg   4140
gaggacctga tgcaagtcta tgaccaattt acattagctc ctccattacc atccgcctca   4200
tcttga                                                              4206
```

<210> SEQ ID NO 10
<211> LENGTH: 1401
<212> TYPE: PRT
<213> ORGANISM: Homo sapiens

<400> SEQUENCE: 10

```
Met Lys Ser Cys Gly Val Ser Leu Ala Thr Ala Ala Ala Ala Ala Ala
1               5                   10                  15

Ala Phe Gly Asp Glu Glu Lys Lys Met Ala Ala Gly Lys Ala Ser Gly
            20                  25                  30

Glu Ser Glu Glu Ala Ser Pro Ser Leu Thr Ala Glu Glu Arg Glu Ala
        35                  40                  45

Leu Gly Gly Leu Asp Ser Arg Leu Phe Gly Phe Val Arg Phe His Glu
    50                  55                  60
```

```
Asp Gly Ala Arg Thr Lys Ala Leu Leu Gly Lys Ala Val Arg Cys Tyr
65                  70                  75                  80

Glu Ser Leu Ile Leu Lys Ala Glu Gly Lys Val Glu Ser Asp Phe Phe
                85                  90                  95

Cys Gln Leu Gly His Phe Asn Leu Leu Leu Glu Asp Tyr Pro Lys Ala
            100                 105                 110

Leu Ser Ala Tyr Gln Arg Tyr Tyr Ser Leu Gln Ser Asp Tyr Trp Lys
        115                 120                 125

Asn Ala Ala Phe Leu Tyr Gly Leu Gly Leu Val Tyr Phe His Tyr Asn
    130                 135                 140

Ala Phe Gln Trp Ala Ile Lys Ala Phe Gln Glu Val Leu Tyr Val Asp
145                 150                 155                 160

Pro Ser Phe Cys Arg Ala Lys Glu Ile His Leu Arg Leu Gly Leu Met
                165                 170                 175

Phe Lys Val Asn Thr Asp Tyr Glu Ser Ser Leu Lys His Phe Gln Leu
            180                 185                 190

Ala Leu Val Asp Cys Asn Pro Cys Thr Leu Ser Asn Ala Glu Ile Gln
        195                 200                 205

Phe His Ile Ala His Leu Tyr Glu Thr Gln Arg Lys Tyr His Ser Ala
    210                 215                 220

Lys Glu Ala Tyr Glu Gln Leu Leu Gln Thr Glu Asn Leu Ser Ala Gln
225                 230                 235                 240

Val Lys Ala Thr Val Leu Gln Gln Leu Gly Trp Met His His Thr Val
                245                 250                 255

Asp Leu Leu Gly Asp Lys Ala Thr Lys Glu Ser Tyr Ala Ile Gln Tyr
            260                 265                 270

Leu Gln Lys Ser Leu Glu Ala Asp Pro Asn Ser Gly Gln Ser Trp Tyr
        275                 280                 285

Phe Leu Gly Arg Cys Tyr Ser Ser Ile Gly Lys Val Gln Asp Ala Phe
    290                 295                 300

Ile Ser Tyr Arg Gln Ser Ile Asp Lys Ser Glu Ala Ser Ala Asp Thr
305                 310                 315                 320

Trp Cys Ser Ile Gly Val Leu Tyr Gln Gln Gln Asn Gln Pro Met Asp
                325                 330                 335

Ala Leu Gln Ala Tyr Ile Cys Ala Val Gln Leu Asp His Gly His Ala
            340                 345                 350

Ala Ala Trp Met Asp Leu Gly Thr Leu Tyr Glu Ser Cys Asn Gln Pro
        355                 360                 365

Gln Asp Ala Ile Lys Cys Tyr Leu Asn Ala Thr Arg Ser Lys Ser Cys
    370                 375                 380

Ser Asn Thr Ser Ala Leu Ala Ala Arg Ile Lys Tyr Leu Gln Ala Gln
385                 390                 395                 400

Leu Cys Asn Leu Pro Gln Gly Ser Leu Gln Asn Lys Thr Lys Leu Leu
                405                 410                 415

Pro Ser Ile Glu Glu Ala Trp Ser Leu Pro Ile Pro Ala Glu Leu Thr
            420                 425                 430

Ser Arg Gln Gly Ala Met Asn Thr Ala Gln Gln Asn Thr Ser Asp Asn
        435                 440                 445

Trp Ser Gly Gly His Ala Val Ser His Pro Pro Val Gln Gln Gln Ala
    450                 455                 460

His Ser Trp Cys Leu Thr Pro Gln Lys Leu Gln His Leu Glu Gln Leu
465                 470                 475                 480

Arg Ala Asn Arg Asn Asn Leu Asn Pro Ala Gln Lys Leu Met Leu Glu
```

```
                485                 490                 495

Gln Leu Glu Ser Gln Phe Val Leu Met Gln Gln His Gln Met Arg Pro
            500                 505                 510

Thr Gly Val Ala Gln Val Arg Ser Thr Gly Ile Pro Asn Gly Pro Thr
        515                 520                 525

Ala Asp Ser Ser Leu Pro Thr Asn Ser Val Ser Gly Gln Gln Pro Gln
    530                 535                 540

Leu Ala Leu Thr Arg Val Pro Ser Val Ser Gln Pro Gly Val Arg Pro
545                 550                 555                 560

Ala Cys Pro Gly Gln Pro Leu Ala Asn Gly Pro Phe Ser Ala Gly His
                565                 570                 575

Val Pro Cys Ser Thr Ser Arg Thr Leu Gly Ser Thr Asp Thr Ile Leu
            580                 585                 590

Ile Gly Asn Asn His Ile Thr Gly Ser Gly Ser Asn Gly Asn Val Pro
        595                 600                 605

Tyr Leu Gln Arg Asn Ala Leu Thr Leu Pro His Asn Arg Thr Asn Leu
    610                 615                 620

Thr Ser Ser Ala Glu Glu Pro Trp Lys Asn Gln Leu Ser Asn Ser Thr
625                 630                 635                 640

Gln Gly Leu His Lys Gly Gln Ser Ser His Ser Ala Gly Pro Asn Gly
                645                 650                 655

Glu Arg Pro Leu Ser Ser Thr Gly Pro Ser Gln His Leu Gln Ala Ala
            660                 665                 670

Gly Ser Gly Ile Gln Asn Gln Asn Gly His Pro Thr Leu Pro Ser Asn
        675                 680                 685

Ser Val Thr Gln Gly Ala Ala Leu Asn His Leu Ser Ser His Thr Ala
    690                 695                 700

Thr Ser Gly Gly Gln Gln Gly Ile Thr Leu Thr Lys Glu Ser Lys Pro
705                 710                 715                 720

Ser Gly Asn Ile Leu Thr Val Pro Glu Thr Ser Arg His Thr Gly Glu
                725                 730                 735

Thr Pro Asn Ser Thr Ala Ser Val Glu Gly Leu Pro Asn His Val His
            740                 745                 750

Gln Met Thr Ala Asp Ala Val Cys Ser Pro Ser His Gly Asp Ser Lys
        755                 760                 765

Ser Pro Gly Leu Leu Ser Ser Asp Asn Pro Gln Leu Ser Ala Leu Leu
    770                 775                 780

Met Gly Lys Ala Asn Asn Asn Val Gly Thr Gly Thr Cys Asp Lys Val
785                 790                 795                 800

Asn Asn Ile His Pro Ala Val His Thr Lys Thr Asp Asn Ser Val Ala
                805                 810                 815

Ser Ser Pro Ser Ser Ala Ile Ser Thr Ala Thr Pro Ser Pro Lys Ser
            820                 825                 830

Thr Glu Gln Thr Thr Thr Asn Ser Val Thr Ser Leu Asn Ser Pro His
        835                 840                 845

Ser Gly Leu His Thr Ile Asn Gly Glu Gly Met Glu Glu Ser Gln Ser
    850                 855                 860

Pro Met Lys Thr Asp Leu Leu Leu Val Asn His Lys Pro Ser Pro Gln
865                 870                 875                 880

Ile Ile Pro Ser Met Ser Val Ser Ile Tyr Pro Ser Ser Ala Glu Val
                885                 890                 895

Leu Lys Ala Cys Arg Asn Leu Gly Lys Asn Gly Leu Ser Asn Ser Ser
            900                 905                 910
```

-continued

```
Ile Leu Leu Asp Lys Cys Pro Pro Pro Arg Pro Pro Ser Ser Pro Tyr
        915                 920                 925

Pro Pro Leu Pro Lys Asp Lys Leu Asn Pro Pro Thr Pro Ser Ile Tyr
    930                 935                 940

Leu Glu Asn Lys Arg Asp Ala Phe Phe Pro Pro Leu His Gln Phe Cys
945                 950                 955                 960

Thr Asn Pro Asn Asn Pro Val Thr Val Ile Arg Gly Leu Ala Gly Ala
                965                 970                 975

Leu Lys Leu Asp Leu Gly Leu Phe Ser Thr Lys Thr Leu Val Glu Ala
            980                 985                 990

Asn Asn Glu His Met Val Glu Val Arg Thr Gln Leu Leu Gln Pro Ala
        995                 1000                1005

Asp Glu Asn Trp Asp Pro Thr Gly Thr Lys Lys Ile Trp His Cys Glu
    1010                1015                1020

Ser Asn Arg Ser His Thr Thr Ile Ala Lys Tyr Ala Gln Tyr Gln Ala
1025                1030                1035                1040

Ser Ser Phe Gln Glu Ser Leu Arg Glu Glu Asn Glu Lys Arg Ser His
                1045                1050                1055

His Lys Asp His Ser Asp Ser Glu Ser Thr Ser Ser Asp Asn Ser Gly
            1060                1065                1070

Arg Arg Arg Lys Gly Pro Phe Lys Thr Ile Lys Phe Gly Thr Asn Ile
        1075                1080                1085

Asp Leu Ser Asp Asp Lys Lys Trp Lys Leu Gln Leu His Glu Leu Thr
    1090                1095                1100

Lys Leu Pro Ala Phe Val Arg Val Val Ser Ala Gly Asn Leu Leu Ser
1105                1110                1115                1120

His Val Gly His Thr Ile Leu Gly Met Asn Thr Val Gln Leu Tyr Met
                1125                1130                1135

Lys Val Pro Gly Ser Arg Thr Pro Gly His Gln Glu Asn Asn Asn Phe
            1140                1145                1150

Cys Ser Val Asn Ile Asn Ile Gly Pro Gly Asp Cys Glu Trp Phe Val
        1155                1160                1165

Val Pro Glu Gly Tyr Trp Gly Val Leu Asn Asp Phe Cys Glu Lys Asn
    1170                1175                1180

Asn Leu Asn Phe Leu Met Gly Ser Trp Trp Pro Asn Leu Glu Asp Leu
1185                1190                1195                1200

Tyr Glu Ala Asn Val Pro Val Tyr Arg Phe Ile Gln Arg Pro Gly Asp
                1205                1210                1215

Leu Val Trp Ile Asn Ala Gly Thr Val His Trp Val Gln Ala Ile Gly
            1220                1225                1230

Trp Cys Asn Asn Ile Ala Trp Asn Val Gly Pro Leu Thr Ala Cys Gln
        1235                1240                1245

Tyr Lys Leu Ala Val Glu Arg Tyr Glu Trp Asn Lys Leu Gln Ser Val
    1250                1255                1260

Lys Ser Ile Val Pro Met Val His Leu Ser Trp Asn Met Ala Arg Asn
1265                1270                1275                1280

Ile Lys Val Ser Asp Pro Lys Leu Phe Glu Met Ile Lys Tyr Cys Leu
                1285                1290                1295

Leu Arg Thr Leu Lys Gln Cys Gln Thr Leu Arg Glu Ala Leu Ile Ala
            1300                1305                1310

Ala Gly Lys Glu Ile Ile Trp His Gly Arg Thr Lys Glu Glu Pro Ala
        1315                1320                1325
```

```
His Tyr Cys Ser Ile Cys Glu Val Glu Val Phe Asp Leu Leu Phe Val
    1330                1335                1340

Thr Asn Glu Ser Asn Ser Arg Lys Thr Tyr Ile Val His Cys Gln Asp
1345                1350                1355                1360

Cys Ala Arg Lys Thr Ser Gly Asn Leu Glu Asn Phe Val Val Leu Glu
                1365                1370                1375

Gln Tyr Lys Met Glu Asp Leu Met Gln Val Tyr Asp Gln Phe Thr Leu
            1380                1385                1390

Ala Pro Pro Leu Pro Ser Ala Ser Ser
        1395                1400


<210> SEQ ID NO 11
<211> LENGTH: 1401
<212> TYPE: PRT
<213> ORGANISM: Homo sapiens

<400> SEQUENCE: 11

Met Lys Ser Cys Gly Val Ser Leu Ala Thr Ala Ala Ala Ala Ala Ala
1               5                   10                  15

Ala Phe Gly Asp Glu Glu Lys Lys Met Ala Ala Gly Lys Ala Ser Gly
            20                  25                  30

Glu Ser Glu Glu Ala Ser Pro Ser Leu Thr Ala Glu Glu Arg Glu Ala
        35                  40                  45

Leu Gly Gly Leu Asp Ser Arg Leu Phe Gly Phe Val Arg Phe His Glu
    50                  55                  60

Asp Gly Ala Arg Thr Lys Ala Leu Leu Gly Lys Ala Val Arg Cys Tyr
65                  70                  75                  80

Glu Ser Leu Ile Leu Lys Ala Glu Gly Lys Val Glu Ser Asp Phe Phe
                85                  90                  95

Cys Gln Leu Gly His Phe Asn Leu Leu Leu Glu Asp Tyr Pro Lys Ala
            100                 105                 110

Leu Ser Ala Tyr Gln Arg Tyr Tyr Ser Leu Gln Ser Asp Tyr Trp Lys
        115                 120                 125

Asn Ala Ala Phe Leu Tyr Gly Leu Gly Leu Val Tyr Phe His Tyr Asn
    130                 135                 140

Ala Phe Gln Trp Ala Ile Lys Ala Phe Gln Glu Val Leu Tyr Val Asp
145                 150                 155                 160

Pro Ser Phe Cys Arg Ala Lys Glu Ile His Leu Arg Val Gly Leu Met
                165                 170                 175

Phe Lys Val Asn Thr Asp Tyr Glu Ser Ser Leu Lys His Phe Gln Leu
            180                 185                 190

Ala Leu Val Asp Cys Asn Pro Cys Thr Leu Ser Asn Ala Glu Ile Gln
        195                 200                 205

Phe His Ile Ala His Leu Tyr Glu Thr Gln Arg Lys Tyr His Ser Ala
    210                 215                 220

Lys Glu Ala Tyr Glu Gln Leu Leu Gln Thr Glu Asn Leu Ser Ala Gln
225                 230                 235                 240

Val Lys Ala Thr Val Leu Gln Gln Leu Gly Trp Met His His Thr Val
                245                 250                 255

Asp Leu Leu Gly Asp Lys Ala Thr Lys Glu Ser Tyr Ala Ile Gln Tyr
            260                 265                 270

Leu Gln Lys Ser Leu Glu Ala Asp Pro Asn Ser Gly Gln Ser Trp Tyr
        275                 280                 285

Phe Leu Gly Arg Cys Tyr Ser Ser Ile Gly Lys Val Gln Asp Ala Phe
    290                 295                 300
```

-continued

```
Ile Ser Tyr Arg Gln Ser Ile Asp Lys Ser Glu Ala Ser Ala Asp Thr
305                 310                 315                 320

Trp Cys Ser Ile Gly Val Leu Tyr Gln Gln Gln Asn Gln Pro Met Asp
                325                 330                 335

Ala Leu Gln Ala Tyr Ile Cys Ala Val Gln Leu Asp His Gly His Ala
            340                 345                 350

Ala Ala Trp Met Asp Leu Gly Thr Leu Tyr Glu Ser Cys Asn Gln Pro
        355                 360                 365

Gln Asp Ala Ile Lys Cys Tyr Leu Asn Ala Thr Arg Ser Lys Ser Cys
    370                 375                 380

Ser Asn Thr Ser Ala Leu Ala Ala Arg Ile Lys Tyr Leu Gln Ala Gln
385                 390                 395                 400

Leu Cys Asn Leu Pro Gln Gly Ser Leu Gln Asn Lys Thr Lys Leu Leu
                405                 410                 415

Pro Ser Ile Glu Glu Ala Trp Ser Leu Pro Ile Pro Ala Glu Leu Thr
            420                 425                 430

Ser Arg Gln Gly Ala Met Asn Thr Ala Gln Gln Asn Thr Ser Asp Asn
        435                 440                 445

Trp Ser Gly Gly His Ala Val Ser His Pro Pro Val Gln Gln Gln Ala
    450                 455                 460

His Ser Trp Cys Leu Thr Pro Gln Lys Leu Gln His Leu Glu Gln Leu
465                 470                 475                 480

Arg Ala Asn Arg Asn Asn Leu Asn Pro Ala Gln Lys Leu Met Leu Glu
                485                 490                 495

Gln Leu Glu Ser Gln Phe Val Leu Met Gln Gln His Gln Met Arg Pro
            500                 505                 510

Thr Gly Val Ala Gln Val Arg Ser Thr Gly Ile Pro Asn Gly Pro Thr
        515                 520                 525

Ala Asp Ser Ser Leu Pro Thr Asn Ser Val Ser Gly Gln Gln Pro Gln
    530                 535                 540

Leu Ala Leu Thr Arg Val Pro Ser Val Ser Gln Pro Gly Val Arg Pro
545                 550                 555                 560

Ala Cys Pro Gly Gln Pro Leu Ala Asn Gly Pro Phe Ser Ala Gly His
                565                 570                 575

Val Pro Cys Ser Thr Ser Arg Thr Arg Gly Ser Thr Asp Thr Ile Leu
            580                 585                 590

Ile Gly Asn Asn His Ile Thr Gly Asn Gly Ser Asn Gly Asn Val Pro
        595                 600                 605

Tyr Leu Gln Arg Asn Ala Leu Thr Leu Pro His Asn Arg Thr Asn Leu
    610                 615                 620

Thr Ser Ser Ala Lys Glu Pro Trp Lys Asn Gln Leu Ser Asn Ser Thr
625                 630                 635                 640

Gln Gly Leu His Lys Gly Gln Ser Ser His Ser Ala Gly Pro Asn Gly
                645                 650                 655

Glu Arg Pro Leu Ser Ser Thr Gly Pro Ser Gln His Leu Gln Ala Ala
            660                 665                 670

Gly Ser Gly Ile Gln Asn Gln Asn Gly His Pro Thr Leu Pro Ser Asn
        675                 680                 685

Ser Val Thr Gln Gly Ala Ala Leu Asn His Leu Ser Ser His Thr Ala
    690                 695                 700

Thr Ser Gly Gly Gln Gln Gly Ile Thr Leu Thr Lys Glu Ser Lys Pro
705                 710                 715                 720
```

-continued

```
Ser Gly Asn Ile Leu Thr Val Pro Glu Thr Ser Arg His Thr Gly Glu
                725                 730                 735

Thr Pro Asn Ser Thr Ala Ser Val Glu Gly Leu Pro Asn His Val His
            740                 745                 750

Gln Met Thr Ala Asp Ala Val Cys Ser Pro Ser His Gly Asp Ser Lys
        755                 760                 765

Ser Pro Gly Leu Leu Ser Ser Asp Asn Pro Gln Leu Ser Ala Leu Leu
    770                 775                 780

Met Gly Lys Ala Asn Asn Asn Val Gly Thr Gly Thr Cys Asp Lys Val
785                 790                 795                 800

Asn Asn Ile His Pro Ala Val His Thr Lys Thr Asp Asn Ser Val Ala
                805                 810                 815

Ser Ser Pro Ser Ser Ala Ile Ser Thr Ala Thr Pro Ser Pro Lys Ser
            820                 825                 830

Thr Glu Gln Thr Thr Thr Asn Ser Val Thr Ser Leu Asn Ser Pro His
        835                 840                 845

Ser Gly Leu His Thr Ile Asn Gly Glu Gly Met Glu Glu Ser Gln Ser
    850                 855                 860

Pro Met Lys Thr Asp Leu Leu Leu Val Asn His Lys Pro Ser Pro Gln
865                 870                 875                 880

Ile Ile Pro Ser Met Ser Val Ser Ile Tyr Pro Ser Ser Ala Glu Val
                885                 890                 895

Leu Lys Ala Cys Arg Asn Leu Gly Lys Asn Gly Leu Ser Asn Ser Ser
            900                 905                 910

Ile Leu Leu Asp Lys Cys Pro Pro Pro Arg Pro Pro Ser Ser Pro Tyr
        915                 920                 925

Pro Pro Leu Pro Lys Asp Lys Leu Asn Pro Pro Thr Pro Ser Ile Tyr
    930                 935                 940

Leu Glu Asn Lys Arg Asp Ala Phe Phe Pro Pro Leu His Gln Phe Cys
945                 950                 955                 960

Thr Asn Pro Asn Asn Pro Val Thr Val Ile Arg Gly Leu Ala Gly Ala
                965                 970                 975

Leu Lys Leu Asp Leu Gly Leu Phe Ser Thr Lys Thr Leu Val Glu Ala
            980                 985                 990

Asn Asn Glu His Met Val Glu Val Arg Thr Gln Leu Leu Gln Pro Ala
        995                 1000                1005

Asp Glu Asn Trp Asp Pro Thr Gly Thr Lys Lys Ile Trp His Cys Glu
    1010                1015                1020

Ser Asn Arg Ser His Thr Thr Ile Ala Lys Tyr Ala Gln Tyr Gln Ala
1025                1030                1035                1040

Ser Ser Phe Gln Glu Ser Leu Arg Glu Glu Asn Glu Lys Arg Ser His
                1045                1050                1055

His Lys Asp His Ser Asp Ser Glu Ser Thr Ser Ser Asp Asn Ser Gly
            1060                1065                1070

Arg Arg Arg Lys Gly Pro Phe Lys Thr Ile Lys Phe Gly Thr Asn Ile
        1075                1080                1085

Asp Leu Ser Asp Asp Lys Lys Trp Lys Leu Gln Leu His Glu Leu Thr
    1090                1095                1100

Lys Leu Pro Ala Phe Val Arg Val Val Ser Ala Gly Asn Leu Leu Ser
1105                1110                1115                1120

His Val Gly His Thr Ile Leu Gly Met Asn Thr Val Gln Leu Tyr Met
                1125                1130                1135

Lys Val Pro Gly Ser Arg Thr Pro Gly His Gln Glu Asn Asn Asn Phe
```

```
            1140                1145                1150

Cys Ser Val Asn Ile Asn Ile Gly Pro Gly Asp Cys Glu Trp Phe Val
        1155                1160                1165

Val Pro Glu Gly Tyr Trp Gly Val Leu Asn Asp Phe Cys Glu Lys Asn
    1170                1175                1180

Asn Leu Asn Phe Leu Met Gly Ser Trp Trp Pro Asn Leu Glu Asp Leu
1185                1190                1195                1200

Tyr Glu Ala Asn Val Pro Val Tyr Arg Phe Ile Gln Arg Pro Gly Asp
                1205                1210                1215

Leu Val Trp Ile Asn Ala Gly Thr Val His Trp Val Gln Ala Ile Gly
            1220                1225                1230

Trp Cys Asn Asn Ile Ala Trp Asn Val Gly Pro Leu Thr Ala Cys Gln
        1235                1240                1245

Tyr Lys Leu Ala Val Glu Arg Tyr Glu Trp Asn Lys Leu Gln Ser Val
    1250                1255                1260

Lys Ser Ile Val Pro Met Val His Leu Ser Trp Asn Met Ala Arg Asn
1265                1270                1275                1280

Ile Lys Val Ser Asp Pro Lys Leu Phe Glu Met Ile Lys Tyr Cys Leu
                1285                1290                1295

Leu Arg Thr Leu Lys Gln Cys Gln Thr Leu Arg Glu Ala Leu Ile Ala
            1300                1305                1310

Ala Gly Lys Glu Ile Ile Trp His Gly Arg Thr Lys Glu Glu Pro Ala
        1315                1320                1325

His Tyr Cys Ser Ile Cys Glu Val Glu Val Phe Asp Leu Leu Phe Val
    1330                1335                1340

Thr Asn Glu Ser Asn Ser Arg Lys Thr Tyr Ile Val His Cys Gln Asp
1345                1350                1355                1360

Cys Ala Arg Lys Thr Ser Gly Asn Leu Glu Asn Phe Val Val Leu Glu
                1365                1370                1375

Gln Tyr Lys Met Glu Asp Leu Met Gln Val Tyr Asp Gln Phe Thr Leu
            1380                1385                1390

Ala Pro Pro Leu Pro Ser Ala Ser Ser
        1395                1400
```

<210> SEQ ID NO 12
<211> LENGTH: 3896
<212> TYPE: DNA
<213> ORGANISM: Homo sapiens

<400> SEQUENCE: 12

```
ccttccgcag ctgccgcttc agtccgaagg aggaagggaa ccaacccact ttctcggcgc      60

cgcggctctt ttctaaaagt aatgtgaaaa cctttgcatc ttctgatagt ctagccaagg     120

tccaagaagt agcaagctgg cttttggaaa tgaatcagga actgctctct gtgggcagca     180

aaagacgacg aactggaggc tctctgagag gtaacccttc ctcaagccag gtagatgaag     240

aacagatgaa tcgtgtggta gaggaggaac agcaacagca actcagacaa caagaggagg     300

agcacactgc aaggaatggt gaagttgttg gagtagaacc tagacctgga ggccaaaatg     360

attcccagca aggacagttg gaagaaaaca ataatagatt tatttcggta gatgaggact     420

cctcaggaaa ccaagaagaa caagaggaag atgaagaaca tgctggtgaa caagatgagg     480

aggatgagga ggaggaggag atggaccagg agagtgacga ttttgatcag tctgatgata     540

gtagcagaga agatgaacat acacatacta acagtgtcac gaactccagt agtattgtgg     600

acctgcccgt tcaccaactc tcctccccat tctatacaaa aacaacaaaa atgaaaagaa     660
```

```
agttggacca tggttctgag gtccgctctt tttctttggg aaagaaacca tgcaaagtct    720

cagaatatac aagtaccact gggcttgtac catgttcagc aacaccaaca acttttgggg    780

acctcagagc agccaatggc caagggcaac aacgacgccg aattacatct gtccagccac    840

ctacaggcct ccaggaatgg ctaaaaatgt ttcagagctg gagtggacca gagaaattgc    900

ttgctttaga tgaactcatt gatagttgtg aaccaacaca agtaaaacat atgatgcaag    960

tgatagaacc ccagtttcaa cgagacttca tttcattgct ccctaaagag ttggcactct   1020

atgtgctttc attcctggaa cccaaagacc tgctacaagc agctcagaca tgtcgctact   1080

ggagaatttt ggctgaagac aaccttctct ggagagagaa atgcaaagaa gaggggattg   1140

atgaaccatt gcacatcaag agaagaaaag taataaaacc aggtttcata cacagtccat   1200

ggaaaagtgc atacatcaga cagcacagaa ttgatactaa ctggaggcga ggagaactca   1260

aatctcctaa ggtgctgaaa ggacatgatg atcatgtgat cacatgctta cagttttgtg   1320

gtaaccgaat agttagtggt tctgatgaca acactttaaa agtttggtca gcagtcacag   1380

gcaaatgtct gagaacatta gtgggacata caggtggagt atggtcatca caaatgagag   1440

acaacatcat cattagtgga tctacagatc ggacactcaa agtgtggaat gcagagactg   1500

gagaatgtat acacacctta tatgggcata cttccactgt gcgttgtatg catcttcatg   1560

aaaaaagagt tgttagcggt tctcgagatg ccactcttag ggtttgggat attgagacag   1620

gccagtgttt acatgttttg atgggtcatg ttgcagcagt ccgctgtgtt caatatgatg   1680

gcaggagggt tgttagtgga gcatatgatt ttatggtaaa ggtgtgggat ccagagactg   1740

aaacctgtct acacacgttg caggggcata ctaatagagt ctattcatta cagtttgatg   1800

gtatccatgt ggtgagtgga tctcttgata catcaatccg tgtttgggat gtggagacag   1860

ggaattgcat tcacacgtta acagggcacc agtcgttaac aagtggaatg gaactcaaag   1920

acaatattct tgtctctggg aatgcagatt ctacagttaa aatctgggat atcaaaacag   1980

gacagtgttt acaaacattg caaggtccca acaagcatca gagtgctgtg acctgtttac   2040

agttcaacaa gaactttgta attaccagct cagatgatgg aactgtaaaa ctatgggact   2100

tgaaaacggg tgaatttatt cgaaacctag tcacattgga gagtgggggg agtgggggag   2160

ttgtgtggcg gatcagagcc tcaaacacaa agctggtgtg tgcagttggg agtcggaatg   2220

ggactgaaga aaccaagctg ctggtgctgg actttgatgt ggacatgaag tgaagagcag   2280

aaaagatgaa tttgtccaat tgtgtagacg atatactccc tgcccttccc cctgcaaaaa   2340

gaaaaaaaga aaagaaaaag aaaaaaatcc cttgttctca gtggtgcagg atgttggctt   2400

ggggcaacag attgaaaaga cctacagact aagaaggaaa agaagaagag atgacaaacc   2460

ataactgaca agagaggcgt ctgctgtctc atcacataaa aggcttcact tttgactgag   2520

ggcagctttg caaaatgaga ctttctaaat caaaccaggt gcaattattt ctttattttc   2580

ttctccagtg gtcattgggc agtgttaatg ctgaaacatc attacagatt ctgctagcct   2640

gttcttttac cactgacagc tagacaccta gaaaggaact gcaataatat caaaacaagt   2700

actggttgac tttctaatta gagagcatct gcaacaaaaa gtcatttttc tggagtggaa   2760

aagcttaaaa aaattactgt gaattgtttt tgtacagtta tcatgaaaag cttttttttt   2820

tttttttttg ccaaccattg ccaatgtcaa tcaatcacag tattagcctc tgttaatcta   2880

tttactgttg cttccatata cattcttcaa tgcatatgtt gctcaaaggt ggcaagttgt   2940

cctgggttct gtgagtcctg agatggattt aattcttgat gctggtgcta gaagtaggtc   3000
```

-continued

```
ttcaaatatg ggattgttgt cccaaccctg tactgtactc ccagtggcca aacttattta   3060

tgctgctaaa tgaaagaaag aaaaaagcaa attatttttt tttatttttt ttctgctgtg   3120

acgttttagt cccagactga attccaaatt tgctctagtt tggttatgga aaaaagactt   3180

tttgccactg aaacttgagc catctgtgcc tctaagaggc tgagaatgga agagtttcag   3240

ataataaaga gtgaagtttg cctgcaagta aagaattgag agtgtgtgca aagcttattt   3300

tcttttatct gggcaaaaat taaaacacat tccttggaac agagctatta cttgcctgtt   3360

ctgtggagaa acttttcttt ttgagggctg tggtgaatgg atgaacgtac atcgtaaaac   3420

tgacaaaata ttttaaaaat atataaaaca caaaattaaa ataaagttgc tggtcagtct   3480

tagtgtttta cagtatttgg gaaaacaact gttacagttt tattgctctg agtaactgac   3540

aaagcagaaa ctattcagtt tttgtagtaa aggcgtcaca tgcaaacaaa caaaatgaat   3600

gaaacagtca aatggtttgc ctcattctcc aagagccaca actcaagctg aactgtgaaa   3660

gtggtttaac actgtatcct aggcgatctt ttttcctcct tctgtttatt tttttgtttg   3720

ttttatttat agtctgattt aaaacaatca gattcaagtt ggttaatttt agttatgtaa   3780

caacctgaca tgatggagga aaacaacctt taaagggatt gtgtctatgg tttgattcac   3840

ttagaaattt tattttctta taacttaagt gcaataaaat gtgttttttc atgtta       3896
```

<210> SEQ ID NO 13
<211> LENGTH: 2124
<212> TYPE: DNA
<213> ORGANISM: Homo sapiens

<400> SEQUENCE: 13

```
atgaatcagg aactgctctc tgtgggcagc aaaagacgac gaactggagg ctctctgaga     60

ggtaaccctt cctcaagcca ggtagatgaa gaacagatga atcgtgtggt agaggaggaa    120

cagcaacagc aactcagaca acaagaggag gagcacactg caaggaatgg tgaagttgtt    180

ggagtagaac ctagacctgg aggccaaaat gattcccagc aaggacagtt ggaagaaaac    240

aataatagat ttatttcggt agatgaggac tcctcaggaa accaagaaga acaagaggaa    300

gatgaagaac atgctggtga acaagatgag gaggatgagg aggaggagga gatggaccag    360

gagagtgacg attttgatca gtctgatgat agtagcagag aagatgaaca tacacatact    420

aacagtgtca cgaactccag tagtattgtg gacctgcccg ttcaccaact ctcctcccca    480

ttctatacaa aaacaacaaa aatgaaaaga aagttggacc atggttctga ggtccgctct    540

ttttctttgg gaaagaaacc atgcaaagtc tcagaatata caagtaccac tgggcttgta    600

ccatgttcag caacaccaac aacttttggg gacctcagag cagccaatgg ccaagggcaa    660

caacgacgcc gaattacatc tgtccagcca cctacaggcc tccaggaatg gctaaaaatg    720

tttcagagct ggagtggacc agagaaattg cttgctttag atgaactcat tgatagttgt    780

gaaccaacac aagtaaaaca tatgatgcaa gtgatagaac cccagtttca acgagacttc    840

atttcattgc tccctaaaga gttggcactc tatgtgcttt cattcctgga acccaaagac    900

ctgctacaag cagctcagac atgtcgctac tggagaattt tggctgaaga caaccttctc    960

tggagagaga aatgcaaaga agaggggatt gatgaaccat tgcacatcaa gagaagaaaa   1020

gtaataaaac caggtttcat acacagtcca tggaaaagtg catacatcag acagcacaga   1080

attgatacta actggaggcg aggagaactc aaatctccta aggtgctgaa aggacatgat   1140

gatcatgtga tcacatgctt acagttttgt ggtaaccgaa tagttagtgg ttctgatgac   1200

aacactttaa aagtttggtc agcagtcaca ggcaaatgtc tgagaacatt agtgggacat   1260
```

-continued acaggtggag tatggtcatc acaaatgaga gacaacatca tcattagtgg atctacagat 1320
cggacactca aagtgtggaa tgcagagact ggagaatgta tacacacctt atatgggcat 1380
acttccactg tgcgttgtat gcatcttcat gaaaaaagag ttgttagcgg ttctcgagat 1440
gccactctta gggtttggga tattgagaca ggccagtgtt tacatgtttt gatgggtcat 1500
gttgcagcag tccgctgtgt tcaatatgat ggcaggaggg ttgttagtgg agcatatgat 1560
tttatggtaa aggtgtggga tccagagact gaaacctgtc tacacacgtt gcaggggcat 1620
actaatagag tctattcatt acagtttgat ggtatccatg tggtgagtgg atctcttgat 1680
acatcaatcc gtgtttggga tgtggagaca gggaattgca ttcacacgtt aacagggcac 1740
cagtcgttaa caagtggaat ggaactcaaa gacaatattc ttgtctctgg gaatgcagat 1800
tctacagtta aaatctggga tatcaaaaca ggacagtgtt tacaaacatt gcaaggtccc 1860
aacaagcatc agagtgctgt gacctgttta cagttcaaca agaactttgt aattaccagc 1920
tcagatgatg gaactgtaaa actatgggac ttgaaaacgg gtgaatttat tcgaaaccta 1980
gtcacattgg agagtggggg gagtggggga gttgtgtggc ggatcagagc ctcaaacaca 2040
aagctggtgt gtgcagttgg gagtcggaat gggactgaag aaaccaagct gctggtgctg 2100
gactttgatg tggacatgaa gtga 2124

<210> SEQ ID NO 14
<211> LENGTH: 707
<212> TYPE: PRT
<213> ORGANISM: Homo sapiens

<400> SEQUENCE: 14

Met Asn Gln Glu Leu Leu Ser Val Gly Ser Lys Arg Arg Arg Thr Gly
1 5 10 15

Gly Ser Leu Arg Gly Asn Pro Ser Ser Ser Gln Val Asp Glu Glu Gln
20 25 30

Met Asn Arg Val Val Glu Glu Glu Gln Gln Gln Gln Leu Arg Gln Gln
35 40 45

Glu Glu Glu His Thr Ala Arg Asn Gly Glu Val Val Gly Val Glu Pro
50 55 60

Arg Pro Gly Gly Gln Asn Asp Ser Gln Gln Gly Gln Leu Glu Glu Asn
65 70 75 80

Asn Asn Arg Phe Ile Ser Val Asp Glu Asp Ser Ser Gly Asn Gln Glu
85 90 95

Glu Gln Glu Glu Asp Glu Glu His Ala Gly Glu Gln Asp Glu Glu Asp
100 105 110

Glu Glu Glu Glu Glu Met Asp Gln Glu Ser Asp Asp Phe Asp Gln Ser
115 120 125

Asp Asp Ser Ser Arg Glu Asp Glu His Thr His Thr Asn Ser Val Thr
130 135 140

Asn Ser Ser Ser Ile Val Asp Leu Pro Val His Gln Leu Ser Ser Pro
145 150 155 160

Phe Tyr Thr Lys Thr Thr Lys Met Lys Arg Lys Leu Asp His Gly Ser
165 170 175

Glu Val Arg Ser Phe Ser Leu Gly Lys Lys Pro Cys Lys Val Ser Glu
180 185 190

Tyr Thr Ser Thr Thr Gly Leu Val Pro Cys Ser Ala Thr Pro Thr Thr
195 200 205

Phe Gly Asp Leu Arg Ala Ala Asn Gly Gln Gly Gln Gln Arg Arg Arg

```
    210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                245                 250                 255

Ile Asp Ser Cys Glu Pro Thr Gln Val Lys His Met Met Gln Val Ile
            260                 265                 270

Glu Pro Gln Phe Gln Arg Asp Phe Ile Ser Leu Leu Pro Lys Glu Leu
        275                 280                 285

Ala Leu Tyr Val Leu Ser Phe Leu Glu Pro Lys Asp Leu Leu Gln Ala
    290                 295                 300

Ala Gln Thr Cys Arg Tyr Trp Arg Ile Leu Ala Glu Asp Asn Leu Leu
305                 310                 315                 320

Trp Arg Glu Lys Cys Lys Glu Glu Gly Ile Asp Glu Pro Leu His Ile
                325                 330                 335

Lys Arg Arg Lys Val Ile Lys Pro Gly Phe Ile His Ser Pro Trp Lys
            340                 345                 350

Ser Ala Tyr Ile Arg Gln His Arg Ile Asp Thr Asn Trp Arg Arg Gly
        355                 360                 365

Glu Leu Lys Ser Pro Lys Val Leu Lys Gly His Asp Asp His Val Ile
    370                 375                 380

Thr Cys Leu Gln Phe Cys Gly Asn Arg Ile Val Ser Gly Ser Asp Asp
385                 390                 395                 400

Asn Thr Leu Lys Val Trp Ser Ala Val Thr Gly Lys Cys Leu Arg Thr
                405                 410                 415

Leu Val Gly His Thr Gly Gly Val Trp Ser Ser Gln Met Arg Asp Asn
            420                 425                 430

Ile Ile Ile Ser Gly Ser Thr Asp Arg Thr Leu Lys Val Trp Asn Ala
        435                 440                 445

Glu Thr Gly Glu Cys Ile His Thr Leu Tyr Gly His Thr Ser Thr Val
    450                 455                 460

Arg Cys Met His Leu His Glu Lys Arg Val Val Ser Gly Ser Arg Asp
465                 470                 475                 480

Ala Thr Leu Arg Val Trp Asp Ile Glu Thr Gly Gln Cys Leu His Val
                485                 490                 495

Leu Met Gly His Val Ala Ala Val Arg Cys Val Gln Tyr Asp Gly Arg
            500                 505                 510

Arg Val Val Ser Gly Ala Tyr Asp Phe Met Val Lys Val Trp Asp Pro
        515                 520                 525

Glu Thr Glu Thr Cys Leu His Thr Leu Gln Gly His Thr Asn Arg Val
    530                 535                 540

Tyr Ser Leu Gln Phe Asp Gly Ile His Val Val Ser Gly Ser Leu Asp
545                 550                 555                 560

Thr Ser Ile Arg Val Trp Asp Val Glu Thr Gly Asn Cys Ile His Thr
                565                 570                 575

Leu Thr Gly His Gln Ser Leu Thr Ser Gly Met Glu Leu Lys Asp Asn
            580                 585                 590

Ile Leu Val Ser Gly Asn Ala Asp Ser Thr Val Lys Ile Trp Asp Ile
        595                 600                 605

Lys Thr Gly Gln Cys Leu Gln Thr Leu Gln Gly Pro Asn Lys His Gln
    610                 615                 620

Ser Ala Val Thr Cys Leu Gln Phe Asn Lys Asn Phe Val Ile Thr Ser
625                 630                 635                 640
```

Ser Asp Asp Gly Thr Val Lys Leu Trp Asp Leu Lys Thr Gly Glu Phe
645 650 655

Ile Arg Asn Leu Val Thr Leu Glu Ser Gly Gly Ser Gly Gly Val Val
660 665 670

Trp Arg Ile Arg Ala Ser Asn Thr Lys Leu Val Cys Ala Val Gly Ser
675 680 685

Arg Asn Gly Thr Glu Glu Thr Lys Leu Leu Val Leu Asp Phe Asp Val
690 695 700

Asp Met Lys
705

<210> SEQ ID NO 15
<211> LENGTH: 2591
<212> TYPE: DNA
<213> ORGANISM: Homo sapiens

<400> SEQUENCE: 15
gatgggattg gggttttccc ctcccatgtg ctcaagactg gcgctaaaag ttttgagctt 60
ctcaaaagtc tagagccacc gtccagggag caggtagctg ctgggctccg gggacacttt 120
gcgttcgggc tgggagcgtg ctttccacga cggtgacacg cttccctgga ttggcagcca 180
gactgccttc cgggtcactg ccatggagga gccgcagtca gatcctagcg tcgagccccc 240
tctgagtcag gaaacatttt cagacctatg gaaactactt cctgaaaaca acgttctgtc 300 cccttgccg tcccaagcaa tggatgattt gatgctgtcc ccggacgata ttgaacaatg 360
gttcactgaa gacccaggtc cagatgaagc tcccagaatg ccagaggctg ctccccccgt 420
ggcccctgca ccagcagctc ctacaccggc ggcccctgca ccagccccct cctggcccct 480
gtcatcttct gtcccttccc agaaaaccta ccagggcagc tacggtttcc gtctgggctt 540
cttgcattct gggacagcca agtctgtgac ttgcacgtac tcccctgccc tcaacaagat 600
gttttgccaa ctggccaaga cctgccctgt gcagctgtgg gttgattcca caccccgcc 660 cggcacccgc gtccgcgcca tggccatcta caagcagtca cagcacatga cggaggttgt 720
gaggcgctgc ccccaccatg agcgctgctc agatagcgat ggtctggccc ctcctcagca 780
tcttatccga gtggaaggaa atttgcgtgt ggagtatttg gatgacagaa acacttttcg 840
acatagtgtg gtggtgccct atgagccgcc tgaggttggc tctgactgta ccaccatcca 900
ctacaactac atgtgtaaca gttcctgcat gggcggcatg aaccggaggc ccatcctcac 960
catcatcaca ctggaagact ccagtggtaa tctactggga cggaacagct ttgaggtgcg 1020
tgtttgtgcc tgtcctggga gagaccggcg cacagaggaa gagaatctcc gcaagaaagg 1080
ggagcctcac cacgagctgc ccccagggag cactaagcga gcactgccca acaacaccag 1140
ctcctctccc cagccaaaga agaaaccact ggatggagaa tatttcaccc ttcagatccg 1200
tgggcgtgag cgcttcgaga tgttccgaga gctgaatgag gccttggaac tcaaggatgc 1260
ccaggctggg aaggagccag gggggagcag ggctcactcc agccacctga agtccaaaaa 1320
gggtcagtct acctcccgcc ataaaaaact catgttcaag acagaagggc ctgactcaga 1380
ctgacattct ccacttcttg ttccccactg acagcctccc acccccatct ctccctcccc 1440
tgccattttg ggttttgggt ctttgaaccc ttgcttgcaa taggtgtgcg tcagaagcac 1500
ccaggacttc catttgcttt gtcccggggc tccactgaac aagttggcct gcactggtgt 1560
tttgttgtgg ggaggaggat ggggagtagg acataccagc ttagatttta aggtttttac 1620
tgtgagggat gtttgggaga tgtaagaaat gttcttgcag ttaagggtta gtttacaatc 1680
agccacattc taggtagggg cccacttcac cgtactaacc agggaagctg tccctcactg 1740
ttgaattttc tctaacttca aggcccatat ctgtgaaatg ctggcatttg cacctacctc 1800
acagagtgca ttgtgagggt taatgaaata atgtacatct ggccttgaaa ccacctttta 1860
ttacatgggg tctagaactt gacccccttg agggtgcttg ttccctctcc ctgttggtcg 1920
gtgggttggt agtttctaca gttgggcagc tggttaggta gagggagttg tcaagtctct 1980
gctggcccag ccaaaccctg tctgacaacc tcttggtgaa ccttagtacc taaaaggaaa 2040
tctcacccca tcccacaccc tggaggattt catctcttgt atatgatgat ctggatccac 2100
caagacttgt tttatgctca gggtcaattt ctttttttctt tttttttttt ttttttcttt 2160
ttctttgaga ctgggtctcg ctttgttgcc caggctggag tggagtggcg tgatcttggc 2220
ttactgcagc ctttgcctcc ccggctcgag cagtcctgcc tcagcctccg gagtagctgg 2280
gaccacaggt tcatgccacc atggccagcc aacttttgca tgttttgtag agatggggtc 2340
tcacagtgtt gcccaggctg gtctcaaact cctgggctca ggcgatccac ctgtctcagc 2400
ctcccagagt gctgggatta caattgtgag ccaccacgtc cagctggaag ggtcaacatc 2460
ttttacattc tgcaagcaca tctgcatttt caccccaccc ttcccctcct tctccctttt 2520
tatatcccat ttttatatcg atctcttatt ttacaataaa actttgctgc cacctgtgtg 2580
tctgaggggt g 2591

<210> SEQ ID NO 16
<211> LENGTH: 1182
<212> TYPE: DNA
<213> ORGANISM: Homo sapiens

<400> SEQUENCE: 16
atggaggagc cgcagtcaga tcctagcgtc gagccccctc tgagtcagga aacattttca 60
gacctatgga aactacttcc tgaaaacaac gttctgtccc ccttgccgtc ccaagcaatg 120
gatgatttga tgctgtcccc ggacgatatt gaacaatggt tcactgaaga cccaggtcca 180
gatgaagctc ccagaatgcc agaggctgct ccccgcgtgg cccctgcacc agcagctcct 240
acaccggcgg cccctgcacc agccccctcc tggcccctgt catcttctgt cccttcccag 300
aaaacctacc agggcagcta cggtttccgt ctgggcttct tgcattctgg gacagccaag 360
tctgtgactt gcacgtactc ccctgccctc aacaagatgt tttgccaact ggccaagacc 420
tgccctgtgc agctgtgggt tgattccaca cccccgcccg gcacccgcgt ccgcgccatg 480
gccatctaca agcagtcaca gcacatgacg gaggttgtga ggcgctgccc ccaccatgag 540
cgctgctcag atagcgatgg tctggcccct cctcagcatc ttatccgagt ggaaggaaat 600
ttgcgtgtgg agtatttgga tgacagaaac acttttcgac atagtgtggt ggtgccctat 660
gagccgcctg aggttggctc tgactgtacc accatccact acaactacat gtgtaacagt 720
tcctgcatgg gcggcatgaa ccggaggccc atcctcacca tcatcacact ggaagactcc 780
agtggtaatc tactgggacg gaacagcttt gaggtgcgtg tttgtgcctg tcctgggaga 840
gaccggcgca cagaggaaga gaatctccgc aagaaagggg agcctcacca cgagctgccc 900
ccagggagca ctaagcgagc actgcccaac aacaccagct cctctcccca gccaaagaag 960
aaaccactgg atggagaata tttcaccctt cagatccgtg ggcgtgagcg cttcgagatg 1020
ttccgagagc tgaatgaggc cttggaactc aaggatgccc aggctgggaa ggagccaggg 1080
gggagcaggg ctcactccag ccacctgaag tccaaaaagg gtcagtctac ctcccgccat 1140
aaaaaactca tgttcaagac agaagggcct gactcagact ga 1182

<210> SEQ ID NO 17
<211> LENGTH: 393
<212> TYPE: PRT
<213> ORGANISM: Homo sapiens

<400> SEQUENCE: 17

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365
```

Leu Lys Ser Lys Lys Gly Gln Ser Thr Ser Arg His Lys Lys Leu Met
370 375 380

Phe Lys Thr Glu Gly Pro Asp Ser Asp
385 390

<210> SEQ ID NO 18
<211> LENGTH: 1267
<212> TYPE: DNA
<213> ORGANISM: Homo sapiens

<400> SEQUENCE: 18
cgagggctgc ttccggctgg tgcccccggg ggagacccaa cctggggcga cttcaggggt 60
gccacattcg ctaagtgctc ggagttaata gcacctcctc cgagcactcg ctcacggcgt 120
ccccttgcct ggaaagatac cgcggtccct ccagaggatt tgagggacag ggtcggaggg 180
ggctcttccg ccagcaccgg aggaagaaag aggaggggct ggctggtcac cagagggtgg 240
ggcggaccgc gtgcgctcgg cggctgcgga gagggggaga gcaggcagcg ggcggcgggg 300
agcagcatgg agccggcggc ggggagcagc atggagcctt cggctgactg gctggccacg 360
gccgcggccc ggggtcgggt agaggaggtg cgggcgctgc tggaggcggg ggcgctgccc 420
aacgcaccga atagttacgg tcggaggccg atccaggtca tgatgatggg cagcgcccga 480
gtggcggagc tgctgctgct ccacggcgcg gagcccaact gcgccgaccc cgccactctc 540
acccgacccg tgcacgacgc tgcccgggag ggcttcctgg acacgctggt ggtgctgcac 600
cgggccgggg cgcggctgga cgtgcgcgat gcctggggcc gtctgcccgt ggacctggct 660
gaggagctgg gccatcgcga tgtcgcacgg tacctgcgcg cggctgcggg gggcaccaga 720
ggcagtaacc atgcccgcat agatgccgcg gaaggtccct cagacatccc cgattgaaag 780
aaccagagag gctctgagaa acctcgggaa acttagatca tcagtcaccg aaggtcctac 840
agggccacaa ctgcccccgc cacaacccac cccgctttcg tagttttcat ttagaaaata 900
gagcttttaa aaatgtcctg ccttttaacg tagatatatg ccttccccca ctaccgtaaa 960
tgtccattta tatcattttt tatatattct tataaaaatg taaaaaagaa aaacaccgct 1020
tctgcctttt cactgtgttg gagttttctg gagtgagcac tcacgcccta agcgcacatt 1080
catgtgggca tttcttgcga gcctcgcagc ctccggaagc tgtcgacttc atgacaagca 1140
ttttgtgaac tagggaagct caggggggtt actggcttct cttgagtcac actgctagca 1200
aatggcagaa ccaaagctca aataaaaata aaataatttt cattcattca ctcaaaaaaa 1260
aaaaaaa 1267

<210> SEQ ID NO 19
<211> LENGTH: 471
<212> TYPE: DNA
<213> ORGANISM: Homo sapiens

<400> SEQUENCE: 19
atggagccgg cggcggggag cagcatggag ccttcggctg actggctggc cacggccgcg 60
gcccggggtc gggtagagga ggtgcgggcg ctgctggagg cgggggcgct gcccaacgca 120
ccgaatagtt acggtcggag gccgatccag gtcatgatga tgggcagcgc ccgagtggcg 180
gagctgctgc tgctccacgg cgcggagccc aactgcgccg accccgccac tctcacccga 240
cccgtgcacg acgctgcccg ggagggcttc ctggacacgc tggtggtgct gcaccgggcc 300
ggggcgcggc tggacgtgcg cgatgcctgg ggccgtctgc ccgtggacct ggctgaggag 360
ctgggccatc gcgatgtcgc acggtacctg cgcgcggctg cggggggcac cagaggcagt 420
aaccatgccc gcatagatgc cgcggaaggt ccctcagaca tccccgattg a 471

<210> SEQ ID NO 20
<211> LENGTH: 156
<212> TYPE: PRT
<213> ORGANISM: Homo sapiens

<400> SEQUENCE: 20

Met Glu Pro Ala Ala Gly Ser Ser Met Glu Pro Ser Ala Asp Trp Leu
1 5 10 15

Ala Thr Ala Ala Ala Arg Gly Arg Val Glu Glu Val Arg Ala Leu Leu
20 25 30

Glu Ala Gly Ala Leu Pro Asn Ala Pro Asn Ser Tyr Gly Arg Arg Pro
35 40 45

Ile Gln Val Met Met Met Gly Ser Ala Arg Val Ala Glu Leu Leu Leu
50 55 60

Leu His Gly Ala Glu Pro Asn Cys Ala Asp Pro Ala Thr Leu Thr Arg
65 70 75 80

Pro Val His Asp Ala Ala Arg Glu Gly Phe Leu Asp Thr Leu Val Val
85 90 95

Leu His Arg Ala Gly Ala Arg Leu Asp Val Arg Asp Ala Trp Gly Arg
100 105 110

Leu Pro Val Asp Leu Ala Glu Glu Leu Gly His Arg Asp Val Ala Arg
115 120 125

Tyr Leu Arg Ala Ala Ala Gly Gly Thr Arg Gly Ser Asn His Ala Arg
130 135 140

Ile Asp Ala Ala Glu Gly Pro Ser Asp Ile Pro Asp
145 150 155

<210> SEQ ID NO 21
<211> LENGTH: 1164
<212> TYPE: DNA
<213> ORGANISM: Homo Sapiens

<400> SEQUENCE: 21
cgctcaggga aggcgggtgc gcgcctgcgg ggcggagatg ggcagggggc ggtgcgtggg 60
tcccagtctg cagttaaggg ggcaggagtg gcgctgctca cctctggtgc caaagggcgg 120
cgcagcggct gccgagctcg gccctggagg cggcgagaac atggtgcgca ggttcttggt 180
gaccctccgg attcggcgcg cgtgcggccc gccgcgagtg agggttttcg tggttcacat 240
cccgcggctc acgggggagt gggcagcgcc aggggcgccc gccgctgtgg ccctcgtgct 300
gatgctactg aggagccagc gtctagggca gcagccgctt cctagaagac caggtcatga 360
tgatgggcag cgcccgagtg gcggagctgc tgctgctcca cggcgcggag cccaactgcg 420
ccgaccccgc cactctcacc cgacccgtgc acgacgctgc ccgggagggc ttcctggaca 480
cgctggtggt gctgcaccgg gccggggcgc ggctggacgt gcgcgatgcc tggggccgtc 540
tgcccgtgga cctggctgag gagctgggcc atcgcgatgt cgcacggtac ctgcgcgcgg 600
ctgcgggggg caccagaggc agtaaccatg cccgcataga tgccgcggaa ggtccctcag 660
acatccccga ttgaaagaac cagagaggct ctgagaaacc tcgggaaact tagatcatca 720
gtcaccgaag gtcctacagg gccacaactg cccccgccac aacccacccc gctttcgtag 780
ttttcattta gaaaatagag cttttaaaaa tgtcctgcct tttaacgtag atatatgcct 840
tcccccacta ccgtaaatgt ccatttatat cattttttat atattcttat aaaaatgtaa 900

-continued

```
aaaagaaaaa caccgcttct gccttttcac tgtgttggag ttttctggag tgagcactca    960

cgccctaagc gcacattcat gtgggcattt cttgcgagcc tcgcagcctc cggaagctgt   1020

cgacttcatg acaagcattt tgtgaactag ggaagctcag gggggttact ggcttctctt   1080

gagtcacact gctagcaaat ggcagaacca aagctcaaat aaaaataaaa taattttcat   1140

tcattcactc aaaaaaaaaa aaaa                                          1164
```

<210> SEQ ID NO 22
<211> LENGTH: 522
<212> TYPE: DNA
<213> ORGANISM: Homo sapiens

<400> SEQUENCE: 22

```
atgggcaggg ggcggtgcgt gggtcccagt ctgcagttaa gggggcagga gtggcgctgc     60

tcacctctgg tgccaaaggg cggcgcagcg gctgccgagc tcggccctgg aggcggcgag    120

aacatggtgc gcaggttctt ggtgaccctc cggattcggc gcgcgtgcgg cccgccgcga    180

gtgagggttt tcgtggttca catcccgcgg ctcacggggg agtgggcagc gccaggggcg    240

cccgccgctg tggccctcgt gctgatgcta ctgaggagcc agcgtctagg gcagcagccg    300

cttcctagaa gaccaggtca tgatgatggg cagcgcccga gtggcggagc tgctgctgct    360

ccacggcgcg gagcccaact gcgccgaccc cgccactctc acccgacccg tgcacgacgc    420

tgcccgggag ggcttcctgg acacgctggt ggtgctgcac cgggccgggg cgcggctgga    480

cgtgcgcgat gcctggggcc gtctgcccgt ggacctggct ga                       522
```

<210> SEQ ID NO 23
<211> LENGTH: 173
<212> TYPE: PRT
<213> ORGANISM: Homo sapiens

<400> SEQUENCE: 23

```
Met Gly Arg Gly Arg Cys Val Gly Pro Ser Leu Gln Leu Arg Gly Gln
1               5                   10                  15

Glu Trp Arg Cys Ser Pro Leu Val Pro Lys Gly Gly Ala Ala Ala Ala
            20                  25                  30

Glu Leu Gly Pro Gly Gly Gly Glu Asn Met Val Arg Arg Phe Leu Val
        35                  40                  45

Thr Leu Arg Ile Arg Arg Ala Cys Gly Pro Pro Arg Val Arg Val Phe
    50                  55                  60

Val Val His Ile Pro Arg Leu Thr Gly Glu Trp Ala Ala Pro Gly Ala
65                  70                  75                  80

Pro Ala Ala Val Ala Leu Val Leu Met Leu Leu Arg Ser Gln Arg Leu
                85                  90                  95

Gly Gln Gln Pro Leu Pro Arg Arg Pro Gly His Asp Asp Gly Gln Arg
            100                 105                 110

Pro Ser Gly Gly Ala Ala Ala Ala Pro Arg Arg Gly Ala Gln Leu Arg
        115                 120                 125

Arg Pro Arg His Ser His Pro Thr Arg Ala Arg Arg Cys Pro Gly Gly
    130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170
```

<210> SEQ ID NO 24

<211> LENGTH: 10740
<212> TYPE: DNA
<213> ORGANISM: Homo sapiens

<400> SEQUENCE: 24
gtattggtgc agcccgccag ggtgtcactg gagacagaat ggaggtgctg ccggactcgg 60
aaatggggtc caagggtagc caaggatggc tgcagcttca tatgatcagt tgttaaagca 120
agttgaggca ctgaagatgg agaactcaaa tcttcgacaa gagctagaag ataattccaa 180
tcatcttaca aaactggaaa ctgaggcatc taatatgaag gaagtactta aacaactaca 240
aggaagtatt gaagatgaag ctatggcttc ttctggacag attgatttat tagagcgtct 300
taaagagctt aacttagata gcagtaattt ccctggagta aaactgcggt caaaaatgtc 360
cctccgttct tatggaagcc gggaaggatc tgtatcaagc cgttctggag agtgcagtcc 420
tgttcctatg ggttcatttc caagaagagg gtttgtaaat ggaagcagag aaagtactgg 480
atatttagaa gaacttgaga aagagaggtc attgcttctt gctgatcttg acaaagaaga 540
aaaggaaaaa gactggtatt acgctcaact tcagaatctc actaaaagaa tagatagtct 600
tcctttaact gaaaattttt ccttacaaac agatatgacc agaaggcaat tggaatatga 660
agcaaggcaa atcagagttg cgatggaaga acaactaggt acctgccagg atatggaaaa 720
acgagcacag cgaagaatag ccagaattca gcaaatcgaa aaggacatac ttcgtatacg 780
acagctttta cagtcccaag caacagaagc agagaggtca tctcagaaca agcatgaaac 840
cggctcacat gatgctgagc ggcagaatga aggtcaagga gtgggagaaa tcaacatggc 900
aacttctggt aatggtcagg gttcaactac acgaatggac catgaaacag ccagtgtttt 960
gagttctagt agcacacact ctgcacctcg aaggctgaca agtcatctgg gaaccaaggt 1020
ggaaatggtg tattcattgt tgtcaatgct tggtactcat gataaggatg atatgtcgcg 1080
aactttgcta gctatgtcta gctcccaaga cagctgtata tccatgcgac agtctggatg 1140
tcttcctctc ctcatccagc ttttacatgg caatgacaaa gactctgtat tgttgggaaa 1200
ttcccggggc agtaaagagg ctcgggccag ggccagtgca gcactccaca acatcattca 1260
ctcacagcct gatgacaaga gaggcaggcg tgaaatccga gtccttcatc ttttggaaca 1320
gatacgcgct tactgtgaaa cctgttggga gtggcaggaa gctcatgaac caggcatgga 1380
ccaggacaaa aatccaatgc cagctcctgt tgaacatcag atctgtcctg ctgtgtgtgt 1440
tctaatgaaa ctttcatttg atgaagagca tagacatgca atgaatgaac taggggggact 1500 acaggccatt gcagaattat tgcaagtgga ctgtgaaatg tatgggctta ctaatgacca 1560
ctacagtatt acactaagac gatatgctgg aatggctttg acaaacttga cttttggaga 1620
tgtagccaac aaggctacgc tatgctctat gaaaggctgc atgagagcac ttgtggccca 1680
actaaaatct gaaagtgaag acttacagca ggttattgcg agtgttttga ggaatttgtc 1740
ttggcgagca gatgtaaata gtaaaaagac gttgcgagaa gttggaagtg tgaaagcatt 1800
gatggaatgt gctttagaag ttaaaaagga atcaaccctc aaaagcgtat tgagtgcctt 1860
atggaatttg tcagcacatt gcactgagaa taaagctgat atatgtgctg tagatggtgc 1920
acttgcattt ttggttggca ctcttactta ccggagccag acaaacactt tagccattat 1980
tgaaagtgga ggtgggatat tacggaatgt gtccagcttg atagctacaa atgaggacca 2040
caggcaaatc ctaagagaga acaactgtct acaaacttta ttacaacact taaaatctca 2100
tagtttgaca atagtcagta atgcatgtgg aactttgtgg aatctctcag caagaaatcc 2160
taaagaccag gaagcattat gggacatggg ggcagttagc atgctcaaga acctcattca 2220

```
ttcaaagcac aaaatgattg ctatgggaag tgctgcagct ttaaggaatc tcatggcaaa   2280
taggcctgcg aagtacaagg atgccaatat tatgtctcct ggctcaagct tgccatctct   2340
tcatgttagg aaacaaaaag ccctagaagc agaattagat gctcagcact tatcagaaac   2400
ttttgacaat atagacaatt taagtcccaa ggcatctcat cgtagtaagc agagacacaa   2460
gcaaagtctc tatggtgatt atgtttttga caccaatcga catgatgata ataggtcaga   2520
caattttaat actggcaaca tgactgtcct ttcaccatat ttgaatacta cagtgttacc   2580
cagctcctct tcatcaagag gaagcttaga tagttctcgt tctgaaaaag atagaagttt   2640
ggagagagaa cgcggaattg gtctaggcaa ctaccatcca gcaacagaaa atccaggaac   2700
ttcttcaaag cgaggtttgc agatctccac cactgcagcc cagattgcca aagtcatgga   2760
agaagtgtca gccattcata cctctcagga agacagaagt tctgggtcta ccactgaatt   2820
acattgtgtg acagatgaga gaaatgcact tagaagaagc tctgctgccc atacacattc   2880
aaacacttac aatttcacta agtcggaaaa ttcaaatagg acatgttcta tgccttatgc   2940
caaattagaa tacaagagat cttcaaatga tagtttaaat agtgtcagta gtagtgatgg   3000
ttatggtaaa agaggtcaaa tgaaaccctc gattgaatcc tattctgaag atgatgaaag   3060
taagttttgc agttatggtc aatacccagc cgacctagcc cataaaatac atagtgcaaa   3120
tcatatggat gataatgatg gagaactaga tacaccaata aattatagtc ttaaatattc   3180
agatgagcag ttgaactctg gaaggcaaag tccttcacag aatgaaagat gggcaagacc   3240
caaacacata atagaagatg aaataaaaca aagtgagcaa agacaatcaa ggaatcaaag   3300
tacaacttat cctgtttata ctgagagcac tgatgataaa cacctcaagt tccaaccaca   3360
ttttggacag caggaatgtg tttctccata caggtcacgg ggagccaatg gttcagaaac   3420
aaatcgagtg ggttctaatc atggaattaa tcaaaatgta agccagtctt tgtgtcaaga   3480
agatgactat gaagatgata agcctaccaa ttatagtgaa cgttactctg aagaagaaca   3540
gcatgaagaa gaagagagac caacaaatta tagcataaaa tataatgaag agaaacgtca   3600
tgtggatcag cctattgatt atagtttaaa atatgccaca gatattcctt catcacagaa   3660
acagtcattt tcattctcaa agagttcatc tggacaaagc agtaaaaccg aacatatgtc   3720
ttcaagcagt gagaatacgt ccacaccttc atctaatgcc aagaggcaga atcagctcca   3780
tccaagttct gcacagagta gaagtggtca gcctcaaaag gctgccactt gcaaagtttc   3840
ttctattaac caagaaacaa tacagactta ttgtgtagaa gatactccaa tatgtttttc   3900
aagatgtagt tcattatcat ctttgtcatc agctgaagat gaaataggat gtaatcagac   3960
gacacaggaa gcagattctg ctaataccct gcaaatagca gaaataaaag aaaagattgg   4020
aactaggtca gctgaagatc ctgtgagcga agttccagca gtgtcacagc accctagaac   4080
caaatccagc agactgcagg gttctagttt atcttcagaa tcagccaggc acaaagctgt   4140
tgaattttct tcaggagcga aatctccctc caaaagtggt gctcagacac ccaaaagtcc   4200
acctgaacac tatgttcagg agaccccact catgtttagc agatgtactt ctgtcagttc   4260
acttgatagt tttgagagtc gttcgattgc cagctccgtt cagagtgaac catgcagtgg   4320
aatggtaagt ggcattataa gccccagtga tcttccagat agccctggac aaaccatgcc   4380
accaagcaga agtaaaacac ctccaccacc tcctcaaaca gctcaaacca agcgagaagt   4440
acctaaaaat aaagcaccta ctgctgaaaa gagagagagt ggacctaagc aagctgcagt   4500
aaatgctgca gttcagaggg tccaggttct tccagatgct gatactttat tacattttgc   4560
```

-continued cacggaaagt actccagatg gattttcttg ttcatccagc ctgagtgctc tgagcctcga 4620
tgagccattt atacagaaag atgtggaatt aagaataatg cctccagttc aggaaaatga 4680
caatgggaat gaaacagaat cagagcagcc taaagaatca aatgaaaacc aagagaaaga 4740
ggcagaaaaa actattgatt ctgaaaagga cctattagat gattcagatg atgatgatat 4800
tgaaatacta gaagaatgta ttatttctgc catgccaaca aagtcatcac gtaaagcaaa 4860
aaagccagcc cagactgctt caaaattacc tccacctgtg gcaaggaaac caagtcagct 4920
gcctgtgtac aaacttctac catcacaaaa caggttgcaa ccccaaaagc atgttagttt 4980
tacaccgggg gatgatatgc cacgggtgta ttgtgttgaa gggacaccta taaacttttc 5040
cacagctaca tctctaagtg atctaacaat cgaatcccct ccaaatgagt tagctgctgg 5100
agaaggagtt agaggagggg cacagtcagg tgaatttgaa aaacgagata ccattcctac 5160
agaaggcaga agtacagatg aggctcaagg aggaaaaacc tcatctgtaa ccatacctga 5220
attggatgac aataaagcag aggaaggtga tattcttgca gaatgcatta attctgctat 5280
gcccaaaggg aaaagtcaca agcctttccg tgtgaaaaag ataatggacc aggtccagca 5340
agcatctgcg tcttcttctg cacccaacaa aaatcagtta gatggtaaga aaaagaaacc 5400
aacttcacca gtaaaaccta taccacaaaa tactgaatat aggacacgtg taagaaaaaa 5460
tgcagactca aaaaataatt taaatgctga gagagttttc tcagacaaca aagattcaaa 5520
gaaacagaat ttgaaaaata attccaaggt cttcaatgat aagctcccaa ataatgaaga 5580
tagagtcaga ggaagttttg cttttgattc acctcatcat tacacgccta ttgaaggaac 5640
tccttactgt ttttcacgaa atgattcttt gagttctcta gattttgatg atgatgatgt 5700
tgacctttcc agggaaaagg ctgaattaag aaaggcaaaa gaaaataagg aatcagaggc 5760
taaagttacc agccacacag aactaacctc caaccaacaa tcagctaata agacacaagc 5820
tattgcaaag cagccaataa atcgaggtca gcctaaaccc atacttcaga aacaatccac 5880
ttttccccag tcatccaaag acataccaga cagaggggca gcaactgatg aaaagttaca 5940
gaattttgct attgaaaata ctccggtttg cttttctcat aattcctctc tgagttctct 6000
cagtgacatt gaccaagaaa acaacaataa agaaaatgaa cctatcaaag agactgagcc 6060
ccctgactca cagggagaac caagtaaacc tcaagcatca ggctatgctc ctaaatcatt 6120
tcatgttgaa gataccccag tttgtttctc aagaaacagt tctctcagtt ctcttagtat 6180
tgactctgaa gatgacctgt tgcaggaatg tataagctcc gcaatgccaa aaaagaaaaa 6240
gccttcaaga ctcaagggtg ataatgaaaa acatagtccc agaaatatgg gtggcatatt 6300
aggtgaagat ctgacacttg atttgaaaga tatacagaga ccagattcag aacatggtct 6360
atcccctgat tcagaaaatt ttgattggaa agctattcag gaaggtgcaa attccatagt 6420
aagtagttta catcaagctg ctgctgctgc atgtttatct agacaagctt cgtctgattc 6480
agattccatc ctttccctga aatcaggaat ctctctggga tcaccatttc atcttacacc 6540
tgatcaagaa gaaaaaccct ttacaagtaa taaaggccca cgaattctaa aaccagggga 6600
gaaaagtaca ttggaaacta aaaagataga atctgaaagt aaaggaatca aaggaggaaa 6660
aaaagtttat aaaagtttga ttactggaaa agttcgatct aattcagaaa tttcaggcca 6720
aatgaaacag ccccttcaag caaacatgcc ttcaatctct cgaggcagga caatgattca 6780
tattccagga gttcgaaata gctcctcaag tacaagtcct gtttctaaaa aaggcccacc 6840
ccttaagact ccagcctcca aaagccctag tgaaggtcaa acagccacca cttctcctag 6900
aggagccaag ccatctgtga aatcagaatt aagccctgtt gccaggcaga catcccaaat 6960

```
aggtgggtca agtaaagcac cttctagatc aggatctaga gattcgaccc cttcaagacc   7020
tgcccagcaa ccattaagta gacctataca gtctcctggc cgaaactcaa tttcccctgg   7080
tagaaatgga ataagtcctc ctaacaaatt atctcaactt ccaaggacat catcccctag   7140
tactgcttca actaagtcct caggttctgg aaaaatgtca tatacatctc caggtagaca   7200
gatgagccaa cagaacctta ccaaacaaac aggtttatcc aagaatgcca gtagtattcc   7260
aagaagtgag tctgcctcca aaggactaaa tcagatgaat aatggtaatg gagccaataa   7320
aaaggtagaa ctttctagaa tgtcttcaac taaatcaagt ggaagtgaat ctgatagatc   7380
agaaagacct gtattagtac gccagtcaac tttcatcaaa gaagctccaa gcccaacctt   7440
aagaagaaaa ttggaggaat ctgcttcatt tgaatctctt tctccatcat ctagaccagc   7500
ttctcccact aggtcccagg cacaaactcc agttttaagt ccttcccttc ctgatatgtc   7560
tctatccaca cattcgtctg ttcaggctgg tggatggcga aaactcccac ctaatctcag   7620
tcccactata gagtataatg atggaagacc agcaaagcgc catgatattg cacggtctca   7680
ttctgaaagt ccttctagac ttccaatcaa taggtcagga acctggaaac gtgagcacag   7740
caaacattca tcatcccttc ctcgagtaag cacttggaga agaactggaa gttcatcttc   7800
aattctttct gcttcatcag aatccagtga aaaagcaaaa agtgaggatg aaaaacatgt   7860
gaactctatt tcaggaacca aacaaagtaa agaaaaccaa gtatccgcaa aaggaacatg   7920
gagaaaaata aaagaaaatg aattttctcc cacaaatagt acttctcaga ccgtttcctc   7980
aggtgctaca aatggtgctg aatcaaagac tctaatttat caaatggcac ctgctgtttc   8040
taaaacagag gatgtttggg tgagaattga ggactgtccc attaacaatc ctagatctgg   8100
aagatctccc acaggtaata ctcccccggt gattgacagt gtttcagaaa aggcaaatcc   8160
aaacattaaa gattcaaaag ataatcaggc aaaacaaaat gtgggtaatg gcagtgttcc   8220
catgcgtacc gtgggtttgg aaaatcgcct gaactccttt attcaggtgg atgcccctga   8280
ccaaaaagga actgagataa aaccaggaca aaataatcct gtccctgtat cagagactaa   8340
tgaaagttct atagtggaac gtaccccatt cagttctagc agctcaagca aacacagttc   8400
acctagtggg actgttgctg ccagagtgac tccttttaat tacaacccaa gccctaggaa   8460
aagcagcgca gatagcactt cagctcggcc atctcagatc ccaactccag tgaataacaa   8520
cacaaagaag cgagattcca aaactgacag cacagaatcc agtggaaccc aaagtcctaa   8580
gcgccattct gggtcttacc ttgtgacatc tgtttaaaag agaggaagaa tgaaactaag   8640
aaaattctat gttaattaca actgctatat agacattttg tttcaaatga aactttaaaa   8700
gactgaaaaa ttttgtaaat aggtttgatt cttgttagag ggtttttgtt ctggaagcca   8760
tatttgatag tatactttgt cttcactggt cttattttgg gaggcactct tgatggttag   8820
gaaaaaaata gtaaagccaa gtatgtttgt acagtatgtt ttacatgtat ttaaagtagc   8880
atcccatccc aacttccttt aattattgct tgtcttaaaa taatgaacac tacagataga   8940
aaatatgata tattgctgtt atcaatcatt tctagattat aaactgacta aacttacatc   9000
agggaaaaat tggtatttat gcaaaaaaaa atgtttttgt ccttgtgagt ccatctaaca   9060
tcataattaa tcatgtggct gtgaaattca cagtaatatg gttcccgatg aacaagttta   9120
cccagcctgc tttgctttac tgcatgaatg aaactgatgg ttcaatttca gaagtaatga   9180
ttaacagtta tgtggtcaca tgatgtgcat agagatagct acagtgtaat aatttacact   9240
attttgtgct ccaaacaaaa caaaaatctg tgtaactgta aaacattgaa tgaaactatt   9300
```

ttacctgaac tagattttat ctgaaagtag gtagaatttt tgctatgctg taatttgttg 9360
tatattctgg tatttgaggt gagatggctg ctcttttatt aatgagacat gaattgtgtc 9420
tcaacagaaa ctaaatgaac atttcagaat aaattattgc tgtatgtaaa ctgttactga 9480
aattggtatt tgtttgaagg gtcttgtttc acatttgtat taataattgt ttaaaatgcc 9540
tcttttaaaa gcttatataa attttttttct tcagcttcta tgcattaaga gtaaaattcc 9600
tcttactgta ataaaaacaa ttgaagaaga ctgttgccac ttaaccattc catgcgttgg 9660
cacttatcta ttcctgaaat ttcttttatg tgattagctc atcttgattt ttaatatttt 9720
tccacttaaa cttttttttc ttactccact ggagctcagt aaaagtaaat tcatgtaata 9780
gcaatgcaag cagcctagca cagactaagc attgagcata ataggcccac ataatttcct 9840
ctttcttaat attatagaat tctgtacttg aaattgattc ttagacattg cagtctcttc 9900
gaggctttac agtgtaaact gtcttgcccc ttcatcttct tgttgcaact gggtctgaca 9960
tgaacacttt ttatcaccct gtatgttagg gcaagatctc agcagtgaag tataatcagc 10020
actttgccat gctcagaaaa ttcaaatcac atggaacttt agaggtagat ttaatacgat 10080
taagatattc agaagtatat tttagaatcc ctgcctgtta aggaaacttt atttgtggta 10140
ggtacagttc tggggtacat gttaagtgtc cccttataca gtggagggaa gtcttccttc 10200
ctgaaggaaa ataaactgac acttattaac taagataatt tacttaatat atcttccctg 10260
atttgtttta aaagatcaga gggtgactga tgatacatgc atacatattt gttgaataaa 10320
tgaaaattta tttttagtga taagattcat acactctgta tttggggagg gaaaaccttt 10380
ttaagcatgg tggggcactc agataggagt gaatacacct acctggtgcc ttgaaaatca 10440
catcaagtag ttaattatct accccttacc tgtgtttata acttccaggt aatgagaatg 10500
atttttttta aagctaaaat gccagtaaat aaaagtgcta tgacttgagc taagatattt 10560
gactccaatg cctgtactgt gtctactgca ccactttgta aacacttcaa tttactatct 10620
ttgaaatgat tgacctttaa atttttgcca aatgttatct gaaattgtct atgaatacca 10680
tctacttctg ttgttttccc aggcttccat aaacaatgga gatacatgca aaaaaaaaaa 10740

<210> SEQ ID NO 25
<211> LENGTH: 8532
<212> TYPE: DNA
<213> ORGANISM: Homo sapiens

<400> SEQUENCE: 25
atggctgcag cttcatatga tcagttgtta aagcaagttg aggcactgaa gatggagaac 60
tcaaatcttc gacaagagct agaagataat tccaatcatc ttacaaaact ggaaactgag 120
gcatctaata tgaaggaagt acttaaacaa ctacaaggaa gtattgaaga tgaagctatg 180
gcttcttctg gacagattga tttattagag cgtcttaaag agcttaactt agatagcagt 240
aatttccctg gagtaaaact gcggtcaaaa atgtccctcc gttcttatgg aagccgggaa 300
ggatctgtat caagccgttc tggagagtgc agtcctgttc ctatgggttc atttccaaga 360
agagggtttg taaatggaag cagagaaagt actggatatt tagaagaact tgagaaagag 420
aggtcattgc ttcttgctga tcttgacaaa gaagaaaagg aaaaagactg gtattacgct 480
caacttcaga atctcactaa aagaatagat agtcttcctt taactgaaaa tttttcctta 540
caaacagata tgaccagaag gcaattggaa tatgaagcaa ggcaaatcag agttgcgatg 600
gaagaacaac taggtacctg ccaggatatg gaaaaacgag cacagcgaag aatagccaga 660
attcagcaaa tcgaaaagga catacttcgt atacgacagc ttttacagtc ccaagcaaca 720

-continued

```
gaagcagaga ggtcatctca gaacaagcat gaaaccggct cacatgatgc tgagcggcag    780
aatgaaggtc aaggagtggg agaaatcaac atggcaactt ctggtaatgg tcagggttca    840
actacacgaa tggaccatga aacagccagt gttttgagtt ctagtagcac acactctgca    900
cctcgaaggc tgacaagtca tctgggaacc aaggtggaaa tggtgtattc attgttgtca    960
atgcttggta ctcatgataa ggatgatatg tcgcgaactt tgctagctat gtctagctcc   1020
caagacagct gtatatccat gcgacagtct ggatgtcttc ctctcctcat ccagctttta   1080
catggcaatg acaaagactc tgtattgttg ggaaattccc ggggcagtaa agaggctcgg   1140
gccagggcca gtgcagcact ccacaacatc attcactcac agcctgatga caagagaggc   1200
aggcgtgaaa tccgagtcct tcatcttttg gaacagatac gcgcttactg tgaaacctgt   1260
tgggagtggc aggaagctca tgaaccaggc atggaccagg acaaaaatcc aatgccagct   1320
cctgttgaac atcagatctg tcctgctgtg tgtgttctaa tgaaactttc atttgatgaa   1380
gagcatagac atgcaatgaa tgaactaggg ggactacagg ccattgcaga attattgcaa   1440
gtggactgtg aaatgtacgg gcttactaat gaccactaca gtattacact aagacgatat   1500
gctggaatgg ctttgacaaa cttgactttt ggagatgtag ccaacaaggc tacgctatgc   1560
tctatgaaag gctgcatgag agcacttgtg gcccaactaa aatctgaaag tgaagactta   1620
cagcaggtta ttgcaagtgt tttgaggaat ttgtcttggc gagcagatgt aaatagtaaa   1680
aagacgttgc gagaagttgg aagtgtgaaa gcattgatgg aatgtgcttt agaagttaaa   1740
aaggaatcaa ccctcaaaag cgtattgagt gccttatgga atttgtcagc acattgcact   1800
gagaataaag ctgatatatg tgctgtagat ggtgcacttg catttttggt tggcactctt   1860
acttaccgga gccagacaaa cactttagcc attattgaaa gtggaggtgg gatattacgg   1920
aatgtgtcca gcttgatagc tacaaatgag gaccacaggc aaatcctaag agagaacaac   1980
tgtctacaaa ctttattaca acacttaaaa tctcatagtt tgacaatagt cagtaatgca   2040
tgtggaactt tgtggaatct ctcagcaaga aatcctaaag accaggaagc attatgggac   2100
atgggggcag ttagcatgct caagaacctc attcattcaa agcacaaaat gattgctatg   2160
ggaagtgctg cagctttaag gaatctcatg gcaaataggc ctgcgaagta caaggatgcc   2220
aatattatgt ctcctggctc aagcttgcca tctcttcatg ttaggaaaca aaaagcccta   2280
gaagcagaat tagatgctca gcacttatca gaaacttttg acaatataga caatttaagt   2340
cccaaggcat ctcatcgtag taagcagaga cacaagcaaa gtctctatgg tgattatgtt   2400
tttgacacca atcgacatga tgataatagg tcagacaatt ttaatactgg caacatgact   2460
gtcctttcac catatttgaa tactacagtg ttacccagct cctcttcatc aagaggaagc   2520
ttagatagtt ctcgttctga aaaagataga agtttggaga gagaacgcgg aattggtcta   2580
ggcaactacc atccagcaac agaaaatcca ggaacttctt caaagcgagg tttgcagatc   2640
tccaccactg cagcccagat tgccaaagtc atggaagaag tgtcagccat tcatacctct   2700
caggaagaca gaagttctgg gtctaccact gaattacatt gtgtgacaga tgagagaaat   2760
gcacttagaa gaagctctgc tgcccataca cattcaaaca cttacaattt cactaagtcg   2820
gaaaattcaa ataggacatg ttctatgcct tatgccaaat tagaatacaa gagatcttca   2880
aatgatagtt taaatagtgt cagtagtagt gatggttatg gtaaaagagg tcaaatgaaa   2940
ccctcgattg aatcctattc tgaagatgat gaaagtaagt tttgcagtta tggtcaatac   3000
ccagccgacc tagcccataa aatacatagt gcaaatcata tggatgataa tgatggagaa   3060
```

```
ctagatacac caataaatta tagtcttaaa tattcagatg agcagttgaa ctctggaagg   3120
caaagtcctt cacagaatga aagatgggca agacccaaac acataataga agatgaaata   3180
aaacaaagtg agcaaagaca atcaaggaat caaagtacaa cttatcctgt ttatactgag   3240
agcactgatg ataaacacct caagttccaa ccacattttg gacagcagga atgtgtttct   3300
ccatacaggt cacggggagc caatggttca gaaacaaatc gagtgggttc taatcatgga   3360
attaatcaaa atgtaagcca gtctttgtgt caagaagatg actatgaaga tgataagcct   3420
accaattata gtgaacgtta ctctgaagaa gaacagcatg aagaagaaga gagaccaaca   3480
aattatagca taaaatataa tgaagagaaa cgtcatgtgg atcagcctat tgattatagt   3540
ttaaaatatg ccacagatat tccttcatca cagaaacagt cattttcatt ctcaaagagt   3600
tcatctggac aaagcagtaa aaccgaacat atgtcttcaa gcagtgagaa tacgtccaca   3660
ccttcatcta atgccaagag gcagaatcag ctccatccaa gttctgcaca gagtagaagt   3720
ggtcagcctc aaaaggctgc cacttgcaaa gtttcttcta ttaaccaaga aacaatacag   3780
acttattgtg tagaagatac tccaatatgt tttcaagat gtagttcatt atcatctttg    3840
tcatcagctg aagatgaaat aggatgtaat cagacgacac aggaagcaga ttctgctaat   3900
accctgcaaa tagcagaaat aaaagaaaag attggaacta ggtcagctga agatcctgtg   3960
agcgaagttc cagcagtgtc acagcaccct agaaccaaat ccagcagact gcagggttct   4020
agtttatctt cagaatcagc caggcacaaa gctgttgaat tttcttcagg agcgaaatct   4080
ccctccaaaa gtggtgctca gacacccaaa agtccacctg aacactatgt tcaggagacc   4140
ccactcatgt ttagcagatg tacttctgtc agttcacttg atagttttga gagtcgttcg   4200
attgccagct ccgttcagag tgaaccatgc agtggaatgg taagtggcat tataagcccc   4260
agtgatcttc cagatagccc tggacaaacc atgccaccaa gcagaagtaa aacacctcca   4320
ccacctcctc aaacagctca aaccaagcga gaagtaccta aaaataaagc acctactgct   4380
gaaaagagag agagtggacc taagcaagct gcagtaaatg ctgcagttca gagggtccag   4440
gttcttccag atgctgatac tttattacat tttgccacgg aaagtactcc agatggattt   4500
tcttgttcat ccagcctgag tgctctgagc ctcgatgagc catttataca gaaagatgtg   4560
gaattaagaa taatgcctcc agttcaggaa aatgacaatg ggaatgaaac agaatcagag   4620
cagcctaaag aatcaaatga aaaccaagag aaagaggcag aaaaaactat tgattctgaa   4680
aaggacctat tagatgattc agatgatgat gatattgaaa tactagaaga atgtattatt   4740
tctgccatgc caacaaagtc atcacgtaaa gcaaaaaagc cagcccagac tgcttcaaaa   4800
ttacctccac ctgtggcaag gaaaccaagt cagctgcctg tgtacaaact tctaccatca   4860
caaaacaggt tgcaacccca aaagcatgtt agttttacac cggggggatga tatgccacgg  4920
gtgtattgtg ttgaagggac acctataaac ttttccacag ctacatctct aagtgatcta   4980
acaatcgaat cccctccaaa tgagttagct gctggagaag gagttagagg aggagcacag   5040
tcaggtgaat ttgaaaaacg agataccatt cctacagaag gcagaagtac agatgaggct   5100
caaggaggaa aaacctcatc tgtaaccata cctgaattgg atgacaataa agcagaggaa   5160
ggtgatattc ttgcagaatg cattaattct gctatgccca aagggaaaag tcacaagcct   5220
ttccgtgtga aaaagataat ggaccaggtc cagcaagcat ctgcgtcgtc ttctgcaccc   5280
aacaaaaatc agttagatgg taagaaaaag aaaccaactt caccagtaaa acctatacca   5340
caaaatactg aatataggac acgtgtaaga aaaaatgcag actcaaaaaa taatttaaat   5400
gctgagagag ttttctcaga caacaaagat tcaaagaaac agaatttgaa aaataattcc   5460
```

```
aaggacttca atgataagct cccaaataat gaagatagag tcagaggaag ttttgctttt   5520
gattcacctc atcattacac gcctattgaa ggaactcctt actgtttttc acgaaatgat   5580
tctttgagtt ctctagattt tgatgatgat gatgttgacc tttccaggga aaaggctgaa   5640
ttaagaaagg caaaagaaaa taaggaatca gaggctaaag ttaccagcca cacagaacta   5700
acctccaacc aacaatcagc taataagaca caagctattg caaagcagcc aataaatcga   5760
ggtcagccta aacccatact tcagaaacaa tccacttttc cccagtcatc caaagacata   5820
ccagacagag ggcagcaac tgatgaaaag ttacagaatt ttgctattga aaatactcca    5880
gtttgctttt ctcataattc ctctctgagt tctctcagtg acattgacca agaaaacaac   5940
aataaagaaa atgaacctat caaagagact gagccccctg actcacaggg agaaccaagt   6000
aaacctcaag catcaggcta tgctcctaaa tcatttcatg ttgaagatac cccagtttgt   6060
ttctcaagaa acagttctct cagttctctt agtattgact ctgaagatga cctgttgcag   6120
gaatgtataa gctccgcaat gccaaaaaag aaaaagcctt caagactcaa gggtgataat   6180
gaaaaacata gtcccagaaa tatgggtggc atattaggtg aagatctgac acttgatttg   6240
aaagatatac agagaccaga ttcagaacat ggtctatccc ctgattcaga aaattttgat   6300
tggaaagcta ttcaggaagg tgcaaattcc atagtaagta gtttacatca agctgctgct   6360
gctgcatgtt tatctagaca agcttcgtct gattcagatt ccatcctttc cctgaaatca   6420
ggaatctctc tgggatcacc atttcatctt acacctgatc aagaagaaaa accctttaca   6480
agtaataaag gcccacgaat tctaaaacca ggggagaaaa gtacattgga aactaaaaag   6540
atagaatctg aaagtaaagg aatcaaagga ggaaaaaaag tttataaaag tttgattact   6600
ggaaaagttc gatctaattc agaaatttca ggccaaatga aacagcccct tcaagcaaac   6660
atgccttcaa tctctcgagg caggacaatg attcatattc caggagttcg aaatagctcc   6720
tcaagtacaa gtcctgtttc taaaaaaggc ccaccccctta agactccagc ctccaaaagc  6780
cctagtgaag gtcaaacagc caccacttct cctagaggag ccaagccatc tgtgaaatca   6840
gaattaagcc ctgttgccag gcagacatcc caaataggtg ggtcaagtaa agcaccttct   6900
agatcaggat ctagagattc gaccccttca agacctgccc agcaaccatt aagtagacct   6960
atacagtctc ctggccgaaa ctcaatttcc cctggtagaa atggaataag tcctcctaac   7020
aaattatctc aacttccaag gacatcatcc cctagtactg cttcaactaa gtcctcaggt   7080
tctggaaaaa tgtcatatac atctccaggt agacagatga gccaacagaa ccttaccaaa   7140
caaacaggtt tatccaagaa tgccagtagt attccaagaa gtgagtctgc ctccaaagga   7200
ctaaatcaga tgaataatgg taatggagcc aataaaaagg tagaactttc tagaatgtct   7260
tcaactaaat caagtggaag tgaatctgat agatcagaaa gacctgtatt agtacgccag   7320
tcaactttca tcaaagaagc tccaagccca accttaagaa gaaaattgga ggaatctgct   7380
tcatttgaat ctctttctcc atcatctaga ccagcttctc ccactaggtc ccaggcacaa   7440
actccagttt taagtccttc ccttcctgat atgtctctat ccacacattc gtctgttcag   7500
gctggtggat ggcgaaaact cccacctaat ctcagtccca ctatagagta taatgatgga   7560
agaccagcaa agcgccatga tattgcacgg tctcattctg aaagtccttc tagacttcca   7620
atcaataggt caggaacctg gaaacgtgag cacagcaaac attcatcatc ccttcctcga   7680
gtaagcactt ggagaagaac tggaagttca tcttcaattc tttctgcttc atcagaatcc   7740
agtgaaaaag caaaaagtga ggatgaaaaa catgtgaact ctatttcagg aaccaaacaa   7800
```

agtaaagaaa accaagtatc cgcaaaagga acatggagaa aaataaaaga aaatgaattt 7860
tctcccacaa atagtacttc tcagaccgtt tcctcaggtg ctacaaatgg tgctgaatca 7920
aagactctaa tttatcaaat ggcacctgct gtttctaaaa cagaggatgt ttgggtgaga 7980
attgaggact gtcccattaa caatcctaga tctggaagat ctcccacagg taatactccc 8040
ccggtgattg acagtgtttc agaaaaggca aatccaaaca ttaaagattc aaaagataat 8100
caggcaaaac aaaatgtggg taatggcagt gttcccatgc gtaccgtggg tttggaaaat 8160
cgcctgaact cctttattca ggtggatgcc cctgaccaaa aaggaactga gataaaacca 8220
ggacaaaata atcctgtccc tgtatcagag actaatgaaa gttctatagt ggaacgtacc 8280
ccattcagtt ctagcagctc aagcaaacac agttcaccta gtgggactgt tgctgccaga 8340
gtgactcctt ttaattacaa cccaagccct aggaaaagca gcgcagatag cacttcagct 8400
cggccatctc agatcccaac tccagtgaat aacaacacaa agaagcgaga ttccaaaact 8460
gacagcacag aatccagtgg aacccaaagt cctaagcgcc attctgggtc ttaccttgtg 8520
acatctgttt aa 8532

<210> SEQ ID NO 26
<211> LENGTH: 2843
<212> TYPE: PRT
<213> ORGANISM: Homo sapiens

<400> SEQUENCE: 26

Met Ala Ala Ala Ser Tyr Asp Gln Leu Leu Lys Gln Val Glu Ala Leu
1 5 10 15

Lys Met Glu Asn Ser Asn Leu Arg Gln Glu Leu Glu Asp Asn Ser Asn
20 25 30

His Leu Thr Lys Leu Glu Thr Glu Ala Ser Asn Met Lys Glu Val Leu
35 40 45

Lys Gln Leu Gln Gly Ser Ile Glu Asp Glu Ala Met Ala Ser Ser Gly
50 55 60

Gln Ile Asp Leu Leu Glu Arg Leu Lys Glu Leu Asn Leu Asp Ser Ser
65 70 75 80

Asn Phe Pro Gly Val Lys Leu Arg Ser Lys Met Ser Leu Arg Ser Tyr
85 90 95

Gly Ser Arg Glu Gly Ser Val Ser Ser Arg Ser Gly Glu Cys Ser Pro
100 105 110

Val Pro Met Gly Ser Phe Pro Arg Arg Gly Phe Val Asn Gly Ser Arg
115 120 125

Glu Ser Thr Gly Tyr Leu Glu Glu Leu Glu Lys Glu Arg Ser Leu Leu
130 135 140

Leu Ala Asp Leu Asp Lys Glu Glu Lys Glu Lys Asp Trp Tyr Tyr Ala
145 150 155 160

Gln Leu Gln Asn Leu Thr Lys Arg Ile Asp Ser Leu Pro Leu Thr Glu
165 170 175

Asn Phe Ser Leu Gln Thr Asp Met Thr Arg Arg Gln Leu Glu Tyr Glu
180 185 190

Ala Arg Gln Ile Arg Val Ala Met Glu Glu Gln Leu Gly Thr Cys Gln
195 200 205

Asp Met Glu Lys Arg Ala Gln Arg Arg Ile Ala Arg Ile Gln Gln Ile
210 215 220

Glu Lys Asp Ile Leu Arg Ile Arg Gln Leu Leu Gln Ser Gln Ala Thr
225 230 235 240

```
Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400

Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu Glu His Arg His
    450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
    530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                565                 570                 575

Leu Glu Val Lys Lys Glu Ser Thr Leu Lys Ser Val Leu Ser Ala Leu
            580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
    610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                645                 650                 655

Arg Glu Asn Asn Cys Leu Gln Thr Leu Leu Gln His Leu Lys Ser His
```

-continued

```
            660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
    690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
    770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
            820                 825                 830

Ser Ser Ser Ser Ser Arg Gly Ser Leu Asp Ser Ser Arg Ser Glu Lys
        835                 840                 845

Asp Arg Ser Leu Glu Arg Glu Arg Gly Ile Gly Leu Gly Asn Tyr His
    850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
                885                 890                 895

Ile His Thr Ser Gln Glu Asp Arg Ser Ser Gly Ser Thr Thr Glu Leu
            900                 905                 910

His Cys Val Thr Asp Glu Arg Asn Ala Leu Arg Arg Ser Ser Ala Ala
        915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
        995                 1000                1005

His Ser Ala Asn His Met Asp Asp Asn Asp Gly Glu Leu Asp Thr Pro
    1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
            1060                1065                1070

Thr Thr Tyr Pro Val Tyr Thr Glu Ser Thr Asp Asp Lys His Leu Lys
        1075                1080                1085
```

```
Phe Gln Pro His Phe Gly Gln Gln Glu Cys Val Ser Pro Tyr Arg Ser
    1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
            1140                1145                1150

His Glu Glu Glu Glu Arg Pro Thr Asn Tyr Ser Ile Lys Tyr Asn Glu
        1155                1160                1165

Glu Lys Arg His Val Asp Gln Pro Ile Asp Tyr Ser Leu Lys Tyr Ala
    1170                1175                1180

Thr Asp Ile Pro Ser Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
            1220                1225                1230

Pro Ser Ser Ala Gln Ser Arg Ser Gly Gln Pro Gln Lys Ala Ala Thr
        1235                1240                1245

Cys Lys Val Ser Ser Ile Asn Gln Glu Thr Ile Gln Thr Tyr Cys Val
    1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Glu Lys Ile Gly
            1300                1305                1310

Thr Arg Ser Ala Glu Asp Pro Val Ser Glu Val Pro Ala Val Ser Gln
        1315                1320                1325

His Pro Arg Thr Lys Ser Ser Arg Leu Gln Gly Ser Ser Leu Ser Ser
    1330                1335                1340

Glu Ser Ala Arg His Lys Ala Val Glu Phe Ser Ser Gly Ala Lys Ser
1345                1350                1355                1360

Pro Ser Lys Ser Gly Ala Gln Thr Pro Lys Ser Pro Pro Glu His Tyr
                1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
        1395                1400                1405

Pro Cys Ser Gly Met Val Ser Gly Ile Ile Ser Pro Ser Asp Leu Pro
    1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
                1445                1450                1455

Ala Pro Thr Ala Glu Lys Arg Glu Ser Gly Pro Lys Gln Ala Ala Val
            1460                1465                1470

Asn Ala Ala Val Gln Arg Val Gln Val Leu Pro Asp Ala Asp Thr Leu
        1475                1480                1485

Leu His Phe Ala Thr Glu Ser Thr Pro Asp Gly Phe Ser Cys Ser Ser
    1490                1495                1500
```

-continued

```
Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
                1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Glu Lys Asp Leu Leu Asp Asp Ser Asp
        1555                1560                1565

Asp Asp Asp Ile Glu Ile Leu Glu Glu Cys Ile Ile Ser Ala Met Pro
    1570                1575                1580

Thr Lys Ser Ser Arg Lys Ala Lys Lys Pro Ala Gln Thr Ala Ser Lys
1585                1590                1595                1600

Leu Pro Pro Pro Val Ala Arg Lys Pro Ser Gln Leu Pro Val Tyr Lys
                1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
        1635                1640                1645

Ile Asn Phe Ser Thr Ala Thr Ser Leu Ser Asp Leu Thr Ile Glu Ser
    1650                1655                1660

Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
                1685                1690                1695

Thr Asp Glu Ala Gln Gly Gly Lys Thr Ser Ser Val Thr Ile Pro Glu
            1700                1705                1710

Leu Asp Asp Asn Lys Ala Glu Glu Gly Asp Ile Leu Ala Glu Cys Ile
        1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Lys Pro Thr Ser Pro Val
                1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Val Phe Asn
    1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
                1845                1850                1855

Ser Arg Asn Asp Ser Leu Ser Ser Leu Asp Phe Asp Asp Asp Asp Val
            1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
    1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
```

-continued

```
                1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
        1955                1960                1965

Leu Ser Ser Leu Ser Asp Ile Asp Gln Glu Asn Asn Asn Lys Glu Asn
    1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
                2005                2010                2015

Thr Pro Val Cys Phe Ser Arg Asn Ser Ser Leu Ser Ser Leu Ser Ile
            2020                2025                2030

Asp Ser Glu Asp Asp Leu Leu Gln Glu Cys Ile Ser Ser Ala Met Pro
        2035                2040                2045

Lys Lys Lys Lys Pro Ser Arg Leu Lys Gly Asp Asn Glu Lys His Ser
    2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
                2085                2090                2095

Glu Asn Phe Asp Trp Lys Ala Ile Gln Glu Gly Ala Asn Ser Ile Val
            2100                2105                2110

Ser Ser Leu His Gln Ala Ala Ala Ala Ala Cys Leu Ser Arg Gln Ala
        2115                2120                2125

Ser Ser Asp Ser Asp Ser Ile Leu Ser Leu Lys Ser Gly Ile Ser Leu
    2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
                2165                2170                2175

Glu Thr Lys Lys Ile Glu Ser Glu Ser Lys Gly Ile Lys Gly Gly Lys
            2180                2185                2190

Lys Val Tyr Lys Ser Leu Ile Thr Gly Lys Val Arg Ser Asn Ser Glu
        2195                2200                2205

Ile Ser Gly Gln Met Lys Gln Pro Leu Gln Ala Asn Met Pro Ser Ile
    2210                2215                2220

Ser Arg Gly Arg Thr Met Ile His Ile Pro Gly Val Arg Asn Ser Ser
2225                2230                2235                2240

Ser Ser Thr Ser Pro Val Ser Lys Lys Gly Pro Pro Leu Lys Thr Pro
                2245                2250                2255

Ala Ser Lys Ser Pro Ser Glu Gly Gln Thr Ala Thr Thr Ser Pro Arg
            2260                2265                2270

Gly Ala Lys Pro Ser Val Lys Ser Glu Leu Ser Pro Val Ala Arg Gln
        2275                2280                2285

Thr Ser Gln Ile Gly Gly Ser Ser Lys Ala Pro Ser Arg Ser Gly Ser
    2290                2295                2300

Arg Asp Ser Thr Pro Ser Arg Pro Ala Gln Gln Pro Leu Ser Arg Pro
2305                2310                2315                2320

Ile Gln Ser Pro Gly Arg Asn Ser Ile Ser Pro Gly Arg Asn Gly Ile
                2325                2330                2335

Ser Pro Pro Asn Lys Leu Ser Gln Leu Pro Arg Thr Ser Ser Pro Ser
            2340                2345                2350
```

-continued

```
Thr Ala Ser Thr Lys Ser Ser Gly Ser Gly Lys Met Ser Tyr Thr Ser
        2355                2360                2365

Pro Gly Arg Gln Met Ser Gln Gln Asn Leu Thr Lys Gln Thr Gly Leu
    2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
                2405                2410                2415

Ser Arg Met Ser Ser Thr Lys Ser Ser Gly Ser Glu Ser Asp Arg Ser
            2420                2425                2430

Glu Arg Pro Val Leu Val Arg Gln Ser Thr Phe Ile Lys Glu Ala Pro
        2435                2440                2445

Ser Pro Thr Leu Arg Arg Lys Leu Glu Glu Ser Ala Ser Phe Glu Ser
    2450                2455                2460

Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
                2485                2490                2495

Ser Ser Val Gln Ala Gly Gly Trp Arg Lys Leu Pro Pro Asn Leu Ser
            2500                2505                2510

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Ser Leu Pro Arg
2545                2550                2555                2560

Val Ser Thr Trp Arg Arg Thr Gly Ser Ser Ser Ser Ile Leu Ser Ala
                2565                2570                2575

Ser Ser Glu Ser Ser Glu Lys Ala Lys Ser Glu Asp Glu Lys His Val
            2580                2585                2590

Asn Ser Ile Ser Gly Thr Lys Gln Ser Lys Glu Asn Gln Val Ser Ala
        2595                2600                2605

Lys Gly Thr Trp Arg Lys Ile Lys Glu Asn Glu Phe Ser Pro Thr Asn
    2610                2615                2620

Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
                2645                2650                2655

Val Trp Val Arg Ile Glu Asp Cys Pro Ile Asn Asn Pro Arg Ser Gly
            2660                2665                2670

Arg Ser Pro Thr Gly Asn Thr Pro Pro Val Ile Asp Ser Val Ser Glu
        2675                2680                2685

Lys Ala Asn Pro Asn Ile Lys Asp Ser Lys Asp Asn Gln Ala Lys Gln
    2690                2695                2700

Asn Val Gly Asn Gly Ser Val Pro Met Arg Thr Val Gly Leu Glu Asn
2705                2710                2715                2720

Arg Leu Asn Ser Phe Ile Gln Val Asp Ala Pro Asp Gln Lys Gly Thr
                2725                2730                2735

Glu Ile Lys Pro Gly Gln Asn Asn Pro Val Pro Val Ser Glu Thr Asn
            2740                2745                2750

Glu Ser Ser Ile Val Glu Arg Thr Pro Phe Ser Ser Ser Ser Ser Ser
        2755                2760                2765
```

-continued

```
Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
                2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val
        2835                2840
```

BIOMARKERS OF RESPONSE TO NAE INHIBITORS

RELATED APPLICATIONS

This application is a continuation of U.S. patent application Ser. No. 14/354,155 filed Apr. 25, 2014, which is a national phase entry of PCT/US2012/062263, filed Oct. 26, 2012, which claims priority to U.S. Provisional Application No. 61/552,686 filed on Oct. 28, 2011. The entire contents of the foregoing application are incorporated herein by reference.

SEQUENCE LISTING

This application contains a Sequence Listing which is submitted herewith in electronically readable format. The Sequence Listing file was created on Oct. 26, 2012, is named "sequencelisting.txt," and its size is 149 kb (153,088 bytes). The entire contents of the Sequence Listing in the sequencelisting.txt file are incorporated herein by this reference.

BACKGROUND

Cells become cancerous when their genotype or phenotype alters in a way that there is uncontrolled growth that is not subject to the confines of the normal tissue environment. One or more genes is mutated, amplified, deleted, overexpressed or underexpressed. Chromosome portions can be lost or moved from one location to another. Some cancers have characteristic patterns by which genotypes or phenotypes are altered.

Many genes have mutations which are associated with cancer. Some genes have multiple sites where mutations can occur. Many cancers have mutations in and/or mis-expression of more than one gene. Gene mutations can facilitate tumor progression, tumor growth rate or whether a tumor will metastasize. Some mutations can affect whether a tumor cell will respond to therapy.

A variety of agents treat cancers. Cancers of the blood and bone marrow often are treated with steroids/glucocorticoids, imids, proteasome inhibitors and alkylating agents. Cancers of other tissues often are treated with alkylating agents, topoisomerase inhibitors, kinase inhibitors, microtubule inhibitors, angiogenesis inhibitors or other agents. Some patients respond to one therapy better than another, presenting the potential for a patient to follow multiple therapeutic routes to effective therapy. Valuable time early in a patient's treatment program can be lost pursuing a therapy which eventually is proven ineffective for that patient. Many patients cannot afford the time for trial-and-error choices of therapeutic regimens. Expedient and accurate treatment decisions lead to effective management of the disease.

SUMMARY

The present disclosure relates to prognosis and planning for treatment of tumors by measurement of the amount, presence or changes of markers provided herein. The markers are predictive of whether there will be a favorable outcome (e.g., good response, long time-to-progression, and/or long term survival) after treatment with a NEDD8-activating enzyme (NAE) inhibitor, such as a 1-substituted methyl sulfamate. Testing samples comprising tumor cells, e.g., in vitro, to determine the presence, amounts or changes of genetic markers, e.g., the mutational status of at least one marker gene, identifies particular patients who are expected to have a favorable outcome with treatment, e.g., with an NAE inhibitor, such as a 1-substituted methyl sulfamate, and whose disease may be managed by standard or less aggressive treatment, as well as those patients who are expected have an unfavorable outcome with the treatment and may require an alternative treatment to, a combination of treatments and/or more aggressive treatment with an NAE inhibitor to ensure a favorable outcome and/or successful management of the disease.

In one aspect, the invention provides kits useful in determination of characteristics, e.g., amounts, presence or changes, of the markers. In another aspect, the invention provides methods for determining prognosis and treatment or disease management strategies. In these aspects, the characteristic, e.g., size, sequence, composition or amount of marker in a sample comprising tumor cells is measured. In one embodiment, the tumor is a liquid, e.g., hematological tumor, e.g., acute myelogenous leukemia, myelodysplastic syndrome or multiple myeloma. In another embodiment, the tumor is a solid tumor, e.g., melanoma, non-small cell lung cancer, esophageal cancer, bladder cancer, neuroblastoma cancer, mesothelioma, pancreatic cancer.

In various embodiments, the characteristic, e.g., size, sequence, composition or amount of DNA, the size, sequence, composition or amount of RNA and/or the size, sequence, composition or amount of protein corresponding to a marker gene with one or more mutation, e.g., somatic mutation, described herein is measured. Useful information leading to the prognosis or treatment or disease management strategies is obtained when assays reveal information about a marker gene, e.g., whether the gene is mutated, or not, the identity of the mutation, and/or whether the RNA or protein amount of a mutated gene or genes indicates overexpression or underexpression. In one embodiment, the strategy is determined for E1 enzyme inhibition, e.g., NAE inhibition, e.g., MLN4924, therapy.

A marker gene useful to test for determination of prognosis or treatment or disease management strategy is selected from the group consisting of neurofibromin 2 (NF2), mothers against decapentaplegic homolog 4 (SMAD4), lysine-specific demethylase 6A (KDM6A), tumor protein p53 (TP53), cyclin-dependent kinase inhibitor 2A (CDKN2A), cyclin-dependent kinase inhibitor 2A p14 variant (CDKN2A_p14), in some cases, F-box and WD repeat domain containing 7 (FBXW7) and, in some cases adenomatous polyposis coli (APC). Each marker gene includes mutations or alterations whose presence in DNA or whose effects, e.g., on marker RNA and/or protein characteristics, e.g., amounts, size, sequence or composition, can provide information for determination of prognosis or treatment or disease management. In some embodiments, a gene or a mutant or modified form thereof useful as a marker, has a DNA, an RNA and/or protein characteristic, e.g., size, sequence, composition or amount, e.g., in a sample comprising tumor cells, which is different than a normal DNA, RNA and/or protein. Described herein are examples of modifications of these genes, referred to as "marker genes" whose mutation or amounts can provide such information.

The mutation of the markers of the present invention, provide information about outcome after treatment, e.g., with an NAE inhibitor, such as a 1-substituted methyl sulfamate. By examining the characteristic, e.g., size, sequence, composition or amount of one or more of the identified markers in a tumor, it is possible to determine which therapeutic agent, combination of agents, dosing and/or administration regimen is expected to provide a favorable outcome upon treatment. By examining the characteristic, e.g., size, sequence, composition or amount of one or more of the identified markers or marker sets in a cancer, it is also possible to determine which therapeutic agent, combination of agents, dosing and/or administration regimen is less likely to provide a favorable outcome upon treatment. By examining the characteristic, e.g., size, sequence, composition or amount of one or more of the identified markers, it is therefore possible to eliminate ineffective or inappropriate therapeutic agents or regimens. Importantly, these determinations can be made on a patient-by-patient basis. Thus, one can determine whether or not a particular therapeutic regimen is likely to benefit a particular patient or type of patient, and/or whether a particular regimen should be started or avoided, continued, discontinued or altered.

The present invention is directed to methods of identifying and/or selecting a cancer patient who is expected to demonstrate a favorable outcome upon administration of a therapeutic regimen, e.g., a therapeutic regimen comprising an NAE inhibitor, such as a 1-substituted methyl sulfamate treatment. Additionally provided are methods of identifying a patient who is expected to have an unfavorable outcome upon administration of such a therapeutic regimen. These methods typically include measuring, determining, receiving, storing or transmitting information about the characteristic, e.g., size, sequence, composition or amount of one or more markers or mutation of marker gene(s) in a patient's tumor (e.g., a patient's cancer cells, e.g., hematological cancer cells or solid tumor cells), optionally comparing that to the characteristic, e.g., size, sequence, composition or amount of a reference marker, and in a further embodiment, identifying or advising whether result from the sample corresponds to a favorable outcome of a treatment regimen, e.g., an NAE inhibitor, such as a 1-substituted methyl sulfamate treatment regimen.

Additionally provided methods include therapeutic methods which further include the step of beginning, continuing, or commencing a therapy accordingly where the presence of a mutation in a marker gene or the characteristic, e.g., size, sequence, composition or amount of a patient's marker or markers indicates that the patient is expected to demonstrate a favorable outcome with the therapy, e.g., the NAE inhibitor, such as a 1-substituted methyl sulfamate therapeutic regimen. In addition, the methods include therapeutic methods which further include the step of stopping, discontinuing, altering or halting a therapy accordingly where the presence of a mutation in a marker gene or the characteristic, e.g., size, sequence, composition or amount of a patient's marker indicates that the patient is expected to demonstrate an unfavorable outcome with the treatment, e.g., with the NAE inhibitor, such as a 1-substituted methyl sulfamate regimen, e.g., as compared to a patient identified as having a favorable outcome receiving the same therapeutic regimen. In another aspect, methods are provided for analysis of a patient not yet being treated with a therapy, e.g., an NAE inhibitor, such as a 1-substituted methyl sulfamate therapy and identification and prediction of treatment outcome based upon the presence of a mutation in a marker gene or characteristic, e.g., size, sequence, composition or amount of one or more of a patient's marker described herein. Such methods can include not being treated with the therapy, e.g., NAE inhibitor, such as a 1-substituted methyl sulfamate therapy, being treated with therapy, e.g., NAE inhibitor, or being treated with a 1-substituted methyl sulfamate therapy in combination with one more additional therapies, being treated with an alternative therapy to an NAE inhibitor, such as a 1-substituted methyl sulfamate therapy, or being treated with a more aggressive dosing and/or administration regimen of a therapy, e.g., E1 enzyme inhibitor, such as an NAE inhibitor, e.g., as compared to the dosing and/or administration regimen of a patient identified as having a favorable outcome to standard NAE inhibitor, such as a 1-substituted methyl sulfamate therapy. Thus, the provided methods of the invention can eliminate ineffective or inappropriate use of therapy, e.g., NAE inhibitor, such as 1-substituted methyl sulfamate therapy regimens.

Additional methods include methods to determine the activity of an agent, the efficacy of an agent, or identify new therapeutic agents or combinations. Such methods include methods to identify an agent as useful, e.g., as an NAE inhibitor, such as a 1-substituted methyl sulfamate, for treating a cancer, e.g., a hematological cancer (e.g., multiple myeloma, leukemias, lymphoma, etc) or solid tumor cancer (e.g., melanoma, esophageal cancer or bladder cancer), based on its ability to affect the presence of a mutation in a marker gene or characteristic, e.g., size, sequence, composition or amount of a marker or markers of the invention. For example, an inhibitor which decreases or increases the presence of a mutation in a marker gene or characteristic, e.g., size, sequence, composition or amount of a marker or markers provided in a manner that indicates favorable outcome of a patient having cancer would be a candidate agent for the cancer. Alternatively, an agent which is able to decrease the viability of a tumor cell comprising a marker indicative of an unfavorable outcome would be a candidate agent for the cancer.

The present invention is also directed to methods of treating a cancer patient, with a therapeutic regimen, e.g., an NAE inhibitor, such as a 1-substituted methyl sulfamate therapy regimen (e.g., alone, or in combination with an additional agent such as a chemotherapeutic agent, e.g., a glucocorticoid agent, a proteasome inhibitor, an alkylating agent, a kinase inhibitor or a topoisomerase inhibitor), which includes the step of selecting for treatment a patient whose marker characteristic, e.g., size, sequence, composition or amount indicates that the patient is expected to have a favorable outcome with the therapeutic regimen, and treating the patient with the therapy, e.g., NAE inhibition, such as a 1-substituted methyl sulfamate therapy. In some embodiments, the method can include the step of selecting a patient whose marker characteristic, e.g., size, sequence, composition or amount or amounts indicates that the patient is expected have a favorable outcome and administering a therapy other than an NAE inhibitor therapy that demonstrates similar expected survival times as the NAE inhibitor, such as a 1-substituted methyl sulfamate therapy.

Additional methods of treating a cancer patient include selecting patients that are unlikely to experience a favorable outcome upon treatment with a cancer therapy (e.g., NAE inhibitor, such as a 1-substituted methyl sulfamate therapy). Such methods can further include one or more of: administering a higher dose or increased dosing schedule of a therapy, e.g., NAE inhibitor, such as a 1-substituted methyl sulfamate as compared to the dose or dosing schedule of a patient identified as having a favorable outcome with standard therapy; administering a cancer therapy other than an NAE inhibitor, such as a 1-substituted methyl sulfamate therapy; administering an NAE inhibitor, such as a 1-substituted methyl sulfamate agent in combination with an additional agent. Further provided are methods for selection of a patient having aggressive disease which is expected to demonstrate more rapid time to progression and death.

Additional methods include a method to evaluate whether to treat or pay for the treatment of cancer, e.g., hematological cancer (e.g., multiple myeloma, leukemias, lymphoma, etc.) or solid tumor cancer (e.g., melanoma, esophageal cancer or bladder cancer) by reviewing the amount of a patient's marker or markers for indication of outcome to a cancer therapy, e.g., an NAE inhibitor, such as a 1-substituted methyl sulfamate therapy regimen, and making a decision or advising on whether payment should be made.

The entire contents of all publications, patent applications, patents and other references mentioned herein are incorporated by reference.

Other features and advantages of the invention will be apparent from the following detailed description, drawings and from the claims.

DRAWINGS

FIG. 1. General structure of 1-substituted methyl sulfamate. $G^1$ is —O— or —$CH_2$—; $G^2$ is —H or —OH; $G^3$ is —H or —OH; $G^4$ is —NH—, —O— or a covalent bond; and $G^5$ is substituted heteroaryl.

Figure 2:
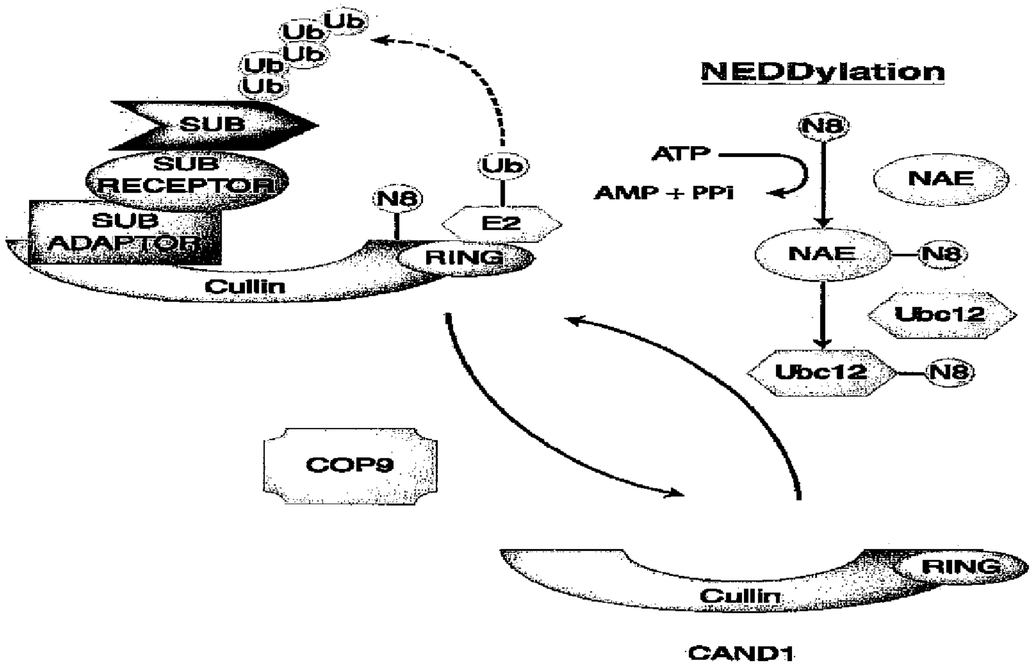

FIG. 2. General pathways for cullin-ring ligase (CRL) ubiquitination of protein substrates and for neddylation. In CRLs, the cullin subunit must be modified on a conserved lysine by the ubiquitin-like protein NEDD8 to activate holoenzyme activity. NEDD8 activation and conjugation to cullin proteins is catalyzed via an enzymatic cascade that is homologous to ubiquitination involving NEDD8's E1 (NAE) and E2 (Ubc12). Removal of NEDD8 from cullin is catalyzed by the COPS signalosome. Deneddylation facilitates dissociation of CRL components. The cullin-RING core is sequestered in an inactive state by binding to CAND1 until it is recruited to form a new CRL.

Figure 3:
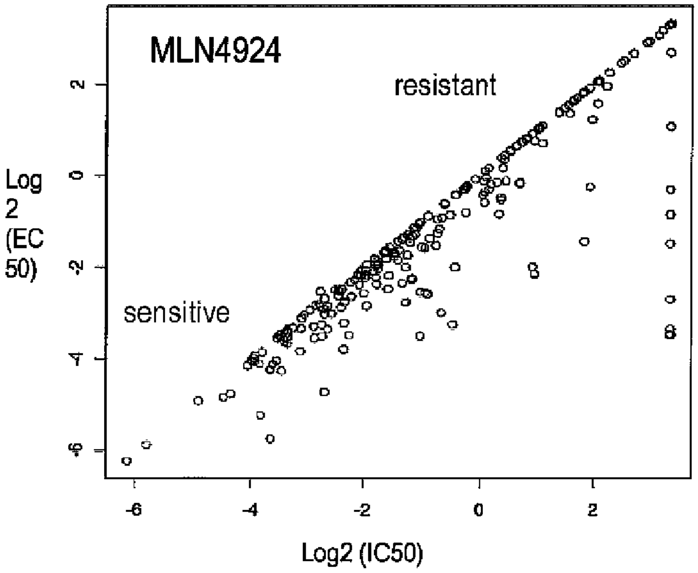

FIG. 3. Response of a cell line panel 2 to MLN4924. Each point represents one cell line.

FIGS. 4A-B. Comparison of responses of cell line panels to MLN4924. A. Ordering of cell line panel 2 by EC50. Darkened lines represent cell lines that are present in panel 1. There are 114 cell lines with identical names in both panels. B. Comparison of Percent of Control (POC) viability for the cell lines which are present in both panels. The results of the overlapping cell lines have a Spearman Rank Order Correlation of 0.72, p-value<2.2e-16.

Figure 5:
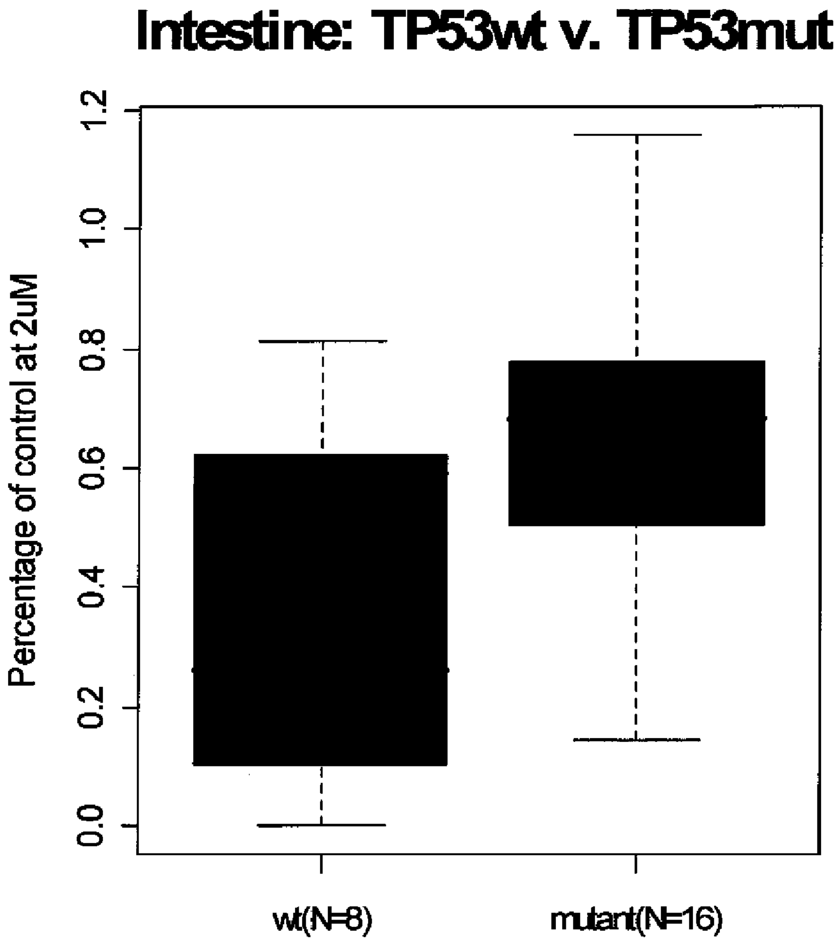
Figure 6A:
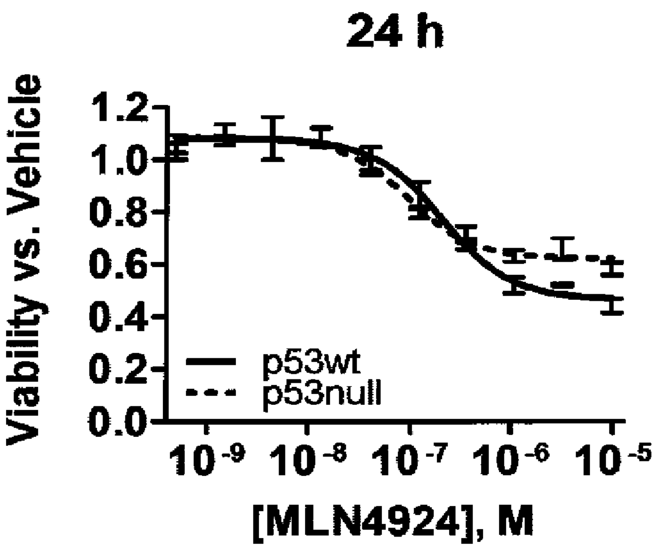
Figure 6B:
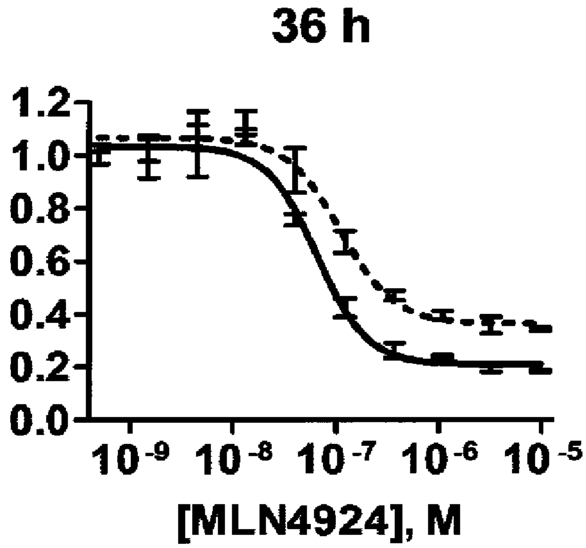
Figure 6C:
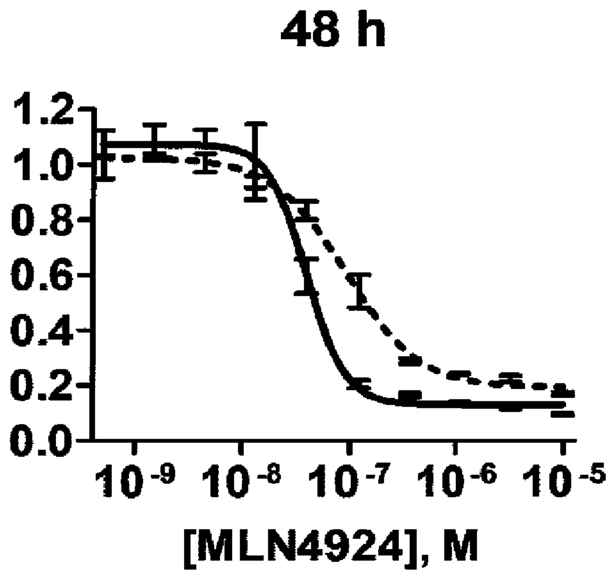
Figure 6D:
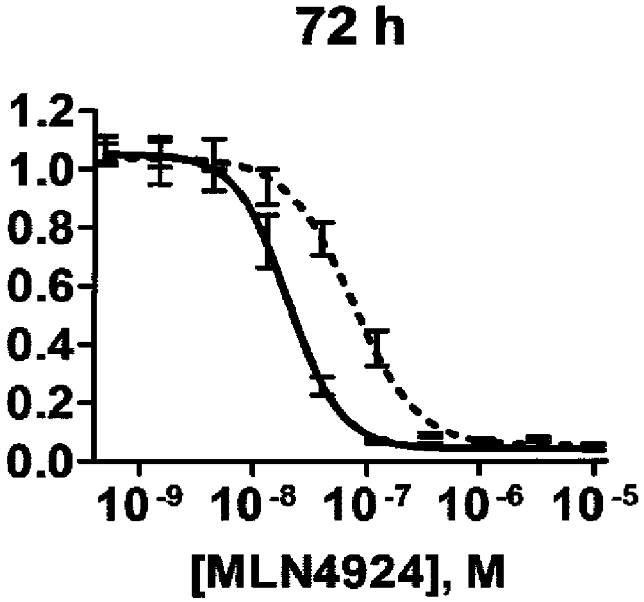

FIG. 5. Tissue association of resistance with TP53 mutations. TP53 mutant colon cancer cell lines are more resistant (higher percent of control viability) to MLN4924 treatment than TP53 wt cell lines.

FIGS. 6A-D. Effect of TP53 Loss on Viability of Cancer Cell Lines Following Treatment with Different Doses of MLN4924 at Multiple Time Points. The effect of TP53 knock-out on the sensitivity of paired HCT-116 colon cancer cell lines to MLN4924 was measured by ATPlite, across a range of MLN4924 concentrations and time points. Data are represented as mean±SEM, N=3. Dotted line, p53 knock-out; solid line, p53 wild type.

DETAILED DESCRIPTION

One of the continued problems with therapy in cancer patients is individual differences in response to therapies. While advances in development of successful cancer therapies progress, only a subset of patients respond to any particular therapy. With the narrow therapeutic index and the toxic potential of many available cancer therapies, such differential responses potentially contribute to patients undergoing unnecessary, ineffective and even potentially harmful therapy regimens. If a designed therapy could be optimized to treat individual patients, such situations could be reduced or even eliminated. Furthermore, targeted designed therapy may provide more focused, successful patient therapy overall. Accordingly, there is a need to identify particular cancer patients who are expected to have a favorable outcome when administered particular cancer therapies as well as particular cancer patients who may have a favorable outcome using more aggressive and/or alternative cancer therapies, e.g., alternative to previous cancer therapies administered to the patient. It would therefore be beneficial to provide for the diagnosis, staging, prognosis, and monitoring of cancer patients, including, e.g., hematological cancer patients (e.g., multiple myeloma, leukemias, lymphoma, etc.) or solid tumor cancer (e.g., melanoma, esophageal cancer or bladder cancer) who would benefit from particular cancer inhibition therapies as well as those who would benefit from a more aggressive and/or alternative cancer inhibition therapy, e.g., alternative to a cancer therapy or therapies the patient has received, thus resulting in appropriate preventative measures.

The present invention is based, in part, on the recognition that mutation of a marker gene can be associated with sensitivity of a cell comprising the mutated gene to an NAE inhibitor, such as a 1-substituted methyl sulfamate. In some embodiments, the marker gene is involved in the cullin ring ligase (CRL) pathway, e.g., a gene whose encoded protein interacts with a CRL or a CRL-associated protein, or is a CRL substrate. A protein encoded by a marker gene can have a wild type function as a tumor suppressor. Examples of marker genes include NF2, SMAD4 and/or KDM6A. Other examples of marker genes include TP53, APC, CDKN2A and/or CDKN2A_p14. Marker genes can exhibit mutations, e.g., somatic mutations, whose presence can affect expression or activity of the encoded gene product. In some embodiments, there can be more than one mutation in a marker gene or more than one marker gene with a mutation in a tumor cell or tumor. In additional embodiments, there can be marker gene mutations in cells which have mutations in additional genes, including mutations that can lead to tumorigenesis, but the additional mutated genes may not be marker genes as considered herein. In some embodiments, the mutation is an inactivating mutation. In other embodiments, the mutation affects the expression of the marker gene. In other embodiments, a mutation can result in an altered interaction of the encoded gene product with a cellular binding partner. The identification and/or measurement of the mutation in the marker gene can be used to determine whether a favorable outcome can be expected by treatment of a tumor, e.g., with an NAE inhibitor, such as a 1-substituted methyl sulfamate therapy or whether an alternative therapy to and/or a more aggressive therapy with, e.g., an NAE inhibitor, such as a 1-substituted methyl sulfamate inhibitor may enhance expected survival time. For example, the compositions and methods provided herein can be used to determine whether a patient is expected to have a favorable outcome to an NAE inhibitor, such as a 1-substituted methyl sulfamate therapeutic agent or an NAE inhibitor, such as a 1-substituted methyl sulfamate dosing or administration regimen. In general, mutation in the tumor suppressor marker genes described herein is associated with sensitivity to or favorable outcome of treatment with a NAE inhibitor. Examples of marker genes which can function as a tumor suppressor in pathways related to cullin ring ligase and whose mutation is associated with sensitivity to NAE inhibition include NF2, SMAD4, KDM6A, FBXW7, CDKN2A and/or CDKN2A_p14. However, TP53 and APC also are tumor suppressor marker genes. In particular, TP53 pathway genes are associated with NAE inhibitor effects. As described herein, in some embodiments for many tumor types, mutation in TP53, and in some cases, APC, leads to resistance to NAE inhibition. Accordingly, a wild type marker gene from the group consisting TP53 and APC can be associated with NAE sensitivity. In some embodiments, mutation of a marker gene selected from the group consisting of TP53 and APC is associated with resistance to an NAE inhibitor.

Based on these identifications, the present invention provides, without limitation: 1) methods and compositions for determining whether an NAE inhibitor, such as a 1-substituted methyl sulfamate therapy regimen will or will not be effective to achieve a favorable outcome and/or manage the cancer; 2) methods and compositions for monitoring the effectiveness of an NAE inhibitor, such as a 1-substituted methyl sulfamate therapy (alone or in a combination of agents) and dosing and administrations used for the treatment of tumors; 3) methods and compositions for treatments of tumors comprising, e.g., NAE inhibitor, such as a 1-substituted methyl sulfamate inhibition therapy regimen; 4) methods and compositions for identifying specific therapeutic agents and combinations of therapeutic agents as well as dosing and administration regimens that are effective for the treatment of tumors in specific patients; and 5) methods and compositions for identifying disease management strategies.

Ubiquitin and other ubiquitin-like molecules (ubls) are activated by a specific enzyme (an E1 enzyme) which catalyzes the formation of an acyl-adenylate intermediate with the C-terminal glycine of the ubl. The activated ubl is then transferred to a catalytic cysteine residue within the E1 enzyme through formation of a thioester bond intermediate. The E1-ubl intermediate and an E2 associate, resulting in a thioester exchange wherein the ubl is transferred to the active site cysteine of the E2. The ubl is then conjugated to the target protein, either directly or in conjunction with an E3 ligase, through isopeptide bond formation with the amino group of a lysine side chain in the target protein. The ubl named Neural precursor cell-Expressed Developmentally Downregulated 8 (NEDD8) is activated by the heterodimer NEDD8-activating enzyme (NAE, also known as APPBP1-UBA3, UBE1C (ubiquitin-activating enzyme E1C)) and is transferred to one of two E2 conjugating enzymes (ubiquitin carrier protein 12 (UBC12) and UBC17), ultimately resulting in ligation of NEDD8 to cullin proteins by the cullin-RING subtype of ubiquitin ligases (see FIG. 2). A function of neddylation is the activation of cullin-based ubiquitin ligases involved in the turnover of many cell cycle and cell signaling proteins, including p27 and I-κB. See Pan et al., *Oncogene* 23:1985-97 (2004). Inhibition of NAE can disrupt cullin-RING ligase-mediated protein turnover and can lead to apoptotic death in cells, e.g., tumor cells or cells of a pathogenic organism, e.g. a parasite. See Soucy et al. (2010) *Genes & Cancer* 1:708-716.

As used herein, the term "E1," "E1 enzyme," or "E1 activating enzyme" refers to any one of a family of related ATP-dependent activating enzymes involved in activating or promoting ubiquitin or ubiquitin-like (collectively "ubl") conjugation to target molecules. E1 activating enzymes function through an adenylation/thioester intermediate formation to transfer the appropriate ubl to the respective E2 conjugating enzyme through a transthiolation reaction. The resulting activated ubl-E2 promotes ultimate conjugation of the ubl to a target protein. A variety of cellular proteins that play a role in cell signaling, cell cycle, and protein turnover are substrates for ubl conjugation which is regulated through E1 activating enzymes (e.g., NAE, UAE, SAE). Unless otherwise indicated by context, the term "E1 enzyme" is meant to refer to any E1 activating enzyme protein, including, without limitation, NEDD8 activating enzyme (NAE (APPBP1/Uba3)), ubiquitin activating enzyme (UAE (Uba1)), sumo activating enzyme (SAE (Aos1/Uba2)), UBA4, UBA5, UBA6, ATG7 or ISG15 activating enzyme (UbelL).

The term "E1 enzyme inhibitor" or "inhibitor of E1 enzyme" is used to signify a compound having a structure as defined herein, which is capable of interacting with an E1 enzyme and inhibiting its enzymatic activity. Inhibiting E1 enzymatic activity means reducing the ability of an E1 enzyme to activate ubiquitin like (ubl) conjugation to a substrate peptide or protein (e.g., ubiquitination, neddylation, sumoylation). In some embodiments, an E1 enzyme inhibitor can inhibit more than one E1 enzyme. In other embodiments, an E1 enzyme inhibitor is specific for a particular E1 enzyme. In various embodiments, such reduction of E1 enzyme activity is at least about 50%, at least about 75%, at least about 90%, at least about 95%, or at least about 99%. In various embodiments, the concentration of E1 enzyme inhibitor required to reduce an E1 enzymatic activity is less than about 1 μM, less than about 500 nM, less than about 100 nM, less than about 50 nM, or less than about 10 nM.

As used herein, the term "NAE inhibitor" refers to an inhibitor of the NAE heterodimer. Examples of NAE inhibitors include 1-substituted methyl sulfamates (see FIG. 1), including MLN4924. Langston S. et al. U.S. patent application Ser. No. 11/700,614, whose PCT application was published as WO07/092213, WO06084281 and WO2008/019124 (the entire contents of each of the foregoing published patent applications are hereby incorporated by reference), disclose compounds which are effective inhibitors of E1 activating enzymes, e.g., NAE. As explained in the cited publications, the NAE inhibitor may comprise a compound or a pharmaceutically acceptable salt thereof. Pharmaceutically acceptable salts may be derived from inorganic or organic acids and bases. For reviews of suitable salts, see, e.g., Berge et al, J. Pharm. Sci. 66:1-19 (1977) and Remington: The Science and Practice of Pharmacy, 20th Ed., ed. A. Gennaro, Lippincott Williams & Wilkins, 2000. Non-limiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. In some embodiments, NAE inhibitors do not inhibit, or are very poor at inhibiting, other (non-NAE) E1 enzymes. The compounds are useful for inhibiting E1 activity in vitro and in vivo and are useful for the treatment of disorders of cell proliferation, e.g., cancer, and other disorders associated with E1 activity, such as pathogenic infections and neurodegenerative disorders. One class of compounds described in Langston et al. are 4-substituted ((1S, 2S, 4R)-2-hydroxy-4-{7H-pyrrolo[2,3-d]pyrimidin-7-yl}cyclopentyl)methyl sulfamates.

MLN4924 (((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate) is an NAE-specific E1 inhibitor which disrupts cullin-RING ligase-mediated protein turnover leading to apoptotic death in human tumor cells by perturbation of cellular protein homeostasis (Soucy et al. (2009) *Nature* 458:732-736). The evaluation of MLN4924 in cellular and tumor xenograft studies has revealed two distinct mechanisms of action. The first is the induction of DNA re-replication, DNA damage and cell death through MLN4924-mediated dysregulation of the $CRL1^{SKP2}$ and $CRL4^{DDB1}$ substrate Cdt-1 (Milhollen et al. (2011) *Cancer Res.* 71:3042-3051). It has been shown that p53 status does not impact the induction of DNA re-replication but may make cells more prone to undergo apoptosis or senescence depending on the appropriate genetic background (Milhollen et al. (2011) supra, Lin et al. (2010) *Nature* 464:374-379 and Lin et al. (2010) *Cancer Res.* 70:10310-20). The second mechanism is the inhibition of NF-κB pathway activity in NF-κB dependent Diffuse Large B-Cell Lymphomas primarily through dysregulation of $CRL1^{\beta TRCP}$ mediated turnover of phosphorylated IηBα (Milhollen et al. (2010) *Blood* 116:1515-1523). In addition, pre-clinical models of Acute Myelogenous Leukemia (AML) are sensitive to MLN4924 inhibition in both cell lines and primary patient blasts through mechanisms related to Cdt-1 dysregulation, NF-κB inhibition and induction of reactive oxygen species (Swords et al. (2010) *Blood* 115: 3796-3800).

Genes such as NF2 (reviewed by Ahronowitz et al. (2007) *Human Mutation* 28:1-2), KDM6A (reviewed by van Haaften et al. (2009) *Nat. Genet.* 41:521-523), FBXW7, TP53, CDKN2A and CDKN2A_p14 are mutated in many cancer types. SMAD4 is mutated in a number of cancers, but many of SMAD4 mutations are found in cancers of the intestine, pancreas (reviewed by Miyaki and Kuroki (2003) *Biochem. Biophys. Res. Commun.* 306:799-804) or thyroid gland.

As used herein, "NF2" refers to the longer isoform of the gene associated with GenBank Accession No. NM_000268, SEQ ID NO:1 (open reading frame is SEQ ID NO:2, nucleotides 444 to 2231 of SEQ ID NO:1), encoding GenPept Accession No. NP_000259, SEQ ID NO:3). Other names for NF2 include ACN, BANF, SCH and merlin (moesin-ezrin-radixin-like protein). NF2 functions as a tumor suppressor gene and can be found on chromosome 22. NF2 interacts with the cytoskeleton, cell surface proteins and may be involved in cytoskeletal dynamics and regulating ion transport. Functions of NF2 that can relate it to sensitivity to NAE inhibition, e.g., MLN4924 include its ability to inhibit the E3 ubiquitin ligase $CRL4^{DCAF1}$ (Li et al. (2010) *Cell* 140:477-490). Mutations in NF2 can disrupt its inhibitory activity and lead to uncontrolled ubiquitination of substrates of $CRL4^{DCAF1}$ and proliferation of cells harboring the mutated gene.

As used herein, "SMAD4" refers to the gene associated with GenBank Accession No. NM_005359, SEQ ID NO:4 (open reading frame is SEQ ID NO:5, nucleotides 539 to 2197 of SEQ ID NO:4), encoding GenPept Accession No. NP_005350, SEQ ID NO:6. Other names for SMAD4 include deleted in pancreatic carcinoma locus 4 (DPC4), JIP, or mothers against decapentaplegic, *Drosophila*, homolog of, 4 (MAD4). SMAD4 is a signal transduction protein involved in transforming growth factor (TGF)-beta signaling. SMAD4 can act as a tumor suppressor and can be targeted for degradation by ubiquitination by the Skp-Cullin-F-box protein (SCF) complex.

As used herein, "KDM6A" refers to the gene associated with GenBank Accession No. NM_021140, SEQ ID NO:7 (open reading frame is SEQ ID NO:8, nucleotides 376 to 4581 of SEQ ID NO:7, or SEQ ID NO:9), encoding GenPept Accession No. NP_066963, SEQ ID NO:10 or SEQ ID NO:11 (SEQ ID NO:10 with a V instead of an L at position 173 and an R instead of L at 584, an N instead of S at position 601 and/or K instead of E at position 629). Other names for KDM6A include ubiquitously-transcribed tetratricopeptide repeat protein X-linked or ubiquitously-transcribed TPR gene on the X chromosome (UTX), or bA286N14.2. KDM6A is a histone demethylase and can function as a tumor suppressor.

As used herein, "FBXW7" refers to the gene associated with GenBank Accession No. NM_033632, SEQ ID NO:12 (open reading frame is SEQ ID NO:13, nucleotides 150 to 2273 of SEQ ID NO:12), encoding GenPept Accession No. NP_361014, SEQ ID NO:14. Other names for FBXW7 include homolog of *C elegans* sel-10 (SEL10), archipelago homolog (AGO), F-box protein FBX30 (FBX030), or cell division control protein 4 (CDC4). FBXW7 can associate into a ubiquitin protein ligase complex to participate in phosphorylation-dependent ubiquitination of proteins, including proteins involved in cell cycle and survival. FBXW7 can act as a tumor suppressor. Use of FBXW7 as marker gene may be organ-specific, i.e., it can be a marker of sensitivity in tumors arising in some tissues but not others. For example, FBXW7 can be a marker of sensitivity in tumors of the uterus, cervix or liver, but not a marker of sensitivity in tumors of the digestive tract, where mutations in other genes may dominate to result in the insensitivity or resistance of cells from those tumors to MLN4924.

As used herein, "TP53" refers to the gene associated with GenBank Accession No. NM_000546, SEQ ID NO:15 (open reading frame is SEQ ID NO:16, nucleotides 203 to 1384 of SEQ ID NO:15, or a variant wherein the nucleotide at position 417 is a guanine instead of a cytosine), encoding GenPept Accession No. NP_000537, SEQ ID NO:17 or a variant wherein the amino acid residue at position 72 is an arginine, R instead of a proline, P). Other names for TP53 include BCC7, LFS1 and p53. TP53 binds DNA and activates transcription factors and can function as a tumor suppressor.

As used herein, "CDKN2A" refers to the gene associated with GenBank Accession No. NM_000077, SEQ ID NO:18 (open reading frame is SEQ ID NO:19, nucleotides 307 to 777 of SEQ ID NO:18), encoding GenPept Accession No. NP_000068, SEQ ID NO:20. Other names for CDKN2A include alternate open reading frame (ARF), p16, p16ARF, inhibitor of cyclin-dependent kinase 4 (INK4) and multiple tumor suppressor gene-1 (MTS1). Variants of CDKN2A differ in the first exon. One variant is "CDKN2A_p14" or "CDKN2A.p14," also known as p14ARF, is associated with GenBank accession number NM_058195, SEQ ID NO:21 (open reading frame is SEQ ID NO:22, nucleotides 38 to 559 of SEQ ID NO:21); GenPept NP_478102, SEQ ID NO:23 or a variant which begins at amino acid residue 42 of SEQ ID NO:23. CDKN2A_p14 results from translation in a different reading frame than p16ARF (p16INK4a, CDKN2A). CDKN2A and CDKN2A_p14 inhibit cyclin dependent kinase 4, can stabilize p53 and can regulate cell cycle G1 progression. CDKN2A and CDKN2A_p14 can act as a tumor suppressor.

As used herein, "APC" refers to adenomatous polyposis coli, the gene associated with GenBank Accession No. NM_000038, SEQ ID NO:24 (open reading frame SEQ ID NO:25, or a variant with a thymine instead of a cytosine at nucleotide 1458), encoding GenPept Accession No. NP_000029, SEQ ID NO:26. Other names for APC include BTSP2, and DP2. APC binds microtubules and inhibits the Wnt-signalling pathway and can function as a tumor suppressor.

There has been interest in public cataloging mutations associated with cancers. Examples of public databases which include information about mutations associated with cancers are the Database of Genotypes and Phenotypes (dbGaP) maintained by the National Center for Biotechnology Information (Bethesda, Md.) and Catalogue of Somatic Mutations in Cancer (COSMIC) database maintained by the Wellcome Trust Sanger Institute (Cambridge, UK).

Compositions and methods are provided to determine the mutational status, e.g., to identify mutations in marker genes in hematological (e.g., multiple myeloma, leukemias, lymphoma, etc.) or solid (e.g., melanoma, esophageal cancer, lung cancer or bladder cancer) tumors to predict response to treatment, time-to-progression and survival upon treatment. Compositions and methods provided herein also can identify mutations in marker genes in solid tumors such as from colon cancer, breast cancer, head and neck cancer, or central nervous system cancer.

Markers were identified based on genetic profiles of tumor cells which exhibit sensitivity to treatment to MLN4924. TP53 marker also was identified based on the behavior of isogenic cell lines which differ in the deletion of the TP53 gene. Observed sensitivity can be consistent among tumor cells tested by more than one method.

Unless otherwise defined, all technical and scientific terms used herein have the meanings which are commonly understood by one of ordinary skill in the art to which this invention belongs. Generally, nomenclature utilized in connection with, and techniques of cell and tissue culture, molecular biology and protein and oligo- or polynucleotide chemistry and hybridization described herein are those known in the art. GenBank or GenPept accession numbers and useful nucleic acid and peptide sequences can be found at the website maintained by the National Center for Biotechnology Information, Bethesda, Md. The content of all database accession records (e.g., from Affymetrix HG133 annotation files, Entrez, GenBank, RefSeq, COSMIC) cited throughout this application (including the Tables) are hereby incorporated by reference. Standard techniques are used for recombinant DNA, oligonucleotide synthesis, protein purification, tissue culture and transformation and transfection (e.g., electroporation, lipofection, etc). Enzymatic reactions are performed according to manufacturer's specifications or as commonly accomplished in the art or as described herein. The foregoing techniques and procedures generally are performed according to methods known in the art, e.g., as described in various general and more specific references that are cited and discussed throughout the present specification. See e.g., Sambrook et al. (2000) *Molecular Cloning: A Laboratory Manual* ($3^{rd}$ ed., Cold Spring Harbor Laboratory Press, Cold Spring Harbor, N.Y.) or Harlow, E. and Lane, D. (1988) *Antibodies: A Laboratory Manual* (Cold Spring Harbor Laboratory Press, Cold Spring Harbor, N.Y.). The nomenclatures utilized in connection with, and the laboratory procedures and techniques of, analytical chemistry, synthetic organic chemistry, and medicinal and pharmaceutical chemistry described herein are known in the art. Standard techniques are used for chemical syntheses, chemical analyses, pharmaceutical preparation, formulation and delivery, and treatment of patients. Furthermore, unless otherwise required by context, singular terms shall include pluralities and plural terms shall include the singular. In the case of conflict, the present specification, including definitions, will control.

The articles "a," "an" and "at least one" are used herein to refer to one or to more than one of the grammatical object of the article. By way of example, "an element" means one or more than one element, at least one element. In the case of conflict, the present specification, including definitions, will control.

As used herein, a "favorable" outcome or prognosis refers to long term survival, long time-to-progression (TTP), and/or good response. Conversely, an "unfavorable" prognosis refers to short term survival, short time-to-progression (TTP) and/or poor response.

A "marker" as used herein, includes a material associated with a marker gene which has been identified as having a mutation in tumor cells of a patient and furthermore that mutation is characteristic of a patient whose outcome is favorable or unfavorable with treatment e.g., by an NAE inhibitor, such as a 1-substituted methyl sulfamate. Examples of a marker include a material, e.g., a chromosome locus, DNA for a gene, RNA for a gene or protein for a gene. For example, a marker includes a marker gene material, e.g., a chromosome locus, DNA, RNA or protein which demonstrates a characteristic, e.g., size, sequence, composition or amount indicative of a short term survival patient; alternatively a marker includes a marker gene material, e.g., a chromosome locus, DNA, RNA or protein which demonstrates a mutation or characteristic, e.g., size, sequence, composition or amount indicative of a long term survival patient. In another example, a marker includes a marker gene material, e.g., a chromosome locus, DNA, RNA or protein whose mutation or characteristic, e.g., size, sequence, composition or amount is indicative of a patient with a poor response to treatment; alternatively a marker includes a marker gene material, e.g., a chromosome locus, DNA, RNA or protein whose mutation or characteristic, e.g., size, sequence, composition or amount is indicative of a patient with a good response. In a further example, a marker includes a marker gene material, e.g., a chromosome locus, DNA, RNA or protein whose mutation or characteristic, e.g., size, sequence, composition or amount is indicative of a patient whose disease has a short time-to-progression (TTP) upon treatment; alternatively a marker includes a marker gene material, e.g., a chromosome locus, DNA, RNA or protein whose mutation or characteristic, e.g., size, sequence, composition or amount is indicative of a patient whose disease has a long TTP. In a yet a further example, a marker includes a marker gene material, e.g., a chromosome locus, DNA, RNA or protein whose mutation or characteristic, e.g., size, sequence, composition or amount is indicative of a patient whose disease has a short term survival upon treatment; alternatively a marker includes a marker gene material, e.g., a chromosome locus, DNA, RNA or protein whose mutation or characteristic, e.g., size, sequence, composition or amount is indicative of a patient whose disease has a long term survival. Thus, as used herein, marker is intended to include each and every one of these possibilities, and further can include each single marker individually as a marker; or alternatively can include one or more, or all of the characteristics collectively when reference is made to "markers" or "marker sets."

A chromosome locus marker useful to measure for determination of prognosis or treatment or disease management strategy is selected from the group consisting of chromosome 22q12.2 (NF2), e.g., from base pair 29999545 to 30094589, chromosome 18q21.1-21.2 (SMAD4), e.g., from base pair 48556583 to 48611412, chromosome Xp11.2 (KDM6A), e.g., from base pair 44732423 to 44971847, chromosome 4q31.3 (FBXW7), e.g., from base pair 153242410-153456172, chromosome 17p13.1 (TP53), e.g., from base pair 7571720 to 7590868, and 9p21 (CDKN2A and CDKN2A_p14), e.g., from base pair 21967751 to 21994490. Chromosome locus numbers are based on the reference human genome Build 37.3 (current as of Oct. 5, 2011) in the NCBI Gene database. A marker DNA, marker RNA or marker protein can correspond to base pairs on a chromosome locus marker. For example, a marker DNA can include genomic DNA from a chromosome locus marker, marker RNA can include a polynucleotide transcribed from a locus marker, and a marker protein can include a polypeptide resulting from expression at a chromosome locus marker in a sample, e.g., comprising tumor cells.

A "marker nucleic acid" is a nucleic acid (e.g., genomic DNA, mRNA, cDNA) encoded by or corresponding to a marker gene of the invention. Such marker nucleic acids include DNA, e.g., sense and anti-sense strands of genomic DNA (e.g., including any introns occurring therein), comprising the entire or a partial sequence, e.g., one or more of the exons of the genomic DNA, up to and including the open reading frame of any of the marker genes or the complement of such a sequence. The marker nucleic acids also include RNA comprising the entire or a partial sequence of any marker or the complement of such a sequence, wherein all thymidine residues are replaced with uridine residues, RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, a "marker nucleic acid" may also include a cDNA made by reverse transcription of an RNA generated by transcription of genomic DNA (including spliced RNA). A marker nucleic acid also includes sequences which differ, due to degeneracy of the genetic code, from the nucleotide sequence of nucleic acids encoding a protein which corresponds to a marker, e.g., a mutated marker, of the invention, and thus encode the same protein, e.g., mutated protein. As used herein, the phrase "allelic variant" refers to a nucleotide sequence which occurs at a given locus or to a polypeptide encoded by the nucleotide sequence. Such naturally occuring allelic variations can typically result in 1-5% variance in the nucleotide sequence of a given gene. Alternative alleles can be identified by sequencing the gene of interest in a number of different individuals, e.g., in cells, e.g., germline cells, of individuals without cancer. This can be readily carried out by using hybridization probes to identify the same genetic locus in a variety of individuals. Detection of any and all such nucleotide variations and resulting amino acid polymorphisms or variations that are the result of naturally occurring allelic variation and that do not alter the functional activity of a wild type marker gene is intended to be within the scope of the wild type version of a marker described herein. A "marker protein" is a protein encoded by or corresponding to a marker, e.g., a mutant nucleic acid, of the invention. The terms "protein" and "polypeptide' are used interchangeably. A protein of a marker specifically can be referred to by its name or amino acid sequence, but it is understood by those skilled in the art, that mutations, deletions and/or post-translational modifications can affect protein structure, appearance, cellular location and/or behavior. Unless indicated otherwise, such differences are not distinguished herein, and a marker described herein is intended to include any or all such varieties.

As used herein, a "marker gene" refers to a gene which can have a mutation such that its DNA, RNA and/or protein has a characteristic, e.g., size, sequence, composition or amount(s) which provide information about prognosis (i.e., are "informative") upon treatment. Marker genes described herein as linked to outcome after NAE inhibitor, such as 1-substituted methyl sulfamate (e.g., MLN4924) treatment are examples of genes within the chromosome locus markers described above and are provided in Table 1. Sequences of mRNA, open reading frames and proteins corresponding to marker genes also are listed in Table 1. A marker gene listed in Table 1 can have isoforms which are either ubiquitous or have restricted expression. Except for the separate listing of the CDKN2A_p14 isoform, the DNA SEQ ID NOs in Table 1 refer to the mRNA encoding the major or longest isoform and the protein SEQ ID NOs represent at least a precursor of such isoform and not necessarily the mature protein. These sequences are not intended to limit the marker gene identity to that isoform or precursor. The additional isoforms and mature proteins are readily retrievable and understandable to one of skill in the art by reviewing the information provided under the Entrez Gene (database maintained by the National Center for Biotechnology Information, Bethesda, Md.) identified by the ID number listed in Table 1.

TABLE 1

Marker Gene Description for NAE Inhibitor Treatment

| Marker Gene ID | Marker Gene Name | Entrez Gene ID | Chromosome location | Start base pair | End base pair | SEQ ID NOs: |
|---|---|---|---|---|---|---|
| NF2 | neurofibromin 2 | 4771 | 22q | 29999545 | 30094589 | 1, 2, 3 |
| SMAD4 | mothers against decapentaplegic homolog 4 | 4089 | 18q | 48556583 | 48611412 | 4, 5, 6 |
| KDM6A | lysine-specific demethylase 6A | 7403 | Xp | 44732423 | 44971847 | 7, 8, 9, 10, 11 |
| FBXW7 | F-box and WD repeat domain containing 7 | 55294 | 4q | 153242410 | 153456172 | 12, 13, 14 |
| TP53 | tumor protein p53 | 7157 | 17p | 7571720 | 7590868 | 15, 16, 17 |
| CDKN2A | cyclin-dependent kinase inhibitor 2A | 1029 | 9p | 21967751 | 21994490 | 18, 19, 20 |
| CDKN2A_p14 | cyclin-dependent kinase inhibitor 2A p14 variant | 1029 | 9p | 21967751 | 21994490 | 21, 22, 23 |
| APC | adenomatous polyposis coli | 324 | 5q | 112043202 | 112181936 | 24, 25, 26 |

As used herein, an "informative" characteristic, e.g., size, sequence, composition or amount of a marker refers to a characteristic, e.g., size, sequence, composition or amount whose value or difference is correlated to prognosis or outcome. The informative characteristic, e.g., size, sequence, composition or amount of a marker can be obtained by analyzing either nucleic acid, e.g., DNA or RNA, or protein corresponding to the marker gene. The characteristic, e.g., size (e.g., length or molecular weight), sequence (e.g., nucleic acid sequence or protein sequence), composition (e.g., base or amino acid composition or peptide digest or gene fragment pattern) or amount (e.g., copy number and/or expression level) of a marker, e.g., a chromosome locus marker or a marker in a sample from a patient can be "informative" if it is different than the wild type or allelic variant of the substance being analyzed. In some embodiments, a characteristic of a marker is informative if it indicates that the marker gene is wild type. In an embodiment where the amount of a marker is being measured, an amount is "informative" if it is greater than or less than a reference amount by a degree greater than the standard error of the assay employed to assess expression. The informative expression level of a marker can be determined upon statistical correlation of the measured expression level and the outcome, e.g., good response, poor response, long time-to-progression, short time-to-progression, short term survival or long term survival. The result of the statistical analysis can establish a threshold for selecting markers to use in the methods described herein. Alternatively, a marker, e.g., a chromosome locus marker, or a marker gene that has differential characteristic, e.g., size, sequence, composition or amounts will have typical ranges of amounts that are predictive of outcome. An informative characteristic, e.g., size, sequence, composition or amount is a characteristic, e.g., size, sequence, composition or amount that falls within the range of characteristic, e.g., size, sequence, composition or amounts determined for the outcome. Still further, a set of markers may together be "informative" if the combination of their characteristics, e.g., sizes, sequences, compositions or amounts either meets or is above or below a pre-determined score for a marker, e.g., a chromosome locus marker, or a marker gene, set as determined by methods provided herein. Gene translocation, transcript splice variation, deletion and truncation are examples of events which can change marker size, sequence or composition, in addition to point mutations which can change marker sequence or composition. Measurement of only one characteristic, e.g., marker, of a marker gene (i.e., DNA, RNA or protein) can provide a prognosis, i.e., indicate outcome. Measurement of more than one characteristic, e.g., marker, of a marker gene can provide a prognosis when the informative amounts of the two characteristics are consistent with each other, i.e., the biologies of the results are not contradictory. Examples of consistent results from measurement of multiple characteristics of a marker gene can be identification of a nonsense mutation or deletion in a DNA or RNA and a low amount or low molecular weight of encoded protein, or a mutation in a region which encodes a binding pocket or active site of a protein and low activity of the encoded protein. A different example can occur when a protein is in a pathway with a feedback loop controlling its synthesis based on its activity level. In this example, a low amount or activity of protein can be associated with a high amount of its mutated mRNA as a tissue, due to the marker gene mutation, thus is starved for the protein activity and repeatedly signals the production of the protein.

As used herein, "gene deletion" refers to an amount of DNA copy number less than 2 and "amplification" refers to an amount of DNA copy number greater than 2. A "diploid" amount refers to a copy number equal to 2. The term "diploid or amplification" can be interpreted as "not deletion" of a gene copy. In a marker whose alternative informative amount is gene deletion, amplification generally would not be seen. Conversely, the term "diploid or deletion" can be interpreted as "not amplification" of copy number. In a marker whose alternative informative amount is amplification, gene deletion generally would not be seen. For the sake of clarity, sequence deletion can occur within a gene as a result of marker gene mutation and can result in absence of transcribed protein or a shortened mRNA or protein. Such a deletion may not affect copy number.

The terms "long term survival" and "short term survival" refer to the length of time after receiving a first dose of treatment that a cancer patient is predicted to live. A "long term survivor" refers to a patient expected have a slower rate of progression or later death from the tumor than those patients identified as short term survivors. "Enhanced survival" or "a slower rate of death" are estimated life span determinations based upon characteristic, e.g., size, sequence, composition or amount of one or more of markers described herein, e.g., as compared to a reference standard such that 70%, 80%, 90% or more of the population will be alive a sufficient time period after receiving a first dose of treatment. A "faster rate of death" or "shorter survival time" refer to estimated life span determinations based upon characteristic, e.g., size, sequence, composition or amount of one or more of markers described herein, e.g., as compared to a reference standard such that 50%, 40%, 30%, 20%, 10% or less of the population will not live a sufficient time period after receiving a first dose of treatment. In some embodiments, the sufficient time period is at least 6, 12, 18, 24 or 30 months measured from the first day of receiving a cancer therapy.

A cancer is "responsive" to a therapeutic agent or there is a "good response" to a treatment if its rate of growth is inhibited as a result of contact with the therapeutic agent, compared to its growth in the absence of contact with the therapeutic agent. Growth of a cancer can be measured in a variety of ways, for instance, the characteristic, e.g., size of a tumor or the expression of tumor markers appropriate for that tumor type may be measured. For example, the response definitions used to support the identification of markers associated with myeloma and its response to an NAE inhibitor, such as a 1-substituted methyl sulfamate therapy, the Southwestern Oncology Group (SWOG) criteria as described in Blade et al. (1998) *Br J Haematol.* 102:1115-23 can be used. These criteria define the type of response measured in myeloma and also the characterization of time to disease progression which is another important measure of a tumor's sensitivity to a therapeutic agent. For solid tumors, the Response Evaluation Criteria in Solid Tumors (RECIST) guidelines (Eisenhauer et al. (2009) *E. J. Canc.* 45:228-247) can be used to support the identification of markers associated with solid tumors and response of solid tumors to an NAE inhibitor. International Working Groups convene periodically to set, update and publish response criteria for various types of cancers. Such published reports can be followed to support the identification of markers of the subject tumors and their response to NAE inhibitors. Examples are criteria for Acute Myelogenous Leukemia (AML, Cheson et al. (2003) *J. Clin. Oncol.* 21:4642-4649), lymphomas, e.g., non-Hodgkin's and Hodgkin's lymphoma (Cheson et al. (2007) *J. Clin. Oncol.* 25:579-596). Criteria take into account analysis methods such as Positron Emission Tomography (PET), e.g., for identifying sites with measurable altered metabolic activity (e.g., at tumor sites) or to trace specific markers into tumors in vivo, immunohistochemistry, e.g., to identify tumor cells by detecting binding of antibodies to specific tumor markers, and flow cytometry, e.g., to characterize cell types by differential markers and fluorescent stains, in addition to traditional methods such as histology to identify cell composition (e.g., blast counts in a blood smear or a bone marrow biopsy, presence and number of mitotic figures) or tissue structure (e.g., disordered tissue architecture or cell infiltration of basement membrane). The quality of being responsive to an NAE inhibitor, such as a 1-substituted methyl sulfamate therapy can be a variable one, with different cancers exhibiting different levels of "responsiveness" to a given therapeutic agent, under different conditions. Still further, measures of responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

A cancer is "non-responsive" or has a "poor response" to a therapeutic agent or there is a poor response to a treatment if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. For example, the response definitions used to support the identification of markers associated with non-response of tumors to therapeutic agents, guidelines such as those described above can be used. The quality of being non-responsive to a therapeutic agent can be a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc. In addition, clinical prognostic markers and variables can be assessed (e.g., M protein in myeloma, PSA levels in prostate cancer) in applicable situations.

As used herein, "long time-to-progression, "long TTP" and "short time-to-progression," "short TTP" refer to the amount of time until when the stable disease brought by treatment converts into an active disease. On occasion, a treatment results in stable disease which is neither a good nor a poor response, e.g., MR, the disease merely does not get worse, e.g., become a progressive disease, for a period of time. This period of time can be at least 4-8 weeks, at least 3-6 months or more than 6 months.

"Treatment" shall mean the use of a therapy to prevent or inhibit further tumor growth, as well as to cause shrinkage of a tumor, and to provide longer survival times. Treatment is also intended to include prevention of metastasis of tumor. A tumor is "inhibited" or "treated" if at least one symptom (as determined by responsiveness/non-responsiveness, time to progression, or indicators known in the art and described herein) of the cancer or tumor is alleviated, terminated, slowed, minimized, or prevented. Any amelioration of any symptom, physical or otherwise, of a tumor pursuant to treatment using a therapeutic regimen (e.g., NAE inhibitor, such as a 1-substituted methyl sulfamate regimen) as further described herein, is within the scope of the invention.

As used herein, the term "agent" is defined broadly as anything that cancer cells, including tumor cells, may be exposed to in a therapeutic protocol. In the context of the present invention, such agents include, but are not limited to, an NAE inhibitor, such as a 1-substituted methyl sulfamate agents, as well as chemotherapeutic agents as known in the art and described in further detail herein.

The term "probe" refers to any molecule, e.g., an isolated molecule, which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

A "normal" characteristic, e.g., size, sequence, composition or amount of a marker may refer to the characteristic, e.g., size, sequence, composition or amount in a "reference sample." A reference sample can be a matched normal, e.g., germline, sample from the same patient from whom the tumor, e.g., with a somatic mutation, is derived. A reference sample can be a sample from a healthy subject not having the marker-associated disease or a reference characteristic e.g., the average characteristic, e.g., size, sequence, composition or amount of the wild type marker in several healthy subjects. A reference sample characteristic, e.g., size, sequence, composition or amount may be comprised of a characteristic, e.g., size, sequence, composition or amount of one or more markers from a reference database. Alternatively, a "normal" characteristic, e.g., size, sequence, composition or level of expression of a marker is the characteristic, e.g., size, sequence, composition or amount of the marker, e.g., marker gene in non-tumor cells in a similar environment or response situation from the same patient from whom the tumor is derived. The normal amount of DNA copy number is 2 or diploid, with the exception of X-linked genes in males, where the normal DNA copy number is 1.

"Over-expression" and "under-expression" of a marker gene, refer to expression of the marker gene of a patient at a greater or lesser level (e.g. more than three-halves-fold, at least two-fold, at least three-fold, greater or lesser level etc.), respectively, than normal level of expression of the marker gene, e.g., as measured by mRNA or protein, in a test sample that is greater than the standard error of the assay employed to assess expression. A "significant" expression level may refer to a level which either meets or is above or below a pre-determined score for a marker gene set as determined by methods provided herein.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In an embodiment, the first region comprises a first portion and the second region comprises a second portion, whereby, when the first and second portions are arranged in an antiparallel fashion, at least about 50%, at least about 75%, at least about 90%, or at least about 95% or all of the nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue (i.e., by percent identity). By way of example, a region having the nucleotide sequence 5'-ATTGCC-3' and a region having the nucleotide sequence 5'-TATGGC-3' share homology with 50% identity. In one embodiment, the first region comprises a first portion and the second region comprises a second portion, whereby, at least about 50%, at least about 75%, at least about 90%, or at least about 95% of the nucleotide residue positions of each of the portions are occupied by the same nucleotide residue. In an embodiment of 100% identity, all nucleotide residue positions of each of the portions are occupied by the same nucleotide residue.

Unless otherwise specified herewithin, the terms "antibody" and "antibodies" broadly encompass naturally-occurring forms of antibodies, e.g., polyclonal antibodies (e.g., IgG, IgA, IgM, IgE) and monoclonal and recombinant antibodies such as single-chain antibodies, two-chain and multi-chain proteins, chimeric, CDR-grafted, human and humanized antibodies and multi-specific antibodies, as well as fragments and derivatives of all of the foregoing, which fragments (e.g., dAbs, scFv, Fab, $F(ab)'_2$, Fab') and derivatives have at least an antigenic binding site. Antibody derivatives may comprise a protein or chemical moiety conjugated to an antibody. The term "antibody" also includes synthetic and genetically engineered variants.

A "kit" is any article of manufacture (e.g., a package or container) comprising at least one reagent, e.g. a probe, for specifically detecting a marker or marker set of the invention. The article of manufacture may be promoted, distributed, sold or offered for sale as a unit for performing, e.g., in vitro, the methods of the present invention, e.g., on a sample having been obtained from a patient. The reagents included in such a kit can comprise at least one nucleic acid probe and, optionally, one or more primers and/or antibodies for use in detecting marker characteristics, e.g., size, sequence composition or amount, e.g., expression. In addition, a kit of the present invention can contain instructions which describe a suitable detection assay. Such a kit can be conveniently used, e.g., in a clinical or a contract testing setting, to generate information, e.g., on expression levels, characteristic, e.g., size, sequence or composition of one or more marker, to be recorded, stored, transmitted or received to allow for diagnosis, evaluation or treatment of patients exhibiting symptoms of cancer, in particular patients exhibiting the possible presence of a cancer capable of treatment with NAE inhibition therapy, including, e.g., hematological cancers e.g., myelomas (e.g., multiple myeloma), lymphomas (e.g., non-hodgkins lymphoma), leukemias (e.g., acute myelogenous leukemia), and solid tumors (e.g., tumors of skin, lung, breast, ovary, etc.).

The present methods and compositions are designed for use in diagnostics and therapeutics for a patient suffering from cancer. A cancer or tumor is treated or diagnosed according to the present methods. "Cancer" or "tumor" is intended to include any neoplastic growth in a patient, including an initial tumor and any metastases. The cancer can be of the hematological or solid tumor type. Hematological tumors include tumors of hematological origin, including, e.g., myelomas (e.g., multiple myeloma), leukemias (e.g., Waldenstrom's syndrome, chronic lymphocytic leukemia, acute myelogenous leukemia, chronic myelogenous leukemia, other leukemias), lymphomas (e.g., B-cell lymphomas, non-Hodgkin's lymphoma) and myelodysplastic syndrome. Solid tumors can originate in organs, and include cancers such as in skin, lung, brain, breast, prostate, ovary, colon, kidney, pancreas, liver, esophagus, stomach, intestine, bladder, uterus, cervix, head and neck, central nervous system, bone, testis, adrenal gland, etc. The cancer can comprise a cell in which a marker gene has a mutation. As used herein, cancer cells, including tumor cells, refer to cells that divide at an abnormal (increased) rate or whose control of growth or survival is different than for cells in the same tissue where the cancer cell arises or lives. Cancer cells include, but are not limited to, cells in carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

As used herein, the term "noninvasive" refers to a procedure which inflicts minimal harm to a subject. In the case of clinical applications, a noninvasive sampling procedure can be performed quickly, e.g., in a walk-in setting, typically without anaesthesia and/or without surgical implements or suturing. Examples of noninvasive samples include blood, serum, saliva, urine, buccal swabs, throat cultures, stool samples and cervical smears. Noninvasive diagnostic analyses include x-rays, magnetic resonance imaging, positron emission tomography, etc.

Described herein is the assessment of outcome for treatment of a tumor through measurement of the amount of pharmacogenomic markers. Also described are assessing the outcome by noninvasive, convenient or low-cost means, for example, from blood samples. Typical methods to determine extent of cancer or outcome of a hematological tumor, e.g., lymphoma, leukemia, e.g., acute myelogenous leukemia, myeloma (e.g., multiple myeloma) can employ bone marrow biopsy to collect tissue for genotype or phenotype, e.g., histological analysis. The invention provides methods for determining, assessing, advising or providing an appropriate therapy regimen for treating a tumor or managing disease in a patient. Monitoring a treatment using the kits and methods disclosed herein can identify the potential for unfavorable outcome and allow their prevention, and thus a savings in morbidity, mortality and treatment costs through adjustment in the therapeutic regimen, cessation of therapy or use of alternative therapy.

The term "biological sample" is intended to include a patient sample, e.g, tissue, cells, biological fluids and isolates thereof, isolated from a subject, as well as tissues, cells and fluids present within a subject and can be obtained from a patient or a normal subject. In hematological tumors of the bone marrow, e.g., myeloma tumors, primary analysis of the tumor can be performed on bone marrow samples. However, some tumor cells, (e.g., clonotypic tumor cells, circulating endothelial cells), are a percentage of the cell population in whole blood. These cells also can be mobilized into the blood during treatment of the patient with granulocyte-colony stimulating factor (G-CSF) in preparation for a bone marrow transplant, a standard treatment for hematological tumors, e.g., leukemias, lymphomas and myelomas. Examples of circulating tumor cells in multiple myeloma have been studied e.g., by Pilarski et al. (2000) *Blood* 95:1056-65 and Rigolin et al. (2006) *Blood* 107:2531-5. Thus, noninvasive samples, e.g., for in vitro measurement of markers to determine outcome of treatment, can include peripheral blood samples. Accordingly, cells within peripheral blood can be tested for marker amount. For patients with hematological tumors, a control, reference sample for normal characteristic, e.g., size, sequence, composition or amount can be obtained from skin or a buccal swab of the patient. For solid tumors, a typical tumor sample is a biopsy of the tumor and thus comprises solid tumor cells. Alternatively, a sample of tumor cells shed or scraped from the tumor site can be collected noninvasively, such as in blood, sputum, a nipple aspirate, urine, stool, cervical smear, etc. For solid tumors, a control reference sample for normal characteristic, e.g., size, sequence, composition or amount can be obtained from blood of the patient.

Blood collection containers can comprise an anti-coagulant, e.g., heparin or ethylene-diaminetetraacetic acid (EDTA), sodium citrate or citrate solutions with additives to preserve blood integrity, such as dextrose or albumin or buffers, e.g., phosphate. If the amount of marker is being measured by measuring the level of its DNA in the sample, a DNA stabilizer, e.g., an agent that inhibits DNAse, can be added to the sample. If the amount of marker is being measured by measuring the level of its RNA in the sample, an RNA stabilizer, e.g., an agent that inhibits RNAse, can be added to the sample. If the amount of marker is being measured by measuring the level of its protein in the sample, a protein stabilizer, e.g., an agent that inhibits proteases, can be added to the sample. An example of a blood collection container is PAXGENE® tubes (PREANALYTIX, Valencia, Calif.), useful for RNA stabilization upon blood collection. Peripheral blood samples can be modified, e.g., fractionated, sorted or concentrated (e.g., to result in samples enriched with tumor or depleted of tumor (e.g., for a reference sample)). Examples of modified samples include clonotypic myeloma cells, which can be collected by e.g., negative selection, e.g., separation of white blood cells from red blood cells (e.g., differential centrifugation through a dense sugar or polymer solution (e.g., FICOLL® solution (Amersham Biosciences division of GE healthcare, Piscataway, N.J.) or HISTOPAQUE®-1077 solution, Sigma-Aldrich Biotechnology LP and Sigma-Aldrich Co., St. Louis, Mo.)) and/or positive selection by binding B cells to a selection agent (e.g., a reagent which binds to a tumor cell or myeloid progenitor marker, such as CD34, CD38, CD138, or CD133, for direct isolation (e.g., the application of a magnetic field to solutions of cells comprising magnetic beads (e.g., from Miltenyi Biotec, Auburn, Calif.) which bind to the B cell markers) or fluorescent-activated cell sorting).

Alternatively, a tumor cell line, e.g., OCI-Ly3, OCI-Ly10 cell (Alizadeh et al. (2000) *Nature* 403:503-511), a RPMI 6666 cell, a SUP-B15 cell, a KG-1 cell, a CCRF-SB cell, an 8ES cell, a Kasumi-1 cell, a Kasumi-3 cell, a BDCM cell, an HL-60 cell, a Mo-B cell, a JM1 cell, a GA-10 cell or a B-cell lymphoma (e.g., BC-3) or a cell line or a collection of tumor cell lines (see e.g., McDermott et al. (2007) *PNAS* 104: 19936-19941 or ONCOPANEL™ anti-cancer tumor cell profiling screen (Ricerca Biosciences, Bothell, Wash.)) can be assayed. A skilled artisan readily can select and obtain the appropriate cells (e.g., from American Type Culture Collection (ATCC®), Manassas, Va.) that are used in the present method. If the compositions or methods are being used to predict outcome of treatment in a patient or monitor the effectiveness of a therapeutic protocol, then a tissue or blood sample having been obtained from the patient being treated is a useful source of cells or marker gene or gene products for an assay.

The sample, e.g., tumor, e.g., biopsy or bone marrow, blood or modified blood, (e.g., comprising tumor cells) and/or the reference, e.g., matched control (e.g., germline), sample can be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

In an embodiment, mutational status of a marker gene, e.g., a mutation in a marker can be identified by sequencing a nucleic acid, e.g., a DNA, RNA, cDNA or a protein correlated with the marker gene. There are several sequencing methods known in the art to sequence nucleic acids. A nucleic acid primer can be designed to bind to a region comprising a potential mutation site or can be designed to complement the mutated sequence rather than the wild type sequence. Primer pairs can be designed to bracket a region comprising a potential mutation in a marker gene. A primer or primer pair can be used for sequencing one or both strands of DNA corresponding to the marker gene. A primer can be used in conjunction with a probe, e.g., a nucleic acid probe, e.g., a hybridization probe, to amplify a region of interest prior to sequencing to boost sequence amounts for detection of a mutation in a marker gene. Examples of regions which can be sequenced include an entire gene, transcripts of the gene and a fragment of the gene or the transcript, e.g., one or more of exons or untranslated regions. Examples of mutations to target for primer selection and sequence or composition analysis can be found in public databases which collect mutation information, such as COSMIC and dbGaP. Some mutations of marker genes such as NF2, SMAD, KDM6A or FBXW7 are listed in Tables 8-11 in the Examples as examples of mutations that can be associated with sensitivity to NAE inhibition, e.g., inhibition by 1-methyl sulfamates, e.g., MLN4924.

Sequencing methods are known to one skilled in the art. Examples of methods include the Sanger method, the SEQUENOM™ method and Next Generation Sequencing (NGS) methods. The Sanger method, comprising using electrophoresis, e.g., capillary electrophoresis to separate primer-elongated labeled DNA fragments, can be automated for high-throughput applications. The primer extension sequencing can be performed after PCR amplification of regions of interest. Software can assist with sequence base calling and with mutation identification. SEQUENOM™ MASSARRAY® sequencing analysis (San Diego, Calif.) is a mass-spectrometry method which compares actual mass to expected mass of particular fragments of interest to identify mutations. NGS technology (also called "massively parallel sequencing" and "second generation sequencing") in general provides for much higher throughput than previous methods and uses a variety of approaches (reviewed in Zhang et al. (2011) *J. Genet. Genomics* 38:95-109 and Shendure and Hanlee (2008) *Nature Biotech.* 26:1135-1145). NGS methods can identify low frequency mutations in a marker in a sample. Some NGS methods (see, e.g., GS-FLX Genome Sequencer (Roche *Applied Science*, Branford, Conn.), Genome analyzer (Illumina, Inc. San Diego, Calif.) SOLID™ analyzer (Applied Biosystems, Carlsbad, Calif.), Polonator G.007 (Dover Systems, Salem, N.H.), HELISCOPE™ (Helicos Biosciences Corp., Cambridge, Mass.)) use cyclic array sequencing, with or without clonal amplification of PCR products spatially separated in a flow cell and various schemes to detect the labeled modified nucleotide that is incorporated by the sequencing enzyme (e.g., polymerase or ligase). In one NGS method, primer pairs can be used in PCR reactions to amplify regions of interest. Amplified regions can be ligated into a concatenated product. Clonal libraries are generated in the flow cell from the PCR or ligated products and further amplified ("bridge" or "cluster" PCR) for single-end sequencing as the polymerase adds a labeled, reversibly terminated base that is imaged in one of four channels, depending on the identity of the labeled base and then removed for the next cycle. Software can aid in the comparison to genomic sequences to identify mutations.

Composition of proteins and nucleic acids can be determined by many ways known in the art, such as by treating them in ways that cleave, degrade or digest them and then analyzing the components. Mass spectrometry, electrophoresis and chromatography can separate and define components for comparison. Mutations which cause deletions or insertions can be identified by size or charge differences in these methods. Protein digestion or restriction enzyme nucleic acid digestion can reveal different fragment patterns after some mutations. Antibodies that recognize particular mutant amino acids in their structural contexts can identify and detect these mutations in samples (see below).

In an embodiment, DNA, e.g., genomic DNA corresponding to the wild type or mutated marker can be analyzed both by in situ and by in vitro formats in a biological sample using methods known in the art. DNA can be directly isolated from the sample or isolated after isolating another cellular component, e.g., RNA or protein. Kits are available for DNA isolation, e.g., QIAAMP® DNA Micro Kit (Qiagen, Valencia, Calif.). DNA also can be amplified using such kits.

In another embodiment, mRNA corresponding to the marker can be analyzed both by in situ and by in vitro formats in a biological sample using methods known in the art. An example of a method for measuring expression level is included in the Examples. For example a nucleic acid probe can be used to hybridize to a marker and the amount of probe hybridized can be measured. Many expression detection methods use isolated RNA. For in vitro methods, any RNA isolation technique that does not select against the isolation of mRNA can be utilized for the purification of RNA from tumor cells (see, e.g., Ausubel et al., ed., *Current Protocols in Molecular Biology, John* Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155). RNA can be isolated using standard procedures (see e.g., Chomczynski and Sacchi (1987) *Anal. Biochem.* 162:156-159), solutions (e.g., trizol, TRI REAGENT® (Molecular Research Center, Inc., Cincinnati, Ohio; see U.S. Pat. No. 5,346,994) or kits (e.g., a QIAGEN® Group RNEASY® isolation kit (Valencia, Calif.) or LEUKOLOCK™ Total RNA Isolation System, Ambion division of Applied Biosystems, Austin, Tex.).

Additional steps may be employed to remove DNA from RNA samples. Cell lysis can be accomplished with a non-ionic detergent, followed by microcentrifugation to remove the nuclei and hence the bulk of the cellular DNA. DNA subsequently can be isolated from the nuclei for DNA analysis. In one embodiment, RNA is extracted from cells of the various types of interest using guanidinium thiocyanate lysis followed by CsCl centrifugation to separate the RNA from DNA (Chirgwin et al. (1979) *Biochemistry* 18:5294-99). Poly(A)+RNA is selected by selection with oligo-dT cellulose (see Sambrook et al. (1989) *Molecular Cloning—-A Laboratory Manual* (2nd ed.), Cold Spring Harbor Laboratory, Cold Spring Harbor, N.Y.). Alternatively, separation of RNA from DNA can be accomplished by organic extraction, for example, with hot phenol or phenol/chloroform/isoamyl alcohol. If desired, RNAse inhibitors may be added to the lysis buffer. Likewise, for certain cell types, it may be desirable to add a protein denaturation/digestion step to the protocol. For many applications, it is desirable to enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX® medium (see Ausubel et al. (1994) *Current Protocols In Molecular Biology*, vol. 2, *Current Protocols Publishing*, New York). Once bound, poly(A)+mRNA is eluted from the affinity column using 2 mM EDTA/0.1% SDS.

The characteristic of a marker of the invention in a biological sample, e.g., after obtaining a biological sample (e.g., a bone marrow sample, a tumor biopsy or a reference sample) from a test subject, may be assessed by any of a wide variety of well known methods for detecting or measuring the characteristic, e.g., of a nucleic acid (e.g., RNA, mRNA, genomic DNA, or cDNA) and/or translated protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods. These methods include gene array/chip technology, RT-PCR, TAQMAN® gene expression assays (Applied Biosystems, Foster City, Calif.), e.g., under GLP approved laboratory conditions, in situ hybridization, immunohistochemistry, immunoblotting, FISH (flourescence in situ hybridization), FACS analyses, northern blot, southern blot, INFINIUM® DNA analysis Bead Chips (Illumina, Inc., San Diego, Calif.), quantitative PCR, bacterial artificial chromosome arrays, single nucleotide polymorphism (SNP) arrays (Affymetrix, Santa Clara, Calif.) or cytogenetic analyses. The detection methods of the invention can thus be used to detect RNA, mRNA, protein, cDNA, or genomic DNA, for example, in a biological sample in vitro as well as in vivo. Furthermore, in vivo techniques for detection of a polypeptide or nucleic acid corresponding to a marker of the invention include introducing into a subject a labeled probe to detect the biomarker, e.g., a nucleic acid complementary to the transcript of a biomarker or a labeled antibody, Fc receptor or antigen directed against the polypeptide, e.g., wild type or mutant marker. For example, the antibody can be labeled with a radioactive isotope whose presence and location in a subject can be detected by standard imaging techniques. These assays can be conducted in a variety of ways. A skilled artisan can select from these or other appropriate and available methods based on the nature of the marker(s), tissue sample and mutation in question. Some methods are described in more detail in later sections. Different methods or combinations of methods could be appropriate in different cases or, for instance in different types of tumors or patient populations.

In vitro techniques for detection of a polypeptide corresponding to a marker of the invention include enzyme linked immunosorbent assays (ELISAs), Western blots, protein array, immunoprecipitations and immunofluorescence. In such examples, expression of a marker is assessed using an antibody (e.g., a radio-labeled, chromophore-labeled, fluorophore-labeled, or enzyme-labeled antibody), an antibody derivative (e.g., an antibody conjugated with a substrate or with the protein or ligand of a protein-ligand pair (e.g., biotin-streptavidin)), or an antibody fragment (e.g., a single-chain antibody, an isolated antibody hypervariable domain, etc.) which binds specifically with a marker protein or fragment thereof, e.g., a protein or fragment comprising a region which can be mutated or a portion comprising a mutated sequence, or a mutated residue in its structural context, including a marker protein which has undergone all or a portion of its normal post-translational modification. An antibody can detect a protein with an amino acid sequence selected from the group consisting of SEQ ID NO:3, 6, 10, 11, 14, 17, 20 and 23. Alternatively, an antibody can detect a mutated protein with a variant amino acid sequence selected from the group consisting of a mutant of SEQ ID NO:3, 6, 10, 11, 14, 17, 20 and 23. Residues listed as mutated in public databases such as COSMIC of dbGaP can be prepared in immunogenic compositions for generation of antibodies that will specifically recognize and bind to the mutant residues. Another method can employ pairs of antibodies, wherein one of the pair would bind a marker protein upstream, i.e. N-terminal to the region of expected mutation, e.g., nonsense or deletion and the other of the pair would bind the protein downstream. Wild type protein would bind both antibodies of the pair, but a protein with a nonsense or deletion mutation would bind only the N-terminal antibody of the pair. An assay such as a sandwich ELISA assay could detect a loss of quantity of the wild type protein in the tumor sample, e.g., in comparison to the reference sample, or a standard ELISA would comparison of the levels of binding of the antibodies to infer that a mutation is present in a tumor sample.

Indirect methods for determining the amount or functionality of a protein marker also include measurement of the activity of the protein. For example, a sample, or a protein isolated from the sample or expressed from nucleic acid isolated, cloned or amplified from the sample can be assessed for marker protein activity. NF2 activity can be measured by its ability to associate with binding partners, e.g., in a cell-free assay or in a cell-based assay. In an example, the ability of NF2 to bind to red blood cell membranes or p55/MPP1 can be measured (Seo et al. (2009) *Exp. Biol. Med.* 234:255-262). In another example, SMAD4 activity can be measured by its activity in signal transduction, e.g., in a cell-free assay or in a cell-based assay. In an example, the phosphorylation state of SMAD4 can be measured, the binding of SMAD4 to DNA at a Smad-binding element, e.g., in a gel shift assay or in a reporter assay (see, e.g., Kuang and Chen (2004) *Oncogene* 23:1021-1029), can be measured or the translocation of SMAD4 between the nucleus and cytoplasm can be visualized and quantified on cell images. In another example KDM6A activity can be measured by its ability to demethylate proteins, e.g., histones. For example, an assay can measure the level of demethylation of lysine 27 of histone 3 (Hong et al. (2007) *PNAS* 104:18439-18444). In another example, FBXW7 activity can be measured by its ability to bind cyclin E or to associate into the Skp-cullin-F-box ubiquitin ligase complex. In another example, TP53 activity can be measured by the ability to bind to DNA or to form tetramers.

In one embodiment, expression of a marker is assessed by preparing mRNA/cDNA (i.e., a transcribed polynucleotide) from cells in a patient sample, and by hybridizing the mRNA/cDNA with a reference polynucleotide, e.g., an isolated nucleic acid probe, e.g., a hybridization probe, which is a complement of a marker nucleic acid, or a fragment thereof cDNA can, optionally, be amplified using any of a variety of polymerase chain reaction methods prior to hybridization with the reference polynucleotide. Expression of one or more markers likewise can be detected using quantitative PCR to assess the level of expression of the marker(s). An example of the use of measuring mRNA levels is that an inactivating mutation in a marker gene can result in an altered level of mRNA in a cell. The level can be upregulated due to feedback signaling protein production in view of nonfunctional or absent protein or downregulated due to instability of an altered mRNA sequence. Alternatively, any of the many known methods of detecting mutations or variants (e.g. single nucleotide polymorphisms, deletions, etc., discussed above) of a marker of the invention may be used to detect occurrence of a mutation in a marker gene in a patient.

An example of direct measurement is quantification of transcripts. As used herein, the level or amount of expression refers to the absolute amount of expression of an mRNA encoded by the marker or the absolute amount of expression of the protein encoded by the marker. As an alternative to making determinations based on the absolute expression amount of selected markers, determinations may be based on normalized expression amounts. Expression amount can be normalized by correcting the absolute expression level of a marker upon comparing its expression to the expression of a control marker that is not a marker, e.g., in a housekeeping role that is constitutively expressed. Suitable markers for normalization also include housekeeping genes, such as the actin gene or beta-2 microglobulin. Reference markers for data normalization purposes include markers which are ubiquitously expressed and/or whose expression is not regulated by oncogenes. Constitutively expressed genes are known in the art and can be identified and selected according to the relevant tissue and/or situation of the patient and the analysis methods. Such normalization allows one to compare the expression level in one sample, to another sample, e.g., between samples from different times or different subjects. Further, the expression level can be provided as a relative expression level. The baseline of a genomic DNA sample, e.g., diploid copy number, can be determined by measuring amounts in cells from subjects without a tumor or in non-tumor cells from the patient. To determine a relative amount of a marker or marker set, the amount of the marker or marker set is determined for at least 1, or 2, 3, 4, 5, or more samples, e.g., 7, 10, 15, 20 or 50 or more samples in order to establish a baseline, prior to the determination of the expression level for the sample in question. To establish a baseline measurement, the mean amount or level of each of the markers or marker sets assayed in the larger number of samples is determined and this is used as a baseline expression level for the biomarkers or biomarker sets in question. The amount of the marker or marker set determined for the test sample (e.g., absolute level of expression) is then divided by the baseline value obtained for that marker or marker set. This provides a relative amount and aids in identifying abnormal levels of marker protein activity.

Probes based on the sequence of a nucleic acid molecule of the invention can be used to detect transcripts or genomic sequences corresponding to one or more markers of the invention. The probe can comprise a label group attached thereto, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a subject, e.g., detecting mRNA levels or determining whether a gene encoding the protein has been mutated or deleted.

In addition to the nucleotide sequences described in the database records described herein, it will be appreciated by those skilled in the art that DNA sequence polymorphisms that lead to changes in the amino acid sequence can exist within a population (e.g., the human population). Such genetic polymorphisms can exist among individuals within a population due to naturally occuring allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

Primers or nucleic acid probes comprise a nucleotide sequence complementary to a specific a marker or a mutated region thereof and are of sufficient length to selectively hybridize with a marker gene or nucleic acid associated with a marker gene, e.g., they can bind to the nucleic acid with base sequence specificity and remain bound, after washing. Primers and probes can be used to aid in the isolation and sequencing of marker nucleic acids. In one embodiment, the primer or nucleic acid probe, e.g., a substantially purified oligonucleotide, an isolated nucleic acid, comprises a region having a nucleotide sequence which hybridizes, e.g., under stringent conditions, to about 6, 8, 10, 12, 15, 20, 25, 30, 40, 50, 60, 75, 100, 200, 350, 500 or more consecutive nucleotides of a marker gene or a region comprising a mutation in a marker gene or transcript therefrom or a complement. In another embodiment, the primer or nucleic acid probe is capable of hybridizing to a marker nucleic acid comprising a nucleotide sequence of any sequence set forth in any of SEQ ID NOs:1, 2, 4, 5, 7, 8, 9, 12, 13, 15, 16, 18, 19, 21, 22, 24, 25 or a sequence on chromosome 22q from base pair 29999545 to 30094589, chromosome 18q from base pair 48556583 to 48611412, chromosome Xp from base pair 44732423 to 44971847, chromosome 4q from base pair 153242410 to 153456172, chromosome 17p from base pair 7571720 to 7590868, chromosome 9p from base pair 21967751 to 21994490, or a complement of any of the foregoing. For example, a primer or nucleic acid probe comprising a nucleotide sequence of at least about 10 consecutive nucleotides, at least about 15 consecutive nucleotides, at least about 25 consecutive nucleotides, at least about 35 consecutive nucleotides, at least about 50 consecutive nucleotides, or having from about 15 to about 20 nucleotides set forth in any of SEQ ID NOs: 1, 2, 4, 5, 7, 8, 9, 12, 13, 15, 16, 18, 19, 21, 22, 24, 25 or a sequence on chromosome 22q from base pair 29999545 to 30094589, chromosome 18q from base pair 48556583 to 48611412, chromosome Xp from base pair 44732423 to 44971847, chromosome 4q from base pair 153242410 to 153456172, chromosome 17p from base pair 7571720 to 7590868, chromosome 9p from base pair 21967751 to 21994490, or a complement of any of the foregoing are provided by the invention. Primers or nucleic acid probes having a sequence of more than about 25, 40 or 50 nucleotides are also within the scope of the invention. In another embodiment, a primer or nucleic acid probe can have a sequence at least 70%, at least 75%, 80% or 85%, or at least, 90%, 95% or 97% identical to the nucleotide sequence of any sequence set forth in any of SEQ ID NOs: 1, 2, 4, 5, 7, 8, 9, 12, 13, 15, 16, 18, 19, 21, 22, 24, 25 or a sequence on chromosome 22q from base pair 29999545 to 30094589, chromosome 18q from base pair 48556583 to 48611412, chromosome Xp from base pair 44732423 to 44971847, chromosome 4q from base pair 153242410 to 153456172, chromosome 17p from base pair 7571720 to 7590868, chromosome 9p from base pair 21967751 to 21994490, or a complement of any of the foregoing. Nucleic acid analogs can be used as binding sites for hybridization. An example of a suitable nucleic acid analogue is peptide nucleic acid (see, e.g., Egholm et al., *Nature* 363:566 568 (1993); U.S. Pat. No. 5,539,083).

In some embodiments, nucleic acid probe can be designed to bind to the wild type sequence, so the presence of a mutation in that region can cause a decrease, e.g., measurable decrease, in binding or hybridization by that probe. In another embodiment, a nucleic acid probe can be designed to bind to a mutant sequence, so the presence of a mutation in that region can cause an increase in binding or hybridization by that probe. In other embodiments, a probe and primer set or a primer pair can be designed to bracket a region in a marker that can have a mutation so amplification based on that set or pair can result in nucleic acids which can be sequenced to identify the mutation.

Primers or nucleic acid probes can be selected using an algorithm that takes into account binding energies, base composition, sequence complexity, cross-hybridization binding energies, and secondary structure (see Friend et al., International Patent Publication WO 01/05935, published Jan. 25, 2001; Hughes et al., *Nat. Biotech.* 19:342-7 (2001). Useful primers or nucleic acid probes of the invention bind sequences which are unique for each transcript, e.g., target mutated regions and can be used in PCR for amplifying, detecting and sequencing only that particular nucleic acid, e.g., transcript or mutated transcript. Examples of some mutations of marker genes, e.g., NF2, SMAD4, KDM6A and FBXW7 are found in Tables in the Examples (Tables 8-11). Other mutations are described in reference articles cited herein and in public databases described herein. One of skill in the art can design primers and nucleic acid probes for the markers disclosed herein or related markers with similar characteristics, e.g., markers on the chromosome loci, or mutations in different regions of the same marker gene described herein, using the skill in the art, e.g., adjusting the potential for primer or nucleic acid probe binding to standard sequences, mutants or allelic variants by manipulating degeneracy or GC content in the primer or nucleic acid probe. Computer programs that are well known in the art are useful in the design of primers with the required specificity and optimal amplification properties, such as Oligo version 5.0 (National Biosciences, Plymouth, Minn.). While perfectly complementary nucleic acid probes and primers can be used for detecting the markers described herein and mutants, polymorphisms or alleles thereof, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the nucleic acid probe or primer as long as the resulting probe or primer is still capable of specifically hybridizing to the target region.

An indication of treatment outcome can be assessed by studying the amount of 1 marker, 2 markers, 3 markers or 4 markers, or more, e.g., 5, 6, 7, 8, 9, 10, 15, 20, or 25 markers, or mutated portions thereof e.g., marker genes which participate in or interact with the cullin ring ligase pathway e.g., tumor suppressors, e.g., which can be inactivated by somatic mutation in cancer. Markers can be studied in combination with another measure of treatment outcome, e.g., biochemical markers (e.g., M protein in myeloma, kidney health marker such as proteinuria, serum levels of C-reactive protein or cytokeratin 19, cytokeratin fragment 21-1 (CYFRA21-1) for NSCLC, urine levels of fibrinogen/fibrinogen degradation products for bladder cancer, urine or blood levels of catecholamines for neuroblastoma, serum levels of carbohydrate antigen 19-9 (CA 19-9) or metabolic profiling for pancreatic cancer or blood levels of soluble mesothelin-related peptides (SMRP) in mesothelioma) or histology assessment (e.g., blast count, number of mitotic figures per unit area, depth measurement of invasion of melanoma tumors, esophageal tumors or bladder tumors).

Statistical methods can assist in the determination of treatment outcome upon measurement of the amount of markers, e.g., measurement of DNA, RNA or protein. The amount of one marker can be measured at multiple timepoints, e.g., before treatment, during treatment, after treatment with an agent, e.g., an NAE inhibitor. To determine the progression of change in expression of a marker from a baseline, e.g., over time, the expression results can be analyzed by a repeated measures linear regression model (Littell, Miliken, Stroup, Wolfinger, Schabenberger (2006) *SAS for Mixed Models,* $2^{nd}$ edition. SAS Institute, Inc., Cary, N.C.)):

$$Y_{ijk}-Y_{ij0}=Y_{ij0}+\text{treatment}_i+day_k+(\text{treatment}*day)_{ik}+\Sigma_{ijk} \quad \text{Equation 1}$$

where $Y_{ijk}$ is the $\log_2$ transformed expression (normalized to the housekeeping genes) on the $k^{th}$ day of the $j^{th}$ animal in the $i^{th}$ treatment, $Y_{ij0}$ is the defined baseline $\log_2$ transformed expression (normalized to the housekeeping genes) of the $j^{th}$ animal in the $i^{th}$ treatment, $day_k$ is treated as a categorical variable, and $\varepsilon_{ijk}$, is the residual error term. A covariance matrix (e.g., first-order autoregressive, compound symmetry, spatial power law) can be specified to model the repeated measurements on each animal over time. Furthermore, each treatment time point can be compared back to the same time point in the vehicle group to test whether the treatment value was significantly different from vehicle.

A number of other methods can be used to analyze the data. For instance, the relative expression values could be analyzed instead of the cycle number. These values could be examined as either a fold change or as an absolute difference from baseline. Additionally, a repeated-measures analysis of variance (ANOVA) could be used if the variances are equal across all groups and time points. The observed change from baseline at the last (or other) time point could be analyzed using a paired t-test, a Fisher exact test (p-value=$\Sigma$ P(X=x) from x=1 to the number of situations, e.g., mutations, tested that show sensitivity to NAE inhibition) for testing significance of data of small sample sizes, or a Wilcoxon signed rank test if the data is not normally distributed, to compare whether a tumor patient was significantly different from a normal subject.

A difference in amount from one timepoint to the next or from the tumor sample to the normal sample can indicate prognosis of treatment outcome. A baseline level can be determined by measuring expression at 1, 2, 3, 4, or more times prior to treatment, e.g., at time zero, one day, three days, one week and/or two weeks or more before treatment. Alternatively, a baseline level can be determined from a number of subjects, e.g., normal subjects or patients with the same health status or disorder, who do not undergo or have not yet undergone the treatment, as discussed above. Alternatively, one can use expression values deposited with the Gene Expression Omnibus (GEO) program at the National Center for Biotechnology Information (NCBI, Bethesda, Md.). For example, datasets of myeloma mRNA expression amounts sampled prior to proteasome inhibition therapy include GEO Accession number GSE9782, also analyzed in Mulligan, et al. (2006) *Blood* 109:3177-88 and GSE6477, also analyzed by Chng et al. (2007) *Cancer Res.* 67:292-9. To test the effect of the treatment on the tumor, the expression of the marker can be measured at any time or multiple times after some treatment, e.g., after 1 day, 2 days, 3 days, 5 days, 1 week, 2 weeks, 3 weeks, 4 weeks, 1 month, 2 months, 3 months and/or 6 or more months of treatment. For example, the amount of a marker can be measured once after some treatment, or at multiple intervals, e.g., 1-week, 2-week, 4-week or 2-month, 3-month or longer intervals during treatment. In some embodiments, the measurement of a marker during treatment can be compared to the same marker measurement at baseline. In other embodiments, the measurement of a marker during treatment can be compared to the same marker measurement at an earlier timepoint. Conversely, to determine onset of progressive disease after stopping the administration of a therapeutic regimen, the amount of the marker can be measured at any time or multiple times after, e.g., 1 day, 2 days, 3 days, 5 days, 1 week, 2 weeks, 3 weeks, 4 weeks, 1 month, 2 months, 3 months and/or 6 or more months after the last treatment. The measurement of a marker after treatment can be compared to the same marker measurement at the end of treatment. One of skill in the art would determine the timepoint or timepoints to assess the amount of the marker depending on various factors, e.g., the pharmacokinetics of the treatment, the treatment duration, pharmacodynamics of the treatment, age of the patient, the nature of the disorder or mechanism of action of the treatment. A trend in the negative direction or a decrease in the amount relative to baseline or a pre-determined standard of expression of a marker of sensitivity to NAE inhibition therapy, e.g., a decrease in a sensitivity marker identified in Table 3, can indicate a decrease in response of the tumor to the therapy, e.g., increase in resistance. A trend toward a favorable outcome relative to the baseline or a pre-determined standard of expression of a marker of treatment outcome indicates usefulness of the therapeutic regimen or continued benefit of the therapy. A trend toward an increase in a resistance marker e.g., an increase in a resistance marker identified in Table 3, can indicate an unfavorable outcome.

Any marker, e.g., marker gene or combination of marker, e.g., marker genes of the invention, or mutations thereof as well as any known markers in combination with the markers, e.g., marker genes of the invention, may be used in the compositions, kits, and methods of the present invention. In general, markers are selected for as great as possible ability to judge mutational status of a marker gene to predict outcome of treatment with NAE inhibitor. For example, the choice of markers are selected for as great as possible difference between the characteristic, e.g., size, sequence, composition or amount of the marker in samples comprising tumor cells and the characteristic, e.g., size, sequence, composition or amount of the same marker in control cells. Although this difference can be as small as the limit of detection of the method for assessing the amount of the marker, in another embodiment, the difference can be at least greater than the standard error of the assessment method. In the case of RNA or protein amount, a difference can be at least 1.5-, 2-, 3-, 4-, 5-, 6-, 7-, 8-, 9-, 10-, 15-, 20-, 25-, 100-, 500-, 1000-fold or greater. "Low" RNA or protein amount can be that expression relative to the overall mean across tumor samples (e.g., hematological tumor, e.g., myeloma) is low. In the case of amount of DNA, e.g., copy number, the amount is 0, 1, 2, 3, 4, 5, 6, or more copies. A deletion causes the copy number to be 0 or 1; an amplification causes the copy number to be greater than 2. The difference can be qualified by a confidence level, e.g., $p<0.05$, $p<0.02$, $p<0.01$ or lower p-value.

Measurement of more than one marker, e.g., a set of 2, 3, 4, 5, 6, 7, 8, 9, 10, 12, 15, 20, or 25 or more markers can provide an expression profile or a trend indicative of treatment outcome. In some embodiments, the marker set comprises no more than 2, 3, 4, 5, 6, 7, 8, 9, 10, 12, 15, 20, or 25 markers. In some embodiments, the marker set includes a plurality of chromosome loci, a plurality of marker genes, or a plurality of markers of one or more marker genes (e.g., nucleic acid and protein, genomic DNA and mRNA, or various combinations of markers described herein). Analysis of treatment outcome through assessing the amount of markers in a set can be accompanied by a statistical method, e.g., a weighted voting analysis which accounts for variables which can affect the contribution of the amount of a marker in the set to the class or trend of treatment outcome, e.g., the signal-to-noise ratio of the measurement or hybridization efficiency for each marker. A marker set, e.g., a set of 2, 3, 4, 5, 6, 7, 8, 9, 10, 12, 15, 20, or 25 or more markers, can comprise a primer, probe or primers to analyze at least one marker DNA or RNA described herein, e.g., a marker on chromosome 22q from base pair 29999545 to 30094589, chromosome 18q from base pair 48556583 to 48611412, chromosome Xp from base pair 44732423 to 44971847, chromosome 4q from base pair 153242410 to 153456172, chromosome 17p from base pair 7571720 to 7590868, chromosome 9p from base pair 21967751 to 21994490, NF2, SMAD4, KDM6A, FBXW7, TP53, CDKN2A, CDKN2A_p14, or a complement of any of the foregoing. A marker set, e.g., a set of at least 2, 3, 4, 5, 6, 7, 8, 9, 10, 12, 15, 20, or 25 or more markers, can comprise a primer, probe or primers to detect at least one or at least two or more markers, or at least 2, 3, 4, 5, 6, 7, 8, 9, 10, 12, 15, 20, or 25 or more mutations on the markers e.g., of NF2, SMAD4, KDM6A, TP53, CDKN2A, CDKN2A_p14 and/or FBXW7. In another embodiment, a marker set can comprise markers for assessing characteristics of NF2, SMAD4 and/or KDM6A. In an embodiment, a marker set for cancer of the uterus or cervix comprises at least one marker for assessing at least one characteristic of FBXW7. In an embodiment, a marker set for cancer of the intestine, breast, lung, head and neck, cervix or skin comprises at least one marker for assessing at least one characteristic of TP53. In an embodiment, a marker set for cancer of the intestine comprises markers for assessing at least one characteristic of each of TP53 and APC. In an embodiment, a marker set for cancer of the skin or central nervous system comprises at least one marker for assessing at least one characteristic of CDKN2A_p14. In an embodiment, a marker set for cancer of the head and neck or skin comprises at least one marker for assessing at least one characteristic of CDKN2A. In an embodiment, a marker set for cancer of the head and neck comprises at least one marker for assessing at least one characteristic of SMAD4. Selected marker sets can be assembled from the markers provided herein or selected from among markers using methods provided herein and analogous methods known in the art. A way to qualify a new marker for use in an assay of the invention is to correlate DNA copy number in a sample comprising tumor cells with differences in expression (e.g., fold-change from baseline) of a marker, e.g., a marker gene. A useful way to judge the relationship is to calculate the coefficient of determination r2, after solving for r, the Pearson product moment correlation coefficient and/or preparing a least squares plot, using standard statistical methods. A correlation can analyze DNA copy number versus the level of expression of marker, e.g., a marker gene. A gene product can be selected as a marker if the result of the correlation (r2, e.g., the linear slope of the data in this analysis), is at least 0.1-0.2, at least 0.3-0.5, or at least 0.6-0.8 or more. Markers can vary with a positive correlation to response, TTP or survival (i.e., change expression levels in the same manner as copy number, e.g., decrease when copy number is decreased). Markers which vary with a negative correlation to copy number (i.e., change expression levels in the opposite manner as copy number levels, e.g., increase when copy number is decreased) provide inconsistent determination of outcome.

Another way to qualify a new marker for use in the assay would be to assay the expression of large numbers of markers in a number of subjects before and after treatment with a test agent. The expression results allow identification of the markers which show large changes in a given direction after treatment relative to the pre-treatment samples. One can build a repeated-measures linear regression model to identify the genes that show statistically significant changes or differences. To then rank these significant genes, one can calculate the area under the change from e.g., baseline vs time curve. This can result in a list of genes that would show the largest statistically significant changes. Then several markers can be combined together in a set by using such methods as principle component analysis, clustering methods (e.g., k-means, hierarchical), multivariate analysis of variance (MANOVA), or linear regression techniques. To use such a gene (or group of genes) as a marker, genes which show 2-, 2.5-, 3-, 3.5-, 4-, 4.5-, 5-, 7-,10-fold, or more differences of expression from baseline would be included in the marker set. An expression profile, e.g., a composite of the expression level differences from baseline or reference of the aggregate marker set would indicate at trend, e.g., if a majority of markers show a particular result, e.g., a significant difference from baseline or reference, e.g., 60%, 70%, 80%, 90%, 95% or more markers; or more markers, e.g., 10% more, 20% more, 30% more, 40% more, show a significant result in one direction than the other direction.

In embodiments when the compositions, kits, and methods of the invention are used for characterizing treatment outcome in a patient, the marker or set of markers of the invention is selected such that a significant result is obtained in at least about 20%, at least about 40%, 60%, or 80%, or in substantially all patients treated with the test agent. The marker or set of markers of the invention can be selected such that a positive predictive value (PPV) of greater than about 10% is obtained for the general population and additional confidence in a marker can be inferred when the PPV is coupled with an assay specificity greater than 80%.

Therapeutic Agents

The markers and marker sets of the present invention assess the likelihood of favorable outcome of therapy (e.g., sensitivity to a therapeutic agent) in patients, e.g., cancer patients, e.g., patients having a hematological cancer (e.g., multiple myeloma, leukemias, lymphoma, etc) or solid tumor cancer (e.g., skin cancer such as melanoma, head and neck cancer, such as esophageal cancer, bladder cancer, lung cancer, such as non-small cell lung cancer (NSCLC), adenocarcinoma of the lung, central nervous system cancer such as lung metastases in the brain or neuroblastoma, pancreatic cancer, breast cancer, mesothelioma, cervical cancer or intestinal cancer such as colon or rectum adenocarcinoma), based on its ability to affect the characteristic, e.g., composition or amount of a marker or markers of the invention. Using this prediction, cancer therapies can be evaluated to design a therapy regimen best suitable for patients in either category.

In particular, the methods can be used to predict patient sensitivity to NAE inhibitors as described in earlier sections. The agents tested in the present methods can be a single agent or a combination of agents. The methods of the invention include combination of NAE inhibition therapy with proteasome inhibition therapy and/or other or additional agents, e.g., selected from the group consisting of chemotherapeutic agents. For example, the present methods can be used to determine whether a single chemotherapeutic agent, such as an NAE inhibitor (e.g., MLN4924) can be used to treat a cancer or whether a one or more agents should be used in combination with the NAE inhibitor (e.g., MLN4924). Useful combinations can include agents that have different mechanisms of action, e.g., the use of an anti-mitotic agent in combination with an alkylating agent and an NAE inhibitor.

As used herein, the term "proteasome inhibitor" refers to any substance which directly inhibits enzymatic activity of the 20S or 26S proteasome in vitro or in vivo. In some embodiments, the proteasome inhibitor is a peptidyl boronic acid. Examples of peptidyl boronic acid proteasome inhibitors suitable for use in the methods of the invention are disclosed in Adams et al., U.S. Pat. No. 5,780,454 (1998), U.S. Pat. No. 6,066,730 (2000), U.S. Pat. No. 6,083,903 (2000); U.S. Pat. No. 6,297,217 (2001), U.S. Pat. No. 6,465,433 (2002), U.S. Pat. No. 6,548,668 (2003), U.S. Pat. No. 6,617,317 (2003), and U.S. Pat. No. 6,747,150 (2004), each of which is hereby incorporated by reference in its entirety, including all compounds and formulae disclosed therein. In some embodiments, the peptidyl boronic acid proteasome inhibitor is selected from the group consisting of: N (4 morpholine)carbonyl-β-(1-naphthyl)-L-alanine-L-leucine boronic acid; N (8 quinoline)sulfonyl-β-(1-naphthyl)-L-alanine-L-alanine-L-leucine boronic acid; N (pyrazine)carbonyl-L-phenylalanine-L-leucine boronic acid, and N (4 morpholine)-carbonyl-[O-(2-pyridylmethyl)]-L-tyrosine-L-leucine boronic acid. In a particular embodiment, the proteasome inhibitor is N (pyrazine)carbonyl-L-phenylalanine-L-leucine boronic acid (bortezomib; VELCADE®; formerly known as MLN341 or PS-341). Publications describe the use of the disclosed boronic ester and boronic acid compounds to reduce the rate of muscle protein degradation, to reduce the activity of NF-κB in a cell, to reduce the rate of degradation of p53 protein in a cell, to inhibit cyclin degradation in a cell, to inhibit the growth of a cancer cell, and to inhibit NF-kB dependent cell adhesion. Bortezomib specifically and selectively inhibits the proteasome by binding tightly (Ki=0.6 nM) to one of the enzyme's active sites. Bortezomib is selectively cytotoxic, and has a novel pattern of cytotoxicity in National Cancer Institute (NCI) in vitro and in vivo assays. Adams J, et al. *Cancer Res* 59:2615-22. (1999).

Additionally, proteasome inhibitors include peptide aldehyde proteasome inhibitors (Stein et al., U.S. Pat. No. 5,693,617 (1997); Siman et al., international patent publication WO 91/13904; Iqbal et al., *J. Med. Chem.* 38:2276-2277 (1995); and Iinuma et al., international patent publication WO 05/105826, each of which is hereby incorporated by reference in its entirety), peptidyl epoxy ketone proteasome inhibitors (Crews et al., U.S. Pat. No. 6,831,099; Smyth et al., international patent publication WO 05/111008; Bennett et al., international patent publication WO 06/045066; Spaltenstein et al. *Tetrahedron Lett.* 37:1343 (1996); Meng, *Proc. Natl. Acad. Sci.* 96: 10403 (1999); and Meng, *Cancer Res.* 59: 2798 (1999)), alpha-ketoamide proteasome inhibitors (Chatterjee and Mallamo, U.S. Pat. No. 6,310,057 (2001) and U.S. Pat. No. 6,096,778 (2000); and Wang et al., U.S. Pat. No. 6,075,150 (2000) and U.S. Pat. No. 6,781,000 (2004)), peptidyl vinyl ester proteasome inhibitors (Marastoni et al., *J. Med. Chem.* 48:5038 (2005), and peptidyl vinyl sulfone and 2-keto-1,3,4-oxadiazole proteasome inhibitors, such as those disclosed in Rydzewski et al., *J. Med. Chem.* 49:2953 (2006); and Bogyo et al., *Proc. Natl. Acad. Sci.* 94:6629 (1997)), azapeptoids and (Bouget et al., *Bioorg. Med. Chem.* 11:4881 (2003); Baudy-Floc'h et al., international patent publication WO 05/030707; and Bonnemains et al., international patent publication WO 03/018557), efrapeptin oligopeptides (Papathanassiu, international patent publication WO 05/115431), lactacystin and salinosporamide and analogs thereof (Fenteany et al., U.S. Pat. No. 5,756,764 (1998), U.S. Pat. No. 6,147,223 (2000), U.S. Pat. No. 6,335,358 (2002), and U.S. Pat. No. 6,645,999 (2003); Fenteany et al., *Proc. Natl. Acad. Sci. USA* (1994) 91:3358; Fenical et al., international patent publication WO 05/003137; Palladino et al., international patent publication WO 05/002572; Stadler et al., international patent publication WO 04/071382; Xiao and Patel, U.S. patent publication 2005/023162; and Corey, international patent publication WO 05/099687).

Additional therapeutic agents for use in combination with an NAE inhibitor (e.g., MLN4924) in the methods of the invention can comprise a known class of therapeutic agents comprising glucocorticoid steroids. Glucocorticoid therapy generally comprises at least one glucocorticoid agent (e.g., dexamethasone). In certain applications of the invention, the agent used in methods of the invention is a glucocorticoid agent. One example of a glucocorticoid utilized in the treatment of multiple myeloma patients as well as other cancer therapies is dexamethasone. Additional glucocorticoids utilized in treatment of hematological and combination therapy in solid tumors include hydrocortisone, predisolone, prednisone, and triamcinolone.

Other therapeutic agents for use in combination with NAE inhibition therapy include chemotherapeutic agents. A "chemotherapeutic agent" is intended to include chemical reagents which inhibit the growth of proliferating cells or tissues wherein the growth of such cells or tissues is undesirable. Chemotherapeutic agents such as anti-metabolic agents, e.g., Ara AC, 5-FU and methotrexate, antimitotic agents, e.g., taxane, vinblastine and vincristine, alkylating agents, e.g., melphanlan, Carmustine (BCNU) and nitrogen mustard, Topoisomerase II inhibitors, e.g., VW-26, topotecan and Bleomycin, strand-breaking agents, e.g., doxorubicin and Mitoxantrone (DHAD), cross-linking agents, e.g., cisplatin and carboplatin (CBDCA), radiation and ultraviolet light and are well known in the art (see e.g., Gilman A. G., et al., *The Pharmacological Basis of Therapeutics,* 8th Ed., *Sec* 12:1202-1263 (1990)), and are typically used to treat neoplastic diseases. Examples of chemotherapeutic agents generally employed in chemotherapy treatments are listed below in Table 2.

TABLE 2

Chemotherapeutic Agents

| CLASS | TYPE OF AGENT | NONPROPRIETARY NAMES (OTHER NAMES) |
|---|---|---|
| Alkylating | Nitrogen Mustards | Mechlorethamine ($HN_2$) |
| | | Cyclophosphamide |
| | | Ifosfamide |
| | | Melphalan (L-sarcolysin) |
| | | Chlorambucil |
| | Ethylenimines | Hexamethylmelamine |
| | And Methylmelamines | Thiotepa |
| | Alkyl Sulfonates | Busulfan |
| Alkylating | Nitrosoureas | Carmustine (BCNU) |
| | | Lomustine (CCNU) |
| | | Semustine (methyl-CCNU) |
| | | Streptozocin (streptozotocin) |
| Alkylating | Triazene | Decarbazine (DTIC; dimethyltriazenoimidazolecarboxamide) |
| | Alkylator | cis-diamminedichloroplatinum II (CDDP) |
| Antimetabolites | Folic Acid Analogs | Methotrexate (amethopterin) |
| | Pyrimidine | Fluorouracil ('5-fluorouracil; 5-FU) |
| | Analogs | Floxuridine (fluorode-oxyuridine; FUdR) |
| | | Cytarabine (cytosine arabinoside) |
| | Purine Analogs and | Mercaptopuine (6-mercaptopurine; 6-MP) |
| | Related | Thioguanine (6-thioguanine; TG) |
| | Inhibitors | Pentostatin (2'-deoxycoformycin) |
| Natural | Vinca Alkaloids | Vinblastin (VLB) |
| Products | | Vincristine |
| | Topoisomerase | Etoposide |
| | Inhibitors | Teniposide |
| | | Camptothecin |
| | | Topotecan |
| | | 9-amino-campotothecin CPT-11 |
| | Antibiotics | Dactinomycin (actinomycin D) |
| | | Adriamycin |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | TAXOL |
| | | Taxotere |
| | Enzymes | L-Asparaginase |
| | Biological Response | Interfon alfa |
| | Modifiers | Interleukin 2 |
| | Platinum | cis-diamminedichloroplatinum II (CDDP) |
| | Coordination | Carboplatin |
| | Complexes | |
| | Anthracendione | Mitoxantrone |
| | Substituted Urea | Hydroxyurea |
| Miscellaneous | Methyl Hydraxzine | Procarbazine |
| Agents | Derivative | (N-methylhydrazine, (MIH) |
| | Adrenocortical | Mitotane (o,p'-DDD) |
| | Suppressant | Aminoglutethimide |
| Hormones and | Progestins | Hydroxyprogesterone caproate |
| Antagonists | | Medroxyprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin- | Leuprolide |
| | releasing | |
| | Hormone analog | |

The agents tested in the present methods can be a single agent or a combination of agents. For example, the present methods can be used to determine whether a single chemotherapeutic agent, such as methotrexate, can be used to treat a cancer or whether a combination of two or more agents can be used in combination with an NAE inhibitor (e.g., MLN4924). Useful combinations can include agents that have different mechanisms of action, e.g., the use of an anti-mitotic agent in combination with an alkylating agent and an NAE inhibitor.

The agents disclosed herein may be administered by any route, including intradermally, subcutaneously, orally, intraarterially or intravenously. In one embodiment, administration will be by the intravenous route. Parenteral administration can be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

Screens for NAE Inhibitors

The invention provides methods (also referred to herein as "screening assays") for identifying modulators, i.e., candidate or test compounds or agents (e.g., proteins, peptides, peptidomimetics, peptoids, small molecules or other drugs) which bind to NAE, or other E1 enzyme variant proteins, have a stimulatory or inhibitory effect on, for example, NAE, or other E1 enzyme expression or enzyme activity, or have a stimulatory or inhibitory effect on, for example, the expression or activity of a NAE, or other E1 enzyme substrate or proteins in the E1 enzyme pathway, e.g., in the NAE pathway, e.g. with a relationship to the activity of a cullin ring ligase. Compounds thus identified can be used to modulate the activity of target gene products (e.g., NAE, or other E1 enzyme genes) in a therapeutic protocol, to elaborate the biological function of the target gene product, or to identify compounds that disrupt NAE, or other E1 enzyme pathway interactions.

In one embodiment the invention provides a method of identifying a compound as an NAE inhibitor, e.g., as an agent that modulates the drug resistance of a cell, by first contacting a cell comprising at least one mutation in at least one marker gene with a test compound and then measuring the viability of the cell or the inhibition of the growth of the cell. In some embodiments, the cell comprises a resistance gene identified in Table 3. In other embodiments, the cell comprises a sensitivity gene identified in Table 3. The effect of the NAE inhibitor can be compared to a control cell not exposed to the compound. In some embodiments, the effect of an agent on a cell comprising a sensitivity marker gene can be compared with the effect of an agent on a cell comprising a resistance marker gene (see, e.g., Table 3). The compound is identified as modulator of drug resistance or an NAE inhibitor agent when the cell viability or cell growth is decreased. The compounds identified as an NAE inhibitor, e.g., as modulating resistance, that are identified in the foregoing methods are also included within the invention.

Detection Methods

A general principle of prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay. One example of such an embodiment includes use of an array or chip which contains a predictive marker or marker set anchored for expression analysis of the sample.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite. One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In an embodiment, the probe, when it is the unanchored assay component, can be labeled for the purpose of detection and readout of the assay, either directly or indirectly, with detectable labels discussed herein and which are well-known to one skilled in the art. The term "labeled", with regard to the probe (e.g., nucleic acid or antibody), is intended to encompass direct labeling of the probe by coupling (i.e., physically linking) a detectable substance to the probe, as well as indirect labeling of the probe by reactivity with another reagent that is directly labeled. An example of indirect labeling includes detection of a primary antibody using a fluorescently labeled secondary antibody. It is also possible to directly detect marker/probe complex formation without further manipulation or labeling of either component (marker or probe), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). As used herein, "BIA" or "surface plasmon resonance" is a technology for studying biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P. (1993) *Trends Biochem Sci.* 18:284-7). Standard chromatographic techniques also can be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H. (1998) *J. Mol. Recognit.* 11:141-8; Hage, D. S., and Tweed, S. A. (1997) *J. Chromatogr. B. Biomed. Sci. Appl.* 699:499-525). Gel electrophoresis may also be employed to separate complexed assay components from unbound components (see, e.g., Ausubel et al., ed., *Current Protocols in Molecular Biology, John* Wiley & Sons, New York, 1987-1999). In this technique, protein or nucleic acid complexes are separated based on size or charge, for example. In some embodiments, non-denaturing gel matrix materials and conditions in the absence of reducing agent are used in order to maintain the binding interaction during the electrophoretic process. Appropriate conditions to the particular assay and components thereof will be well known to one skilled in the art.

The isolated mRNA can be used in hybridization or amplification assays that include, but are not limited to, Southern or Northern analyses, polymerase chain reaction and TAQMAN® gene expression assays (Applied Biosystems, Foster City, Calif.) and probe arrays. One diagnostic method for the detection of mRNA levels involves contacting the isolated mRNA with a nucleic acid molecule (probe, e.g., a hybridization probe) that can hybridize to the mRNA encoded by the gene or mutant being detected. In some embodiments, nucleic acids comprising mutations of marker genes can be used as probes or primers. The nucleic acid probes or primers of the invention can be single stranded DNA (e.g., an oligonucleotide), double stranded DNA (e.g., double stranded oligonucleotide) or RNA. Primers of the invention refer to nucleic acids which hybridize to a nucleic acid sequence which is adjacent to the region of interest and can be extended over a region of interest, e.g., in a primer extension or amplification reaction, or which covers the region of interest, e.g., a nucleic acid region comprising a marker gene or mutation thereof. A nucleic acid probe can be, for example, a full-length cDNA, or a portion thereof, such as an oligonucleotide of at least 7, 15, 20, 25, 30, 50, 75, 100, 125, 150, 175, 200, 250 or 500 or more consecutive nucleotides of the marker nucleic acid sequence or complement thereof and sufficient to specifically hybridize under stringent conditions to a mRNA or genomic DNA encoding a marker of the present invention or a complement thereof. The exact length of the nucleic acid probe will depend on many factors that are routinely considered and practiced by the skilled artisan. Nucleic acid probes of the invention may be prepared by chemical synthesis using any suitable methodology known in the art, may be produced by recombinant technology, or may be derived from a biological sample, for example, by restriction digestion. Other suitable probes for use in the diagnostic assays of the invention are described herein. The probe can comprise a label group attached thereto, e.g., a radioisotope, a fluorescent compound, an enzyme, an enzyme co-factor, a hapten, a sequence tag, a protein or an antibody. The nucleic acids can be modified at the base moiety, at the sugar moiety, or at the phosphate backbone. An example of a nucleic acid label is incorporated using SUPER™ Modified Base Technology (Nanogen, Bothell, Wash., see U.S. Pat. No. 7,045,610). The level of expression can be measured as general nucleic acid levels, e.g., after measuring the amplified DNA levels (e.g. using a DNA intercalating dye, e.g., the SYBR green dye (Qiagen Inc., Valencia, Calif.) or as specific nucleic acids, e.g., using a probe based design, with the probes labeled. TAQMAN® assay formats can use the probe-based design to increase specificity and signal-to-noise ratio.

Such primers or probes can be used as part of a diagnostic test kit for identifying cells or tissues which express the protein, such as by measuring amounts of a nucleic acid molecule transcribed in a sample of cells from a subject, e.g., detecting transcript, mRNA levels or determining whether a gene encoding the protein has been mutated or deleted. Hybridization of an RNA or a cDNA with the nucleic acid probe can indicate that the marker in question is being expressed. The invention further encompasses detecting nucleic acid molecules that differ, due to degeneracy of the genetic code, from the nucleotide sequence of nucleic acids encoding a marker protein (e.g., protein having the sequence of the SEQ ID NOs:3, 6, 10, 11, 14, 17, 20, 23 or 26), and thus encode the same protein. It will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. Such natural allelic variations can typically result in 1-5% variance in the nucleotide sequence of a given gene. Alternative alleles can be identified by sequencing the gene of interest in a number of different individuals, e.g., normal samples from individuals. This can be readily carried out by using hybridization probes to identify the same genetic locus in a variety of individuals. Detecting any and all such nucleotide variations and resulting amino acid polymorphisms or variations that are the result of natural allelic variation and that do not alter the functional activity are intended to be within the scope of the invention. In addition, it will be appreciated that DNA polymorphisms that affect RNA expression levels can also exist that may affect the overall expression level of that gene (e.g., by affecting regulation or degradation).

As used herein, the term "hybridizes" is intended to describe conditions for hybridization and washing under which nucleotide sequences that are significantly identical or homologous to each other remain hybridized to each other. In some embodiments, the conditions are such that sequences at least about 70%, at least about 80%, at least about 85%, 90% or 95% identical to each other remain hybridized to each other for subsequent amplification and/or detection. Stringent conditions vary according to the length of the involved nucleotide sequence but are known to those skilled in the art and can be found or determined based on teachings in *Current Protocols in Molecular Biology*, Ausubel et al., eds., John Wiley & Sons, Inc. (1995), sections 2, 4 and 6. Additional stringent conditions and formulas for determining such conditions can be found in *Molecular Cloning: A Laboratory Manual*, Sambrook et al., Cold Spring Harbor Press, Cold Spring Harbor, N.Y. (1989), chapters 7, 9 and 11. A non-limiting example of stringent hybridization conditions for hybrids that are at least 10 basepairs in length includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A non-limiting example of highly stringent hybridization conditions for such hybrids includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions for such hybrids includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. Another example of stringent hybridization conditions are hybridization in 6× sodium chloride/sodium citrate (SSC) at about 45° C., followed by one or more washes in 0.2×SSC, 0.1% SDS at 50-65° C. A further example of stringent hybridization buffer is hybridization in 1 M NaCl, 50 mM 2-(N-morpholino)ethanesulfonic acid (MES) buffer (pH 6.5), 0.5% sodium sarcosine and 30% formamide. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6($\log_{10}[Na^+]$)+0.41(% G+C)−(600/N), where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, polyvinylpyrrolidone (PVP) and the like. When using nylon membranes, in particular, an additional non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81:1991-1995, (or alternatively 0.2×SSC, 1% SDS). A primer or nucleic acid probe can be used alone in a detection method, or a primer can be used together with at least one other primer or nucleic acid probe in a detection method. Primers can also be used to amplify at least a portion of a nucleic acid. Nucleic acid probes of the invention refer to nucleic acids which hybridize to the region of interest and which are not further extended. For example, a nucleic acid probe is a nucleic acid which specifically hybridizes to a mutant region of a biomarker, and which by hybridization or absence of hybridization to the DNA of a patient or the type of hybrid formed can be indicative of the presence or identity of the mutation of the biomarker or the amount of marker activity.

In one format, the RNA is immobilized on a solid surface and contacted with a probe, for example by running the isolated RNA on an agarose gel and transferring the RNA from the gel to a membrane, such as nitrocellulose. In an alternative format, the nucleic acid probe(s) are immobilized on a solid surface and the RNA is contacted with the probe(s), for example, in an AFFYMETRIX® gene chip array or a SNP chip (Santa Clara, Calif.) or customized array using a marker set comprising at least one marker indicative of treatment outcome. A skilled artisan can readily adapt known RNA and DNA detection methods for use in detecting the amount of the markers of the present invention. For example, the high density microarray or branched DNA assay can benefit from a higher concentration of tumor cell in the sample, such as a sample which had been modified to isolate tumor cells as described in earlier sections. In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues) of a marker nucleic acid. If polynucleotides complementary to or homologous with the marker are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). In an embodiment when a method of assessing marker expression is used which involves hybridization of one nucleic acid with another, the hybridization can be performed under stringent hybridization conditions.

An alternative method for determining the amount of RNA corresponding to a marker of the present invention in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to about 30 nucleotides in length and flank a region from about 50 to about 200 nucleotides in length. Under appropriate conditions and with appropriate reagents, such primers permit the amplification of a nucleic acid molecule comprising the nucleotide sequence flanked by the primers.

For in situ methods, RNA does not need to be isolated from the cells prior to detection. In such methods, a cell or tissue sample is prepared/processed using known histological methods. The sample is then immobilized on a support, typically a glass slide, and then contacted with a probe that can hybridize to RNA that encodes the marker.

In another embodiment of the present invention, a polypeptide corresponding to a marker is detected. In some embodiments, an agent for detecting a polypeptide of the invention is an antibody capable of binding to a polypeptide corresponding to a marker of the invention. In related embodiments, the antibody has a detectable label. Antibodies can be polyclonal, or monoclonal. An intact antibody, or a fragment thereof (e.g., Fab or $F(ab')_2$) can be used.

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether B cells express a marker of the present invention.

Another method for determining the level of a polypeptide corresponding to a marker is mass spectrometry. For example, intact proteins or peptides, e.g., tryptic peptides can be analyzed from a sample, e.g., a blood sample, a lymph sample or other sample, containing one or more polypeptide markers. The method can further include treating the sample to lower the amounts of abundant proteins, e.g., serum albumin, to increase the sensitivity of the method. For example, liquid chromatography can be used to fractionate the sample so portions of the sample can be analyzed separately by mass spectrometry. The steps can be performed in separate systems or in a combined liquid chromatography/mass spectrometry system (LC/MS, see for example, Liao, et al. (2004)*Arthritis Rheum.* 50:3792-3803). The mass spectrometry system also can be in tandem (MS/MS) mode. The charge state distribution of the protein or peptide mixture can be acquired over one or multiple scans and analyzed by statistical methods, e.g. using the retention time and mass-to-charge ratio (m/z) in the LC/MS system, to identify proteins expressed at statistically significant levels differentially in samples from patients responsive or non-responsive to NAE inhibition therapy. Examples of mass spectrometers which can be used are an ion trap system (ThermoFinnigan, San Jose, Calif.) or a quadrupole time-of-flight mass spectrometer (Applied Biosystems, Foster City, Calif.). The method can further include the step of peptide mass fingerprinting, e.g. in a matrix-assisted laser desorption ionization with time-of-flight (MALDI-TOF) mass spectrometry method. The method can further include the step of sequencing one or more of the tryptic peptides. Results of this method can be used to identify proteins from primary sequence databases, e.g., maintained by the National Center for Biotechnology Information, Bethesda, Md., or the Swiss Institute for Bioinformatics, Geneva, Switzerland, and based on mass spectrometry tryptic peptide m/z base peaks.

Electronic Apparatus Readable Arrays

Electronic apparatus, including readable arrays comprising at least one predictive marker of the present invention is also contemplated for use in conjunction with the methods of the invention. As used herein, "electronic apparatus readable media" refers to any suitable medium for storing, holding or containing data or information that can be read and accessed directly by an electronic apparatus. As used herein, the term "electronic apparatus" is intended to include any suitable computing or processing apparatus or other device configured or adapted for storing data or information. Examples of electronic apparatus suitable for use with the present invention and monitoring of the recorded information include stand-alone computing apparatus; networks, including a local area network (LAN), a wide area network (WAN) Internet, Intranet, and Extranet; electronic appliances such as personal digital assistants (PDAs), cellular phone, pager and the like; and local and distributed processing systems. As used herein, "recorded" refers to a process for storing or encoding information on the electronic apparatus readable medium. Those skilled in the art can readily adopt any of the presently known methods for recording information on known media to generate manufactures comprising the markers of the present invention.

For example, microarray systems are well known and used in the art for assessment of samples, whether by assessment gene expression (e.g., DNA detection, RNA detection, protein detection), or metabolite production, for example. Microarrays for use according to the invention include one or more probes of predictive marker(s) of the invention characteristic of response and/or non-response to a therapeutic regimen as described herein. In one embodiment, the microarray comprises one or more probes corresponding to one or more of markers selected from the group consisting of markers which demonstrate increased expression in short term survivors, and genes which demonstrate increased expression in long term survivors in patients. A number of different microarray configurations and methods for their production are known to those of skill in the art and are disclosed, for example, in U.S. Pat. Nos. 5,242,974; 5,384,261; 5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 5,981,185; 6,022,963; 6,077,674; 6,156,501; 6,261,776; 6,346,413; 6,440,677; 6,451,536; 6,576,424; 6,610,482; 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; Shena, et al. (1998), *Tibtech* 16:301; Duggan et al. (1999) *Nat. Genet.* 21:10; Bowtell et al. (1999) *Nat. Genet.* 21:25; Lipshutz et al. (1999) *Nature Genet.* 21:20-24, 1999; Blanchard, et al. (1996) *Biosensors and Bioelectronics,* 11:687-90; Maskos, et al., (1993) *Nucleic Acids Res.* 21:4663-69; Hughes, et al. (2001) *Nat. Biotechol.* 19:342, 2001; each of which are herein incorporated by reference. A tissue microarray can be used for protein identification (see Hans et al. (2004)*Blood* 103:275-282). A phage-epitope microarray can be used to identify one or more proteins in a sample based on whether the protein or proteins induce auto-antibodies in the patient (Bradford et al. (2006) *Urol. Oncol.* 24:237-242).

A microarray thus comprises one or more probes corresponding to one or more markers identified herein, e.g., those indicative of treatment outcome, e.g., to identify wild type marker genes, normal allelic variants and mutations of marker genes. The microarray can comprise probes corresponding to, for example, at least 2, at least 3, at least 4, at least 5, at least 10, at least 15, at least 20, at least 25, at least 30, at least 35, at least 40, at least 45, at least 50, at least 75, or at least 100, biomarkers and/or mutations thereof indicative of treatment outcome. The microarray can comprise probes corresponding to one or more biomarkers as set forth herein. Still further, the microarray may comprise complete marker sets as set forth herein and which may be selected and compiled according to the methods set forth herein. The microarray can be used to assay expression of one or more predictive markers or predictive marker sets in the array. In one example, the array can be used to assay more than one predictive marker or marker set expression in a sample to ascertain an expression profile of markers in the array. In this manner, up to about 44,000 markers can be simultaneously assayed for expression. This allows an expression profile to be developed showing a battery of markers specifically expressed in one or more samples. Still further, this allows an expression profile to be developed to assess treatment outcome.

The array is also useful for ascertaining differential expression patterns of one or more markers in normal and abnormal (e.g., sample, e.g., tumor) cells. This provides a battery of markers that could serve as a tool for ease of identification of treatment outcome of patients. Further, the array is useful for ascertaining expression of reference markers for reference expression levels. In another example, the array can be used to monitor the time course of expression of one or more markers in the array.

In addition to such qualitative determination, the invention allows the quantification of marker expression. Thus, predictive markers can be grouped on the basis of marker sets or outcome indications by the amount of the marker in the sample. This is useful, for example, in ascertaining the outcome of the sample by virtue of scoring the amounts according to the methods provided herein.

The array is also useful for ascertaining the effect of the expression of a marker on the expression of other predictive markers in the same cell or in different cells. This provides, for example, a selection of alternate molecular targets for therapeutic intervention if patient is predicted to have an unfavorable outcome.

Reagents and Kits

The invention also encompasses kits for detecting the presence of a polypeptide or nucleic acid corresponding to a marker of the invention in a biological sample (e.g. a bone marrow sample, tumor biopsy or a reference sample). Such kits can be used to determine mutational status of at least one marker gene to assess treatment outcome, e.g., determine if a subject can have a favorable outcome, e.g., after NAE inhibitor treatment. For example, the kit can comprise a labeled compound or agent capable of detecting a genomic DNA segment, a polypeptide or a transcribed RNA corresponding to a marker of the invention or a mutation of a marker gene in a biological sample and means for determining the amount of the genomic DNA segment, the polypeptide or RNA in the sample. Suitable reagents for binding with a marker protein include antibodies, antibody derivatives, antibody fragments, and the like. Suitable reagents for binding with a marker nucleic acid (e.g., a genomic DNA, an mRNA, a spliced mRNA, a cDNA, or the like) include complementary nucleic acids. The label can be directly attached to the marker binding agent, e.g., probe, e.g., nucleic acid reagent such as a probe or primer or protein reagent, such as a specific binding agent or antibody, or a secondary reagent can comprise a label for indirect labeling. The kit can also contain a control or reference sample or a series of control or reference samples which can be assayed and compared to the test sample. For example, the kit may have a positive control sample, e.g., including one or more markers or mutations described herein, or reference markers, e.g. housekeeping markers to standardize the assay among samples or timepoints or reference genomes, e.g., form subjects without tumor e.g., to establish diploid copy number baseline or reference expression level of a marker. By way of example, the kit may comprise fluids (e.g., buffer) suitable for annealing complementary nucleic acids or for binding an antibody with a protein with which it specifically binds and one or more sample compartments. The kit of the invention may optionally comprise additional components useful for performing the methods of the invention, e.g., a sample collection vessel, e.g., a tube, and optionally, means for optimizing the amount of marker detected, for example if there may be time or adverse storage and handling conditions between the time of sampling and the time of analysis. For example, the kit can contain means for increasing the number of tumor cells in the sample, as described above, a buffering agent, a preservative, a stabilizing agent or additional reagents for preparation of cellular material or probes for use in the methods provided; and detectable label, alone or conjugated to or incorporated within the provided probe(s). In one exemplary embodiment, a kit comprising a sample collection vessel can comprise e.g., a tube comprising anti-coagulant and/or stabilizer, e.g., an RNA stabilizer, as described above, or known to those skilled in the art. The kit can further comprise components necessary for detecting the detectable label (e.g., an enzyme or a substrate). For marker sets, the kit can comprise a marker set array or chip for use in detecting the biomarkers. Kits also can include instructions for interpreting the results obtained using the kit. The kit can contain reagents for detecting one or more biomarkers, e.g., 2, 3, 4, 5, or more biomarkers described herein.

In one embodiment, the kit comprises a probe to detect at least one biomarker, e.g., a marker indicative of treatment outcome (e.g., upon NAE inhibitor treatment). In an exemplary embodiment, the kit comprises a nucleic acid probe to detect a marker gene selected from the group consisting of SEQ ID NO: 1, 2, 4, 5, 7, 8, 9, 12, 13, 15, 16, 18, 19, 21, 22, 24, 25 or a sequence on chromosome 22q from base pair 29999545 to 30094589, chromosome 18q from base pair 48556583 to 48611412, chromosome Xp from base pair 44732423 to 44971847, chromosome 4q from base pair 153242410 to 153456172, chromosome 17p from base pair 7571720 to 7590868, chromosome 9p from base pair 21967751 to 21994490, or a complement of any of the foregoing or SEQ ID NO: 3, 6, 10, 11, 14, 17, 20, 23 and/or 26. In some embodiments, the kit comprises a probe to detect a marker selected from the group consisting of NF2, SMAD4, KDM6A, FBXW7, TP53, CDKN2A, CDKN2A_p14 and APC. In other embodiments, the kit comprises a probe to detect a mutation in a marker gene selected from the group consisting of NF2, SMAD4, KDM6A, FBXW7, TP53, CDKN2A, CDKN2A_p14 and APC. In an embodiment, a kit comprises probes to detect a marker set comprising two or more markers from the group consisting of NF2, SMAD4, KDM6A, FBXW7, TP53, CDKN2A, CDKN2A_p14 and APC. In another embodiment, a kit comprises a probe to detect FBXW7 in cancer of the uterus or cervix. In an embodiment, a kit comprises a probe to detect TP53 in cancer of the intestine, breast, lung, head and neck, cervix or skin. In an embodiment, a kit comprises a probe to detect TPC and APC in cancer of the intestine. In an embodiment, a kit comprises a probe to detect CDKN2A_p14 in cancer of the skin or central nervous system. In an embodiment, a kit comprises a probe to detect CDKN2A in cancer of the head and neck or skin. In an embodiment, a kit comprises a probe to detect SMAD4 in cancer of the head and neck. In related embodiments, the kit comprises a nucleic acid probe comprising or derived from (e.g., a fragment, mutant or variant (e.g., homologous or complementary) thereof) a nucleic acid sequence selected from the group consisting of SEQ ID NOs: 1, 2, 4, 5, 7, 8, 9, 12, 13, 15, 16, 18, 19, 21, 22, 24, and 25. For kits comprising nucleic acid probes, e.g., oligonucleotide-based kits, the kit can comprise, for example: one or more nucleic acid reagents such as an oligonucleotide (labeled or non-labeled) which hybridizes to a nucleic acid sequence corresponding to a marker of the invention, optionally fixed to a substrate; and can optionally further comprise labeled oligonucleotides not bound with a substrate, a primer, a pair of PCR primers, e.g., useful for amplifying a nucleic acid molecule corresponding to a marker of the invention, molecular beacon probes, a marker set comprising oligonucleotides which hybridize to at least two nucleic acid sequences corresponding to markers of the invention, and the like. The kit can contain an RNA-stabilizing agent.

For kits comprising protein probes, e.g., ligand or antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label. The kit can contain a protein stabilizing agent. The kit can contain reagents to reduce the amount of non-specific binding of non-biomarker material from the sample to the probe. Examples of reagents to reduce non-specific binding include nonioinic detergents, non-specific protein containing solutions, such as those containing albumin or casein, or other substances known to those skilled in the art.

An isolated polypeptide corresponding to a predictive marker of the invention, or a fragment or mutant thereof, can be used as an immunogen to generate antibodies using standard techniques for polyclonal and monoclonal antibody preparation. For example, an immunogen typically is used to prepare antibodies by immunizing a suitable (i.e., immunocompetent) subject such as a rabbit, goat, mouse, or other mammal or vertebrate. In still a further aspect, the invention provides monoclonal antibodies or antigen binding fragments thereof, which antibodies or fragments specifically bind to a polypeptide comprising an amino acid sequence selected from the group consisting of the amino acid sequences of the present invention, an amino acid sequence encoded by the cDNA of the present invention, a fragment of at least 8, 10, 12, 15, 20 or 25 consecutive amino acid residues of an amino acid sequence of the present invention, an amino acid sequence which is at least 95%, 96%, 97%, 98% or 99% identical to an amino acid sequence of the present invention (wherein the percent identity is determined using the ALIGN program of the GCG software package with a PAM120 weight residue table, a gap length penalty of 12, and a gap penalty of 4) and an amino acid sequence which is encoded by a nucleic acid molecule which hybridizes to a nucleic acid molecule consisting of the nucleic acid molecules of the present invention, or a complement thereof, under conditions of hybridization of 6×SSC at 45° C. and washing in 0.2×SSC, 0.1% SDS at 65° C. The monoclonal antibodies can be human, humanized, chimeric and/or non-human antibodies. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Methods for making human antibodies are known in the art. One method for making human antibodies employs the use of transgenic animals, such as a transgenic mouse. These transgenic animals contain a substantial portion of the human antibody producing genome inserted into their own genome and the animal's own endogenous antibody production is rendered deficient in the production of antibodies. Methods for making such transgenic animals are known in the art. Such transgenic animals can be made using XENOMOUSE™ technology or by using a "minilocus" approach. Methods for making XENOMICE™ are described in U.S. Pat. Nos. 6,162,963, 6,150,584, 6,114,598 and 6,075,181, which are incorporated herein by reference. Methods for making transgenic animals using the "minilocus" approach are described in U.S. Pat. Nos. 5,545,807, 5,545,806 and 5,625,825; also see International Publication No. WO93/12227, which are each incorporated herein by reference.

Antibodies include immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546 (1989)), which consists of a VH domain; (vii) a single domain functional heavy chain antibody, which consists of a VHH domain (known as a nanobody) see e.g., Cortez-Retamozo, et al., *Cancer Res.* 64: 2853-2857(2004), and references cited therein; and (vii) an isolated complementarity determining region (CDR), e.g., one or more isolated CDRs together with sufficient framework to provide an antigen binding fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. *Science* 242:423-426 (1988); and Huston et al. *Proc. Natl. Acad. Sci. USA* 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antibody fragments, such as Fv, $F(ab')_2$ and Fab may be prepared by cleavage of the intact protein, e.g. by protease or chemical cleavage. The invention provides polyclonal and monoclonal antibodies. Synthetic and genetically engineered variants (See U.S. Pat. No. 6,331,415) of any of the foregoing are also contemplated by the present invention. Polyclonal and monoclonal antibodies can be produced by a variety of techniques, including conventional murine monoclonal antibody methodology e.g., the standard somatic cell hybridization technique of Kohler and Milstein, *Nature* 256: 495 (1975) the human B cell hybridoma technique (see Kozbor et al., 1983, *Immunol. Today* 4:72), the EBV-hybridoma technique (see Cole et al., pp. 77-96 In Monoclonal Antibodies and Cancer Therapy, Alan R. Liss, Inc., 1985) or trioma techniques. See generally, Harlow, E. and Lane, D. (1988) *Antibodies: A Laboratory Manual*, Cold Spring Harbor Laboratory Press, Cold Spring Harbor, N.Y.; and *Current Protocols in Immunology*, Coligan et al. ed., John Wiley & Sons, New York, 1994. For diagnostic applications, the antibodies can be monoclonal antibodies, e.g., generated in mouse, rat, or rabbit. Additionally, for use in in vivo applications the antibodies of the present invention can be human or humanized antibodies. Hybridoma cells producing a monoclonal antibody of the invention are detected by screening the hybridoma culture supernatants for antibodies that bind the polypeptide of interest, e.g., using a standard ELISA assay.

If desired, the antibody molecules can be harvested or isolated from the subject (e.g., from the blood or serum of the subject) and further purified by well-known techniques, such as protein A chromatography to obtain the IgG fraction. Alternatively, antibodies specific for a protein or polypeptide of the invention can be selected or (e.g., partially purified) or purified by, e.g., affinity chromatography to obtain substantially purified and purified antibody. By a substantially purified antibody composition is meant, in this context, that the antibody sample contains at most only 30% (by dry weight) of contaminating antibodies directed against epitopes other than those of the desired protein or polypeptide of the invention, and at most 20%, at most 10%, or at most 5% (by dry weight) of the sample is contaminating antibodies. A purified antibody composition means that at least 99% of the antibodies in the composition are directed against the desired protein or polypeptide of the invention.

An antibody directed against a polypeptide corresponding to a marker of the invention (e.g., a monoclonal antibody) can be used to detect the marker (e.g., in a cellular sample) in order to evaluate the level and pattern of expression of the marker. The antibodies can also be used diagnostically to monitor protein levels in tissues or body fluids (e.g. in a blood sample or urine) as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Accordingly, in one aspect, the invention provides substantially purified antibodies or fragments thereof, and non-human antibodies or fragments thereof, which antibodies or fragments specifically bind to a polypeptide comprising an amino acid sequence encoded by a marker identified herein. The substantially purified antibodies of the invention, or fragments thereof, can be human, non-human, chimeric and/or humanized antibodies.

In another aspect, the invention provides non-human antibodies or fragments thereof, which antibodies or fragments specifically bind to a polypeptide comprising an amino acid sequence which is encoded by a nucleic acid molecule of a predictive marker of the invention. Such non-human antibodies can be goat, mouse, sheep, horse, chicken, rabbit, or rat antibodies. Alternatively, the non-human antibodies of the invention can be chimeric and/or humanized antibodies. In addition, the non-human antibodies of the invention can be polyclonal antibodies or monoclonal antibodies.

The substantially purified antibodies or fragments thereof may specifically bind to a signal peptide, a secreted sequence, an extracellular domain, a transmembrane or a cytoplasmic domain or cytoplasmic loop of a polypeptide of the invention. The substantially purified antibodies or fragments thereof, the non-human antibodies or fragments thereof, and/or the monoclonal antibodies or fragments thereof, of the invention specifically bind to a secreted sequence or an extracellular domain of the amino acid sequences of the present invention.

The invention also provides a kit containing an antibody of the invention conjugated to a detectable substance, and instructions for use. Still another aspect of the invention is a diagnostic composition comprising a probe of the invention and a pharmaceutically acceptable carrier. In one embodiment, the diagnostic composition contains an antibody of the invention, a detectable moiety, and a pharmaceutically acceptable carrier.

Sensitivity Assays

A sample of cancerous cells is obtained from a patient. An expression level is measured in the sample for a marker corresponding to at least one of the markers described herein. A marker set can be utilized comprising markers identified described herein, and put together in a marker set using the methods described herein. Such analysis is used to obtain an expression profile of the tumor in the patient. Evaluation of the expression profile is then used to determine whether the patient is expected to have a favorable outcome and would benefit from treatment, e.g., NAE inhibition therapy (e.g., treatment with a NAE inhibitor (e.g., MLN4924) alone, or in combination with additional agents)), or an alternative agent expected to have a similar effect on survival. Evaluation of the expression profile can also be used to determine whether a patient is expected to have an unfavorable outcome and would benefit from a cancer therapy other than NAE inhibition therapy or would benefit from an altered NAE inhibition therapy regimen. Evaluation can include use of one marker set prepared using any of the methods provided or other similar scoring methods known in the art (e.g., weighted voting, combination of threshold features (CTF), Cox proportional hazards analysis, principal components scoring, linear predictive score, K-nearest neighbor, etc), e.g., using expression values deposited with the Gene Expresion Omnibus (GEO) program at the National Center for Biotechnology Information (NCBI, Bethesda, Md.). Still further, evaluation can comprise use of more than one prepared marker set. A NAE inhibition therapy will be identified as appropriate to treat the cancer when the outcome of the evaluation demonstrates a favorable outcome or a more aggressive therapy regimen will be identified for a patient with an expected unfavorable outcome.

In one aspect, the invention features a method of evaluating a patient, e.g., a patient with cancer, e.g. a hematological cancer (e.g., multiple myeloma, leukemias, lymphoma, etc) or solid tumor cancer (e.g., melanoma, esophageal cancer or bladder cancer) for treatment outcome. The method includes providing an evaluation of the expression of the markers in a marker set of markers in the patient, wherein the marker set has the following properties: it includes a plurality of genes, each of which is differentially expressed as between patients with identified outcome and non-afflicted subjects and it contains a sufficient number of differentially expressed markers such that differential amount (e.g., as compared to a level in a non-afflicted reference sample) of each of the markers in the marker set in a subject is predictive of treatment outcome with no more than about 15%, about 10%, about 5%, about 2.5%, or about 1% false positives (wherein false positive means predicting that a patient as responsive or non-responsive when the subject is not); and providing a comparison of the amount of each of the markers in the set from the patient with a reference value, thereby evaluating the patient.

Examining the amount of one or more of the identified markers or marker sets in a tumor sample taken from a patient during the course of NAE inhibition therapy, it is also possible to determine whether the therapeutic agent is continuing to work or whether the cancer has become non-responsive (refractory) to the treatment protocol. For example, a patient receiving a treatment of MLN4924 would have tumor cells removed and monitored for the expression of a marker or marker set. If the profile of the amount of one or more markers identified herein more typifies favorable outcome in the presence of the agent, e.g., the NAE inhibitor, the treatment would continue. However, if the profile of the amount of one or more markers identified herein more typifies unfavorable outcome in the presence of the agent, then the cancer may have become resistant to therapy, e.g., NAE inhibition therapy, and another treatment protocol should be initiated to treat the patient. For example, the cancer may comprise a mutation in a marker gene associated with resistance to NAE inhibition.

Importantly, these determinations can be made on a patient-by-patient basis or on an agent-by-agent (or combinations of agents). Thus, one can determine whether or not a particular NAE inhibition therapy is likely to benefit a particular patient or group/class of patients, or whether a particular treatment should be continued.

Use of Information

In one method, information, e.g., about the mutational status of a patient's tumor, e.g., the patient's marker(s) characteristic, e.g., size, sequence, composition or amount (e.g., the result of evaluating a marker or marker set described herein), or about whether a patient is expected to have a favorable outcome, is provided (e.g., communicated, e.g., electronically communicated) to a third party, e.g., a hospital, clinic, a government entity, reimbursing party or insurance company (e.g., a life insurance company). For example, choice of medical procedure, whether to pay for a medical procedure, payment by a reimbursing party, or cost for a service or insurance can be function of the information. E.g., the third party receives the information, makes a determination based at least in part on the information, and optionally communicates the information or makes a choice of procedure, payment, level of payment, coverage, etc. based on the information. In the method, informative expression level of a marker or a marker set selected from or derived from Table 1 and/or described herein is determined.

In one embodiment, a premium for insurance (e.g., life or medical) is evaluated as a function of information about one or more marker expression levels, e.g., a marker or marker set, e.g., a level of expression associated with treatment outcome (e.g., the informative amount). For example, premiums can be increased (e.g., by a certain percentage) if the marker genes of a patient or a patient's marker set described herein have different characteristic, e.g., size, sequence, composition or amount between an insured candidate (or a candidate seeking insurance coverage) and a reference value (e.g., a non-afflicted person) or a reference sample, e.g., matched control. Premiums can also be scaled depending on the result of evaluating a marker or marker set described herein. For example, premiums can be assessed to distribute risk, e.g., as a function of marker, e.g., the result of evaluating a marker or marker set described herein. In another example, premiums are assessed as a function of actuarial data that is obtained from patients that have known treatment outcomes.

Information about marker characteristic, e.g., size, sequence, composition or amount, e.g., the result of evaluating a marker or marker set described herein (e.g., the informative amount), can be used, e.g., in an underwriting process for life insurance. The information can be incorporated into a profile about a subject. Other information in the profile can include, for example, date of birth, gender, marital status, banking information, credit information, children, and so forth. An insurance policy can be recommended as a function of the information on marker characteristic, e.g., size, sequence, composition or amount, e.g., the result of evaluating a marker or marker set described herein, along with one or more other items of information in the profile. An insurance premium or risk assessment can also be evaluated as function of the marker or marker set information. In one implementation, points are assigned on the basis of expected treatment outcome.

In one embodiment, information about marker characteristic, e.g., size, sequence, composition or amount, e.g., the result of evaluating a marker or marker set described herein, is analyzed by a function that determines whether to authorize the transfer of funds to pay for a service or treatment provided to a subject (or make another decision referred to herein). For example, the results of analyzing a characteristic, e.g., size, sequence, composition or amount of a marker or marker set described herein may indicate that a subject is expected to have a favorable outcome, suggesting that a treatment course is needed, thereby triggering an result that indicates or causes authorization to pay for a service or treatment provided to a subject. In one example, informative characteristic, e.g., size, sequence, composition or amount of a marker or a marker set selected from or derived from Table 1 and/or described herein is determined and payment is authorized if the informative amount identifies a favorable outcome. For example, an entity, e.g., a hospital, care giver, government entity, or an insurance company or other entity which pays for, or reimburses medical expenses, can use the result of a method described herein to determine whether a party, e.g., a party other than the subject patient, will pay for services (e.g., a particular therapy) or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In one aspect, the disclosure features a method of providing data. The method includes providing data described herein, e.g., generated by a method described herein, to provide a record, e.g., a record described herein, for determining if a payment will be provided. In some embodiments, the data is provided by computer, compact disc, telephone, facsimile, email, or letter. In some embodiments, the data is provided by a first party to a second party. In some embodiments, the first party is selected from the subject, a healthcare provider, a treating physician, a health maintenance organization (HMO), a hospital, a governmental entity, or an entity which sells or supplies the drug. In some embodiments, the second party is a third party payor, an insurance company, employer, employer sponsored health plan, HMO, or governmental entity. In some embodiments, the first party is selected from the subject, a healthcare provider, a treating physician, an HMO, a hospital, an insurance company, or an entity which sells or supplies the drug and the second party is a governmental entity. In some embodiments, the first party is selected from the subject, a healthcare provider, a treating physician, an HMO, a hospital, an insurance company, or an entity which sells or supplies the drug and the second party is an insurance company.

In another aspect, the disclosure features a record (e.g., computer readable record) which includes a list and value of characteristic, e.g., size, sequence, composition or amount for the marker or marker set for a patient. In some embodiments, the record includes more than one value for each marker.

The present invention will now be illustrated by the following Examples, which are not intended to be limiting in any way.

Examples

Example 1. Cell Line Panel Screens

To support clinical development and identify potential biomarkers of tumor sensitivity or resistance, two large cancer cell line panels (Panel 1, N=653 (McDermott et al. (2007) *PNAS* 104:19936-19941); Panel 2, N=240 (O'Day et al. (2010) Fourth AACR International Conference on Molecular Diagnostics in Cancer Therapeutic Development)) were treated with MLN4924 and cell viability data (IC50, EC50, and POC—Percentage of Control) were generated.

Panel 1 (McDermott et al., supra). The cell lines were exposed to three MLN4924 concentrations (20 nM, 200 nM, and 2 μM) for 72 hours. Viability, i.e., cell number, was quantified by measuring fluorescence of a cell-permeant nucleic acid stain. Mean of triplicate values for each sample were taken and compared to DMSO control to calculate percentage of control. In the results, control or no activity value is given a value of about 1, sensitivity is indicated by a value less than 1, with 0 as death of the entire cell population and resistance indicated by a value greater than 1. A continuum of viability values was obtained for each concentration, so some values were selected as cut-offs for final determination of sensitivity or resistance. For example, median POC values of less than the median value of all POC's recorded in the panel (<0.34) indicated sensitivity, values of 0.34 to 0.75 indicated borderline sensitivity, values greater than the $3^{rd}$ quartile of all POC's in the panel (>0.75) insensitivity or resistance. In general, a dose response relationship was observed with sensitive cell lines. Final judgment of cell line as sensitive, insensitive or resistant was determined by its viability at 2 μM.

Panel 2 (Ricerca Biosciences, Inc., Bothell, Wash.). MLN4924 was added in half-log dilutions for 10 concentrations and treated for 72 hours. High-content cell screening by fluorescence microscopy included image analysis to generate several types of data. Results included EC50 values (after measurement of cell numbers, the EC50 concentration was calculated from the inflection point of a curve of percent of control (POC) against log of MLN4924 concentration), IC50 values (from the POC-log MLN4924 plot, IC50 is the concentration at 50% maximal possible response), apoptosis (measurement of activation of caspase 3 plotted against log of MLN4924 concentration, determined as the concentration for >5 fold induction), and mitotic activity (determined by measuring the fold increase of phospho-histone 3). A comparison of EC50 to IC50 (FIG. 3) allowed assignment of cell lines to sensitive, insensitive or resistant. Final identification of a cell line as sensitive or resistant was based on the EC50 values. The cutoff for sensitivity is a median EC50 of less than the median value of all POC's recorded in the panel (<0.36), borderline sensitivity was associated with median EC50 of 0.36 to 1.67 and insensitive or resistant cell lines were identified by EC50 greater than the $3^{rd}$ quartile of all POC's in the panel (>1.67).

Overlapping cell lines between the panels 1 and 2 (114 overlaps) showed consistent growth inhibition effects (Spearman Correlation coefficient=0.72). In addition, histology and mutation analysis on each cell line panel as a whole (not just overlapping cell lines), also generated consistent observations between the two panels (FIGS. 4A and B).

Fisher's Exact Test using median percentage of control values was used to evaluate associations of individual mutations in the cell lines to MLN4924 sensitivity or resistance. See Table 3 for a summary of p values for selected genes. Genes whose mutations were linked to sensitivity in the Fisher Exact test include NF2, SMAD4, KDM6A, CDKN2A and CDKN2A_p14. RB1 and TP53 were linked to insensitivity.

TABLE 3

Confidence of mutated marker association with response to MLN4924

| Mutated Gene | Total N panel 1 | Number sensitive panel 1 | Panel 1 p-value | Total N panel 2 | Number sensitive panel 2 | Panel 2 p-value | Phenotype |
|---|---|---|---|---|---|---|---|
| NF2 | 10 | 8 | 0.067 | 5 | 4 | 0.187 | Sensitive |
| SMAD4 | 24 | 15 | 0.197 | 11 | 6 | 0.509 | Sensitive |
| KDM6A | 6 | 6 | 0.019 | 4 | 4 | 0.062 | Sensitive |
| RB1 | 32 | 12 | 0.062 | 14 | 17 | 1.00 | Resistant* |
| TP53 | 235 | 112 | 0.013 | 98 | 45 | 0.107 | Resistant |
| CDKN2A | 153 | 94 | 0.001 | 68 | 38 | 0.146 | Sensitive |
| CDKN2A_p14 | 114 | 70 | 0.01 | 59 | 33 | 0.178 | Sensitive |

*denotes phenotype for RB1 association not conclusive across all cell types.

Some tumor types were more associated with resistance than others: tumors from brain, bladder, bone and lung (NSCLC) have p-values of 0.102, 0.205, 0.226, and 0.281, respectively. The result that RB1 is not a sensitivity marker agrees with the result of Jia et al. ((2011) *Neoplasia* 13:561-569) which excluded the involvement of RB1 in MLN4924 mechanism.

Example 2. Analysis of Mutation Associations

One difficulty with correlating mutations of genes in cell lines with sensitivity to a therapeutic agent is that many cell lines have more than one mutated gene. For example, cell line named 8505C from thyroid carcinoma has mutations in BRAF, TP53, NF2 and CDKN2A. In particular, TP53 and CDKN2A mutations co-occurred with other mutations in the cell lines. To learn which mutant is associated with sensitivity or resistance in the cell line panels, sub-analyses were performed.

APC vs TP53.

In cell line panel 1, 23 cell lines have a mutation in APC. Of these, 18 cell lines also have a mutation in TP53. It was difficult to determine whether APC is a driver of resistance to MLN4924, or just a passenger mutation found frequently in TP53 mutants. Further analysis of the cell lines was undertaken by subtraction of cell lines with double mutants which included TP53 (Table 4).

TABLE 4

Comparison of TP53 mutant cell lines with APC and other mutant cell lines in panel 1

| A. | Subtract TP53 mutants | | |
|---|---|---|---|
| Gene | sens(78) | res(51) | p-value |
| RB1 | 0 | 2 | 0.154433 |
| NRAS | 7 | 7 | 0.285024 |

TABLE 4-continued

Comparison of TP53 mutant cell lines with APC and other mutant cell lines in panel 1

| | | | |
|---|---|---|---|
| APC | 2 | 3 | 0.30657 |
| SMAD4 | 2 | 3 | 0.30657 |
| BRCA2 | 0 | 1 | 0.395349 |

TABLE 4-continued

Comparison of TP53 mutant cell lines with APC and other mutant cell lines in panel 1

| | | | |
|---|---|---|---|
| FAM123B | 0 | 1 | 0.395349 |
| MAP2K4 | 0 | 1 | 0.395349 |
| B. | Subtract APC mutants | | |
| Gene | sens(184) | res(158) | p-value |
| TP53 | 108 | 110 | 0.0234828 |
| RB1 | 12 | 19 | 0.0573067 |
| MAP2K4 | 2 | 5 | 0.1665217 |
| C. | Double Mutants | | |
| Gene | sens(190) | res(175) | p-value |
| APC + TP53 | 4 | 14 | 0.00842 |

As can be seen in Table 4A, subtracting TP53 mutants from the cell line panel leaves an N too small to allow conclusion of association of remaining mutations with resistance of the TP53 wt cell lines to treatment with MLN4924. After removing all 23 APC mutants, TP53 still appears to be associated with resistance (Table 4B). Nevertheless, cell lines with both APC and TP53 mutations show strong association to resistance (Table 4C). Additionally, a majority of the cell lines in the APC+TP53 mutant subgroup are from intestinal cancer tumor samples (Table 5, which also includes cell lines and data from panel 2 and six panel 1 cell lines which were not included in the original subtractive analysis).

TABLE 5

| Subset of cell lines with mutations in APC and TP53 | | | | | |
|---|---|---|---|---|---|
| Cell line | Tumor Tissue Source | Tumor Histology | Viability at 2 μM Panel 1 | EC50 Panel 2 | Co-occurring mutations |
| HT55 | intestine | colon carcinoma | 0.5143 | | APC:APC:TP53 |
| SW 1116 | intestine | colon adenocarcinoma | 1.1599 | 10 | APC:APC:KRAS:SMAD4:TP53 |
| COCM1 | intestine | colon carcinoma | 1.1438 | | APC:APC:PIK3CA:SMAD4:TP53 |
| LS1034 | intestine | adenocarcinoma | | 3.76 | APC:KRAS:TP53 |
| SW 1463 | intestine | rectum adenocarcinoma | 0.8963 | | TP53:FBXW7:KRAS:APC |
| NCI-H630 | intestine | colorectal adenocarcinoma | 0.75 | | APC:TP53 |
| SW1417 | intestine | colon adenocarcinoma | 0.6374 | 9.03 | APC:TP53:BRAF:PIK3R1 |
| SW837 | intestine | rectum adenocarcinoma | 0.702 | 0.694 | APC:APC: FAM123B:TP53:FBXW7:KRAS |
| SW620 | intestine | colon adenocarcinoma | 0.4928 | 0.387 | APC:TP53:TP53:KRAS:MAP2K4:SMAD4 |
| NCI-H1581 | lung NSCLC | squamous cell carcinoma | 0.7365 | | APC:TP53 |
| HCT-15 | intestine | colon adenocarcinoma | 0.6654 | 0.836 | APC:BRCA2:FAM123B:KRAS:MSH6: PIK3CA:TP53 |
| C2BBe1 | intestine | colorectal adenocarcinoma | 0.7159 | | APC:TP53 |
| T84 | intestine | colon carcinoma | 0.5777 | 0.556 | KRAS:PIK3CA:TP53:APC |
| SW626 | ovary | adenocarcinoma | 0.5541 | | TP53:KRAS:APC |
| HT29 | intestine | colorectal adenocarcinoma | 0.4376 | 0.25 | APC:PIK3CA:TP53:BRAF:SMAD4:APC |
| LK-2 | lung | lung NSCLC | 0.2893 | | TP53:APC:CDKN2A |
| MKN28 | stomach | metastasis | 0.2847 | | APC:TP53:NF1 |
| COLO-205 | intestine | colon adenocarcinoma | 0.144 | 0.0923 | TP53:BRAF:APC:SMAD4 |
| HGC-27 | stomach | gastric carcinoma | 0.1291 | | TP53:APC:PTEN:PIK3CA |
| NCIH747 | intestine | cecum adenocarcinoma | | 2.07 | APC:APC:KRAS:TP53 |
| SKUT1 | smooth muscle | leiomyosarcoma | | 0.0856 | APC:APC:PIK3CA:PTEN:PTEN:RB1:TP53: TP53 |
| SK-MEL-30 | skin | malignant melanoma | 0.7728 | | APC:NRAS:TP53 |
| COLO320 HSR | intestine | colon adenocarcinoma | | 1.78 | APC:TP53 |
| NCI-H520 | lung NSCLC | squamous cell carcinoma | 0.5577 | 0.261 | CDKN2A:APC:TP53 |
| NCI-H1703 | lung NSCLC | adenosquamous carcinoma | 0.1101 | | TP53:APC:CDKN2A |
| NCI-H1975 | lung | adenocarcinoma | 0.3049 | | TP53:APC:CDKN2A:PIK3CA:EGFR |
| RCM-1 | intestine | rectum adenocarcinoma | 0.7666 | | TP53:KRAS:APC |
| SK-OV-3 | ovary | adenocarcinoma | 0.397 | 10 | TP53:PIK3CA:CDKN2A:APC |

Association with Histology.

It is possible that some TP53 mutations associate with resistance in some types of tumor more than others. TP53 mutant cell lines were analyzed within tissue types by a Mann-Whitney (nonparametric) test. As can be seen in FIG. 5, TP53 mutations are significantly correlated with resistance to MLN4924 in colon cancer cell lines (p-value=0.04022).

Similar analysis of associations in other tissues indicates that TP53 mutation is associated with MLN4924 resistance in breast cancer and lung cancer (NSCLC) cell lines.

Additional mutations were analyzed for possible association of tumor histology with resistance or sensitivity to MLN4924 treatment. Table 6 provides results from analysis of panel 1 and Table 7 provides results from analysis of panel 2, whose smaller size proved a challenge for this type of analysis. The cutoff of association with the tissues was chosen at p-values of <0.05.

TABLE 6

Association of mutation with histology in Panel 1

| Tumor Tissue Source | Mutation | N mutants this cancer | N wild type this cancer | N mutants all cancers | N wild type all cancers | Association | p-value |
|---|---|---|---|---|---|---|---|
| Head_Neck | TP53 | 15 | 1 | 111 | 79 | sensitive | 0.0001 |
| Head_Neck | CDKN2A | 12 | 4 | 94 | 96 | sensitive | 0.0072 |
| Head_Neck | SMAD4 | 3 | 13 | 15 | 175 | sensitive | 0.0262 |
| Cervix | TP53 | 1 | 6 | 124 | 51 | resistant | 0.0027 |
| Lung | RB1 | 2 | 4 | 19 | 156 | resistant | 0.0178 |
| Bone | RB1 | 1 | 5 | 12 | 178 | sensitive | 0.0477 |

TABLE 7

Association of mutation with histology in Panel 2

| Tumor Tissue Source | Mutation | N mutants this cancer | N wild type this cancer | N mutants all cancers | N wild type all cancers | Association | p-value |
|---|---|---|---|---|---|---|---|
| skin | CDKN2A | 8 | 1 | 30 | 43 | resistant | 0.0022 |
| skin | CDKN2A.p14 | 6 | 3 | 26 | 47 | resistant | 0.0004 |
| skin | TP53 | 2 | 7 | 53 | 20 | resistant | 0.0036 |
| CNS | CDKN2A.p14 | 5 | 4 | 26 | 47 | resistant | 0.0466* |

*p-value for CNS derived from percent of control viability. For skin, p-value derived from EC50.

In contrast to the general association of TP53 with resistance to MLN4924, in head and neck cancer, TP53 mutation is associated with sensitivity. A similar contrast was found for CDKN2A mutations in skin and central nervous system (CNS). CDKN2A or CDKN2A.p14 mutations were associated with resistance to MLN4924 treatment in skin and CNS tumor cell lines, despite the general association with CDKN2A mutation and sensitivity to MLN4924 treatment. Tables 6 and 7 also show that TP53 mutations are significantly associated with resistance in cervical cancer and skin cancer; CDKN2A mutations are significantly associated with sensitivity in head and neck cancer; SMAD4 mutations are significantly associated with sensitivity in head and neck cancer; RB1 mutations are significantly associated with resistance in lung cancer; and RB1 mutations are significantly associated with sensitivity in bone cancer.

Example 3. Individual Cell Line Screening Results

The following tables include results of the individual cell line screens which led to conclusions about markers whose mutations confer sensitivity to MLN4924.

Notation of the mutations and explanation of mutation syntax can be found in the COSMIC database.

TABLE 8

Results of screens of cell lines with mutations in NF2.

| Cell line | ORF mutation (SEQ ID NO: 2) | Protein mutation (SEQ ID NO: 3) | Tumor Tissue Source | Tumor type | Viability at 2 μM Panel 1 | EC50 Panel 2 | Phenotype | Co-occurring mutations |
|---|---|---|---|---|---|---|---|---|
| 647-V | c.115-1G > C | p.? | urinary_tract | primary | 0.038 | 0.283 | sensitive | MAP2K4:NF2:RB1:TP53:TP53 |
| ACHN | c.169C > T | p.R57* | kidney | primary | 0.0621 | 0.652 | sensitive | CDKN2A:CDKN2a(p14):NF2 |
| CAL-62 | c.643G > T | p.E215* | thyroid | primary | 0.0676 | 0.0837 | sensitive | CDKN2A:CDKN2a(p14):KRAS:NF2:TP53 |
| NUGC-3 | c.683delA | p.K228fs*23 | stomach | primary | 0.098 | | sensitive | NF2:TP53 |
| SW1573 | c.1_363del363 | p.? | lung | primary | 0.1114 | | sensitive | CDKN2A:CDKN2a(p14):CTNNB1:KRAS:NF2:PIK3CA:SMAD4 |
| 8505C | c.385G > T | p.E129* | thyroid | primary | 0.1405 | | sensitive | BRAF:CDKN2A:NF2:TP53 |
| CaR-1 | c.115_1737del1623 | p.? | large_intestine | primary | 0.3244 | | sensitive | CDKN2A:CDKN2a(p14):NF2:STK11:TP53 |
| SN12C | c.115-1G > C | p.? | kidney | primary | 0.3357 | | sensitive | NF2:TP53 |
| MDA-MB-231 | c.691G > T | p.E231* | breast | primary | 0.5284 | 0.871 | insensitive | BRAF:CDKN2A:CDKN2a(p14):KRAS:NF2:TP53 |
| S-117 | c.221G > A | p.W74* | soft_tissue | primary | 0.6412 | | resistant | CDKN2A:CDKN2a(p14):NF2:TP53 |
| RL95-2 | c.514delA<br>c.1084C > T | p.R172fs*2<br>p.Q362* | endometrium | primary | | 0.094 | sensitive | BRCA2:BRCA2:HRAS:NF2:NF2:PTEN:PTEN:TP53:TP53 |

TABLE 9

Results of screens of cell lines with mutations in SMAD4.

| Cell line | ORF mutation (SEQ ID NO: 5) | Protein mutation (SEQ ID NO: 6) | Tumor Tissue Source | Tumor type | Viability at 2 μM Panel 1 | EC50 Panel 2 | Phenotype | Co-occurring mutations |
|---|---|---|---|---|---|---|---|---|
| CAL-27 | c.733C > T | p.Q245* | upper__aerodigestive__tract | primary | 0.0271 | 0.139 | sensitive | CDKN2A:SMAD4:TP53 |
| KP-4 | c.1__1659del1659 | p.0? | pancreas | metastasis | 0.0518 | | sensitive | CDKN2A:CDKN2a(p14):KRAS:SMAD4 |
| GAMG | c.1__249del249 | p.? | central__nervous__system | primary | 0.0721 | | sensitive | CDKN2A:CDKN2a(p14):SMAD4:TP53 |
| PANC-03-27 | c.905__1659del755 | p.? | pancreas | primary | 0.0724 | | sensitive | CDKN2A:CDKN2a(p14):KRAS:SMAD4:TP53 |
| FADU | c.1__1659del1659 | p.0? | upper__aerodigestive__tract | primary | 0.073 | 0.261 | sensitive | CDKN2A:SMAD4:TP53:TP53 |
| SW1573 | c.1__1659del1659 | p.0? | lung | primary | 0.1114 | | sensitive | CDKN2A:CDKN2a(p14):CTNNB1:KRAS:NF2:PIK3CA:SMAD4 |
| KYSE-150 | c.788-1G > A | p.? | oesophagus | primary | 0.1279 | | sensitive | SMAD4:TP53 |
| COLO-205 | c.1__667del667 | p.? | large__intestine | primary | 0.144 | 0.0923 | sensitive | APC:BRAF:SMAD4:TP53 |
| CAL-33 | c.766C > T | p.Q256* | upper__aerodigestive__tract | primary | 0.1445 | | sensitive | CDKN2A:PIK3CA:SMAD4:TP53 |
| NCI-N87 | c.1__955del955 | p.? | stomach | metastasis | 0.1461 | | sensitive | SMAD4:TP53 |
| CAPAN-1 | c.1028C > G | p.S343* | pancreas | metastasis | 0.1473 | 0.365 | sensitive? | BRCA2:CDKN2A:CDKN2a(p14):KRAS:SMAD4:TP53 |
| YAPC | c.1543delA | p.R515fs*22 | pancreas | primary | 0.1871 | 0.234 | sensitive | CDKN2A:CDKN2a(p14):KRAS:SMAD4:TP53 |
| NCI-H2405 | c.1__1659del1659 | p.0? | lung | metastasis | 0.2554 | | sensitive | BRAF:CDKN2A:CDKN2a(p14):MAP2K4:SMAD4:TP53 |
| CFPAC-1 | c.1__1659del1659 | p.0? | pancreas | metastasis | 0.2822 | 6.37 | sensitive? | KRAS:SMAD4:TP53 |
| MDA-MB-468 | c.1__1659del1659 | p.0? | breast | metastasis | 0.2965 | 0.0267 | sensitive | PTEN:RB1:SMAD4:TP53 |
| MKN45 | c.1__1659del1659 | p.0? | stomach | metastasis | 0.3614 | | insensitive | CDKN2A:CDKN2a(p14):SMAD4 |
| BxPC-3 | c.1__1659del1659 | p.0? | pancreas | primary | 0.4186 | 0.251 | insensitive | CDKN2A:CDKN2a(p14):MAP2K4:SMAD4:TP53 |
| HT-29 | c.931C > T | p.Q311* | large__intestine | primary | 0.4376 | 0.25 | insensitive | APC:APC:BRAF:PIK3CA:SMAD4:TP53 |
| UMC-11 | c.1606__1612del CTAGACG | p.L536fs*14 | lung | primary | 0.4472 | | insensitive | CDKN2A:CDKN2a(p14):SMAD4:STK11:TP53 |
| SW620 | c.955 + 5G > C | p.? | large__intestine | primary | 0.4928 | 0.387 | insensitive | APC:KRAS:MAP2K4:SMAD4:TP53:TP53 |
| PANC-08-13 | c.366__367insA | p.C123fs*2 | pancreas | primary | 0.7767 | | resistant | CDKN2A:CDKN2a(p14):KRAS:SMAD4 |
| COLO-678 | c.1__1659del1659 | p.0? | large__intestine | metastasis | 0.814 | | resistant | APC:CDKN2A:CDKN2a(p14):FAM123B:KRAS:SMAD4 |
| CoCM-1 | c.956__1659del704 | p.? | large__intestine | primary | 1.1438 | | resistant | APC:APC:PIK3CA:SMAD4:TP53 |
| SW954 | c.378__379delCT | p.V128fs*14 | vulva | primary | | 0.324 | sensitive | SMAD4:TP53 |

TABLE 10

Results of screens of cell lines with mutations in KDM6A.

| Cell line | ORF mutation (SEQ ID NO: 8 or 9) | Protein mutation (SEQ ID NO: 10 or 11) | Tumor Tissue Source | Tumor type | Viability at 2 μM Panel 1 | EC50 Panel 2 | Phenotype | Co-occurring mutations |
|---|---|---|---|---|---|---|---|---|
| HCC1806 | c.444__564del121 | p.0 | breast | primary | 0.0116 | | sensitive | CDKN2A:CDKN2a(p14):KDM6A:STK11:TP53 |
| KU-19-19 | c.2587C > T | p.Q863* | urinary__tract | primary | 0.058 | | sensitive | CDKN2A:CDKN2a(p14):KDM6A:NRAS |
| MIA-PaCa-2 | c.1__4206del4206 | p.0? | pancreas | primary | 0.1145 | 0.239 | sensitive | CDKN2A:CDKN2a(p14):KDM6A:KRAS:TP53 |
| KYSE-450 | c.385__654del270 | p.0 | oesophagus | primary | 0.1426 | | sensitive | CDKN2A:CDKN2a(p14):EGFR:KDM6A:NOTCH1:TP53:TP53 |
| KYSE-180 | c.997C > T | p.Q333* | oesophagus | primary | 0.2154 | | sensitive | CDKN2A:CDKN2a(p14):KDM6A:TP53 |

TABLE 10-continued

| Results of screens of cell lines with mutations in KDM6A. | | | | | | | | |
|---|---|---|---|---|---|---|---|---|
| Cell line | ORF mutation (SEQ ID NO: 8 or 9) | Protein mutation (SEQ ID NO: 10 or 11) | Tumor Tissue Source | Tumor type | Viability at 2 μM Panel 1 | EC50 Panel 2 | Phenotype | Co-occurring mutations |
| LS-174T | c.3945_3946insA | p.E1316fs*17 | large_intestine | primary | 0.3262 | 0.137 | sensitive | CTNNB1:KDM6A: KRAS:PIK3CA |
| BV-173 | c.226_384del159 | p.0 | haematopoietic, lymphoid_tissue | primary | | 0.131 | sensitive | CDKN2A:CDKN2a(p14):KDM6A |
| THP-1 | c.1_1923del1923 | p.0 | haematopoietic, lymphoid_tissue | primary | | 0.148 | sensitive | CDKN2A:CDKN2a(p14): KDM6A:NRAS:TP53 |

TABLE 11

| Sampling of results of screens of cell lines with mutations in FBXW7. | | | | | | | | |
|---|---|---|---|---|---|---|---|---|
| Cell line | ORF mutation (SEQ ID NO: 13) | Protein mutation (SEQ ID NO: 14) | Tumor Tissue Source | Tumor type | Viability at 2 μM Panel 1 | EC50 Panel 2 | Phenotype | Co-occurring mutations |
| AN3CA | c.1321C > T | p.R441W | Uterus | metastasis | 0.1944 | | sensitive | PTEN: TP53: PIK3R1 |
| ESS-1 | c.1393C > T | p.R465C | Uterus | primary | 0.0529 | | sensitive | FBXW7: TP53: PIK3CA: RB1 |
| C-33a | c.1394G > A | p.R465H | Cervix | primary | 0.0822 | | sensitive | RB1: TP53: MSH2: PIK3CA: PTEN |
| HuCCT1 | c.881C > G | p.S294* | Liver | primary | 0.1262 | | sensitive | TP53: KRAS |
| MKN1 | c.1393C > T | p.R465C | Stomach | metastasis | 0.4631 | | insensitive | TP53: PIK3CA |
| AsPC-1 | c.1393C > T | p.R465C | Pancreas | metastasis | 0.9889 | | resistant | CDKN2A: MAP2K4: KRAS: TP53 |
| RCM-1 | c.1513C > T | p.R505C | Intestine | primary | 0.7666 | | resistant | TP53: KRAS |
| SW1463 | c.1436G > A | p.R479Q | Intestine | primary | 0.8963 | | resistant | TP53: KRAS: APC |

Example 4. Association of TP53 Deletion with Resistance

Another approach to determine the role of TP53 in responsiveness to MLN4924 was a study in which the TP53 gene was deleted. In earlier studies, the importance of p53 in the rereplication response to MLN4924 seemed to be dependent on the specific genetic manipulation and was expected to closely mirror that of CDT1 overexpression (Cdt1 is a substrate of two alternative CRL complexes and is stabilized by MLN4924 in many cell lines). In knockdown studies, p53 appeared to behave similarly to CDT1 knockdown at early timepoints, but not later timepoints, unless higher concentrations of MLN4924 were used. Western blotting suggested efficient p53 protein knockdown by the siRNA SMARTpool, although RNAi generally does not result in the complete loss of protein. Therefore, the residual protein may still affect the response to MLN4924, particularly since MLN4924 results in the stabilization of p53 (Liao et al. (2011) Mol. Cell Proteomics 10:10.1074/mcp.M111.009183). The viability effect of MLN4924 was assessed on HCT-116 cells that were genetically deleted for p53 together with their parental control.

Paired isogenic HCT-116 cell lines that were either wild-type (+1+) or null (−/−) for p53 expression (HD PAR-018 and HD 104-001, respectively, Horizon Discovery Ltd) were seeded in separate 384-well plates and then treated the following day with a titration of MLN4924 in triplicate, and incubated for 24, 36, 48 or 72 h, with seeding densities of 1600, 1200, 800, and 400 cells/well, respectively. Following compound incubation, viability of HCT-116 cells was assessed by ATPlite assay (Perkin Elmer) according to the manufacturer's instructions using the LEADseeker imaging system (GE Healthcare).

HCT-116 TP53+/+ cells (MLN4924 $LC_{50}$=21±1 nM) demonstrated greater MLN4924 sensitivity at 72 h than HCT-116 TP53−/− cells (MLN4924 $LC_{50}$=74±5 nM; FIGS. 6A-D). These results suggest that p53 deficiency makes HCT-116 less sensitive to MLN4924, suggesting that the overarching role of p53 at 72 h is proapoptotic. Earlier time points reinforce this interpretation, as TP53−/− cells have less cell death at the highest drug concentrations at 24, 36, and 48 h. Western blots showed that p21 was still up-regulated by MLN4924 in TP53−/− HCT-116 cells. In HCT-116 cells, the stabilization of p21 may be a direct effect of inhibition of CRL4-Cdt2 (Nishitani et al., 2008; Abbas et al., 2008; Kim et al., 2008).

This result is contrary to the conclusion in Lin et al. (2010) Cancer Res. 70: 10310-10320) using the HCT116−/− p53 knockout cells. In that study, it was concluded that the TP53 knockout cells were more susceptible to overall cell death or growth inhibition by MLN4924. The reason the present study comes to a different conclusion than in Lin et al. is the amount of time the cells were treated with MLN4924. In Lin et al, the cells were treated for 8 hours before a washout. In the present studies and in the cell line panels of the earlier examples, the cells were treated with MLN4924 continuously over 72 hours. In the washout, the p53 levels are allowed to stabilize and take advantage of activating alternative pathways than the earlier pathways which were initially inhibited and led to the earlier susceptibility.

Example 5. Isolation of Nucleic Acid and Nucleic Acid Sequencing Methods

Genomic Isolations and DNA Sequencing.

DNA isolation from cells and tumors is conducted using DNAEASY® isolation kit (Qiagen, Valencia, Calif.). RNA isolation is conducted using MegaMax (Ambion division of Applied Biosystems, Austin, Tex.). Genomic isolations are conducted following manufacturer recommend protocols.

SANGER Sequencing Methodology.

PCR amplifications are conducted using optimized cycling conditions per gene-exon. Primer extension sequencing is performed using Applied Biosystems BigDye version 3.1. The reactions are then run on Applied Biosystem's 3730×l DNA Analyzer. Sequencing base calls are done using KB™ Basecaller (Applied Biosystems). Somatic Mutation calls are determined by Mutation Surveyor (SoftGenetics) and confirmed manually by aligning sequencing data with the corresponding reference sequence using Seqman (DNASTAR).

SEQUENOM Sequencing Methodology.

Sequenom (San Diego, Calif.) assays are designed using TypePLEX® chemistry with single-base extension. This process consists of three steps: 1) A text file containing the SNPs or mutations of interest and flanking sequence is uploaded at mysequenom.com where it is run through a web based program ProxSNP, 2) The output of ProxSNP is run through PreXTEND and 3) the output of PreXTEND is run through Assay Design which determines the expected mass weight of the extend products to ensure separation between all potential peaks found within a multiplexed reaction.

PCR primers are then designed to bracket the region identified in the assay design steps. The region of interest is amplied in PCR reactions using the primers. 15 nl of amplified and extended product is spotted on a 384 SpectroCHIP II using a Nanodispenser RS1000. A 3-point calibrant is added to every chip to ensure proper performance of the Sequenom Maldi-tof compact mass spectrometer.

The SpectroCHIP II is placed in the Sequenom MALDI-TOF compact mass spectrometer. The mass spectrometer is set to fire a maximum of 9 acquisitions for each spot on the 384 well SpectroCHIP. TypePLEX Gold kit SpectroCHIP II from Sequenom (10142-2) is used following manufacturers recommended protocols. Analysis is performed using Sequenom analysis software, MassARRAY® Typer Analyzer v4.

Next Generation Sequencing (NGS) Methodology.

Targeted NGS using the Illumina platform (Illumina, Inc. San Diego, Calif.) is used to confirm and identify low frequency mutations in a marker. Primer pairs are designed to amplify coding exons. PCR products are quantified using a PicoGreen assay and combined in equal molar ratios for each sample. The purified products are end-repaired and concatenated by ligation. The concatenated products are used for Hi-Seq 2000 library preparation. The concatenated PCR products are sheared and used to make barcoded Hi-Seq 2000 libraries consisting of 12 barcoded samples per multiplexed pool. The pooled Hi-Seq 2000 libraries undergo clonal amplification by cluster generation on eight lanes of a Hi-Seq 2000 flow cell and are sequenced using 1×100 single-end sequencing on a Hi-Seq 2000. Matching of primary sequencing reads to the human genome build Hg18, as well as SNP analysis are performed using Illumina's CASAVA software version 1.7.1.

General Procedures

Quantitative RT-PCR cDNA synthesis and quantitative RT-PCR is performed using ABI Gene Expression Assays, reagents, and ABI PRISM® 7900HT Sequence Detection Systems (Applied Biosystems, Foster City, Calif.) using the following cycle conditions: hold at 50° C. for 2 minutes for AmpErase UNG activation, then 95.0° C. for 10 minutes to activate DNA polymerase then run 40 two-part cycles of 95.0° C. for 15 seconds and 60.0° C. for 1 minute. The dCt is calculated by using the average Ct of control genes B2M (Hs99999907_m1) and RPLPO (Hs99999902_m1). Relative mRNA expression quantification is derived using the Comparative Ct Method (Applied Biosystems). mRNA expression fold change values are generated from a normal sample and corresponding tumor sample.

Sample Handling for Myeloma Samples

Upon collection of patient bone marrow aspirate, the myeloma cells are enriched via rapid negative selection. The enrichment procedure employs a cocktail of cell-type specific antibodies coupled with an antibody that binds red blood cells RosetteSep (Stem Cell Technologies). The antibody cocktail has antibodies with the following specificity: CD14 (monocytes), CD2 (T and NK cells), CD33 (myeloid progenitors and monocytes), CD41 (platelets and megakaryocytes), CD45RA (naïve B and T cells) and CD66b (granulocytes). The antibodies cross-link the non-myeloma cell types to the red blood cells in the samples. The bound cell types are removed using a modified ficoll density gradient. Myeloma cells are then collected and frozen.

Total RNA is isolated using a QIAGEN® Group RNEASY® isolation kit (Valencia, Calif.) and quantified by spectrophotometry.

DNA is isolated from the flow through fraction of the column used in the RNA isolation method.

Analysis of Myeloma Gene Expression on an Array

RNA is converted to biotinylated cRNA by a standard T7 based amplification protocol (AFFYMETRIX® Inc., Santa Clara, Calif.). A small number of samples with ≥0.5-2.0 μg are also labeled and subsequently hybridized if 6 μg of cRNA is produced. For the automated T7 amplification procedure, the cDNA and the biotin labeled cRNA are purified using AMPURE® PCR Purification System, following the manufacturer's protocol (AGENCOURT® Bioscience Corporation, Beverly, Mass.). The cRNA yield is assessed by spectrophotometry and 10 μg of cRNA is fragmented and further processed for triplicate hybridization on the AFFYMETRIX® Human Genome HG-U133A and HG-U133B GENECHIP® arrays. In cases where cRNA yield ranged between 6 μg to 10 μg, the entire cRNA sample is fragmented.

cRNA for each sample is hybridized to the U133A/B arrays in triplicate; operators, chip lots, clinical sites and scanners (GENECHIP® Scanner 3000) are controlled throughout. Background subtraction, smoothing adjustment, noise corrections, and signal calculations are performed with AFFYMETRIX® MAS5.0. Quality control metrics include: percent present call (>25) scale factor (<11), β-actin 3':5' ratio (<15) and background (<120). Samples that fall outside these metrics are excluded from subsequent analysis.

The myeloma purity score examines expression of genes known in the literature to be expressed highly in myeloma cells (and their normal plasma precursor cells), to expression of genes known to be expressed highly in erythroid cells, neutrophils and T cells—see list of 14 markers below). The myeloma score=expression of myeloma markers (#1-4 below)/erythroid (#5-7)+neutrophil (#8-11)+T cell (#12-14):

1. 205692_s_at CD38 CD38 antigen (p45) myeloma/plasma cell
2. 201286_at SDC1 syndecan-1 myeloma/plasma cell
3. 201891_s_at B2M beta-2 microglobulin myeloma/plasma cell
4. 211528_x_at B2M beta-2 microglobulin myeloma/plasma cell
5. 37986_at EpoR erythropoetin receptor erythroid cell
6. 209962_at EpoR erythropoetin receptor erythroid cell 7. 205838_at GYPA glycophorinA erythroid cell
8. 203948_s_at MPO myeloperoxidase neutrophil
9. 203591_s_at CSFR3colony stimulating factor 3receptor (granulocyte) neutrophil
10. 204039_at CEBPACCAAT/enhancer bindingprotein (C/EBP), alpha neutrophil
11. 214523_at CEBPECCAAT/enhancer bindingprotein (C/EBP), epsilon neutrophil
12. 209603_at GATA3 GATA binding protein 3 T lymphocyte
13. 209604_s_at GATA4 GATA binding protein 4 T lymphocyte
14. 205456_at CD3ECD3E antigen, epsilon polypeptide T lymphocyte Samples with a myeloma purity score less than 10 are excluded from further analysis.

EQUIVALENTS

Although embodiments of the invention have been described using specific terms, such description are for illustrative purposes only, and it is to be understood that changes and variations may be made without departing from the spirit or scope of the invention. Those skilled in the art will recognize, or be able to ascertain using no more than routine experimentation, many equivalents of the specific embodiments of the invention described herein. Such equivalents are intended to be encompassed by the following claims.

What is claimed:

1. A method of treating cancer, comprising a) detecting, in a human subject, the presence of an inactivating mutation in at least one human marker gene, wherein the at least one marker gene is human tumor protein p53 (TP53) having a sequence of SEQ ID NO:15;

b) administering ((1S,2S,4R)-4-{4-[(1S)-2,3-dihydro-1H-inden-1-ylamino]-7H-pyrrolo [2,3-d]pyrimidin-7-yl}-2-hydroxycyclopentyl)methyl sulphamate or a pharmaceutically acceptable salt thereof, to the subject having the mutation;

c) obtaining a tumor sample from the subject after administering the ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate or a pharmaceutically acceptable salt thereof;

d) detecting the presence or absence of an inactivating mutation in at least one human marker gene in the tumor sample, wherein the at least one human marker gene is human TP53 having a sequence of SEQ ID NO:15; and e) continuing to administer the ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate or a pharmaceutically acceptable salt thereof to the subject when the mutation is detected.

2. The method of claim 1, wherein the pharmaceutically acceptable salt is a hydrochloride salt.

3. The method of claim 1, wherein the cancer is a hematological cancer or a solid tumor cancer.

4. The method of claim 3, wherein the solid tumor cancer is head and neck cancer.

5. The method of claim 3, wherein the hematological cancer is selected from the group consisting of multiple myeloma, acute myelogenous leukemia, Waldenstrom's syndrome, chronic lymphocytic leukemia, chronic myelogenous leukemia, B-cell lymphoma, non-Hodgkin's lymphoma, Hodgkin's lymphoma, and myelodysplastic syndrome.

6. A method of treating cancer, comprising a) detecting, in a human subject, the absence of a mutation in a TP53 sequence of SEQ ID NO:15, b) administering ((1S,2S,4R)-4-{4-[(1S)-2,3-dihydro-1H-inden-1-ylamino]-7H-pyrrolo [2,3-d]pyrimidin-7-yl}-2-hydroxycyclopentyl)methyl sulphamate or a pharmaceutically acceptable salt thereof, to the subject;

c) obtaining a tumor sample from the subject after administering the ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate or a pharmaceutically acceptable salt thereof;

d) detecting the presence or absence of a mutation in at least one human marker gene in the tumor sample, wherein the at least one human marker gene is human TP53 having a sequence of SEQ ID NO:15; and e) continuing to administer the ((1S,2S,4R)-4-{4-[(1S)-2,3-dihydro-1H-inden-1-ylamino]-7H-pyrrolo[2,3-d]pyrimidin-7-yl}-2-hydroxycyclopentyl)methyl sulphamate or a pharmaceutically acceptable salt thereof to the subject when a mutation is absent.

7. The method of claim 6, wherein the pharmaceutically acceptable salt is a hydrochloride salt.

8. The method of claim 6, wherein the cancer is a hematological cancer or a solid tumor cancer.

9. The method of claim 8, wherein the solid tumor cancer is cervical cancer.

10. The method of claim 8, wherein the solid tumor cancer is skin cancer.

11. The method of claim 8, wherein the solid tumor cancer is CNS cancer.

12. The method of claim 8, wherein the hematological cancer is selected from the group consisting of multiple myeloma, acute myelogenous leukemia, Waldenstrom's syndrome, chronic lymphocytic leukemia, chronic myelogenous leukemia, B-cell lymphoma, non-Hodgkin's lymphoma, Hodgkin's lymphoma, and myelodysplastic syndrome.

* * * * *